US012606553B2

(12) United States Patent
Vaswani et al.

(10) Patent No.: US 12,606,553 B2
(45) Date of Patent: Apr. 21, 2026

(54) CRYSTALLINE FORMS, COMPOSITIONS CONTAINING SAME, AND METHODS OF THEIR USE

(71) Applicant: FOGHORN THERAPEUTICS INC., Watertown, MA (US)

(72) Inventors: Rishi G. Vaswani, Lexington, MA (US); Chong-Hui Gu, Waban, MA (US)

(73) Assignee: FOGHORN THERAPEUTICS INC., Watertown, MA (US)

( * ) Notice: Subject to any disclaimer, the term of this patent is extended or adjusted under 35 U.S.C. 154(b) by 323 days.

(21) Appl. No.: 18/281,022

(22) PCT Filed: Mar. 9, 2022

(86) PCT No.: PCT/US2022/019506
§ 371 (c)(1),
(2) Date: Sep. 8, 2023

(87) PCT Pub. No.: WO2022/192365
PCT Pub. Date: Sep. 15, 2022

(65) Prior Publication Data
US 2024/0158387 A1 May 16, 2024

Related U.S. Application Data

(60) Provisional application No. 63/158,716, filed on Mar. 9, 2021.

(51) Int. Cl.
*C07D 417/14* (2006.01)
*A61K 9/48* (2006.01)
*A61K 45/06* (2006.01)

(52) U.S. Cl.
CPC .......... *C07D 417/14* (2013.01); *A61K 9/4816* (2013.01); *A61K 9/4858* (2013.01); *A61K 9/4866* (2013.01); *A61K 45/06* (2013.01); *C07B 2200/13* (2013.01)

(58) Field of Classification Search
CPC .................................................... C07D 417/14
See application file for complete search history.

(56) References Cited

U.S. PATENT DOCUMENTS 2,788,341 A 4/1957 Schwyzer et al.
3,717,642 A 2/1973 Von Strandtmann
4,109,496 A 8/1978 Allemann et al.
4,650,796 A 3/1987 George et al.
4,868,103 A 9/1989 Stavrianopoulos et al.
5,223,409 A 6/1993 Ladner et al.
5,225,422 A 7/1993 Nagata et al.
5,283,317 A 2/1994 Saifer et al.
5,631,169 A 5/1997 Lakowicz et al.
5,677,158 A 10/1997 Zhou et al.
5,801,030 A 9/1998 McVey et al.
5,858,358 A 1/1999 June et al.
5,883,223 A 3/1999 Gray
6,180,612 B1 1/2001 Hockensmith et al.
6,309,634 B1 10/2001 Bankiewicz et al.
6,352,694 B1 3/2002 June et al.
6,551,786 B2 4/2003 Manfredi
6,683,058 B1 1/2004 Tuszynski
6,692,964 B1 2/2004 June et al.
6,716,662 B2 4/2004 Akai
6,797,514 B2 9/2004 Berenson et al.
6,867,041 B2 3/2005 Berenson et al.
6,887,466 B2 5/2005 June et al.
6,905,680 B2 6/2005 June et al.
6,905,681 B1 6/2005 June et al.
6,905,874 B2 6/2005 Berenson et al.
6,995,011 B2 2/2006 Itoh et al.
7,067,318 B2 6/2006 June et al.
7,144,575 B2 12/2006 June et al.
7,172,869 B2 2/2007 June et al.
7,175,843 B2 2/2007 June et al.
(Continued)

FOREIGN PATENT DOCUMENTS

CN 103038231 A 4/2013
CN 104530013 B 6/2016
(Continued)

OTHER PUBLICATIONS

U.S. Appl. No. 18/282,279, Huang, Liyue.
(Continued)

*Primary Examiner* — Golam M Shameem
(74) *Attorney, Agent, or Firm* — Clark & Elbing LLP

(57) ABSTRACT

Disclosed are crystalline forms of the compound of formula (I): (I) Also disclosed are compositions containing the crystalline forms of the compound of formula (I) and methods of their use. The methods may be for treating cancer in a subject in need thereof, e.g., by administering to the subject an effective amount of the crystalline form disclosed herein or its composition.

(I)

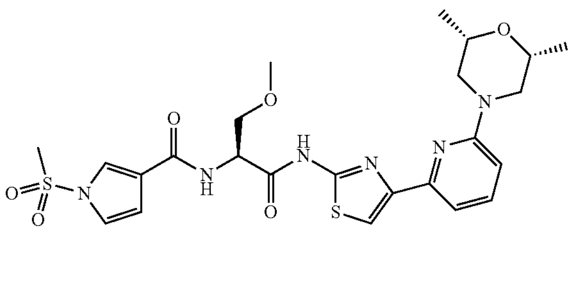

11 Claims, 40 Drawing Sheets

(56) References Cited

U.S. PATENT DOCUMENTS

| | | | |
|---|---|---|---|
| 7,205,103 | B2 | 4/2007 | Emerson |
| 7,232,566 | B2 | 6/2007 | June et al. |
| 7,348,326 | B2 | 3/2008 | DeSimone et al. |
| 7,572,631 | B2 | 8/2009 | Berenson et al. |
| 8,324,367 | B2 | 12/2012 | Kaemmerer et al. |
| 8,642,660 | B2 | 2/2014 | Goldfarb |
| 8,697,359 | B1 | 4/2014 | Zhang |
| 8,703,761 | B2 | 4/2014 | Forster et al. |
| 8,771,945 | B1 | 7/2014 | Zhang |
| 8,795,965 | B2 | 8/2014 | Zhang |
| 8,865,406 | B2 | 10/2014 | Zhang et al. |
| 8,945,861 | B2 | 2/2015 | Bomgarden et al. |
| 8,946,268 | B2 | 2/2015 | Lau et al. |
| 9,072,052 | B2 | 6/2015 | Griffin et al. |
| 9,126,985 | B2 | 9/2015 | Kley et al. |
| 9,353,051 | B2 | 5/2016 | Byrd et al. |
| 9,403,843 | B2 | 8/2016 | Thatcher et al. |
| 9,410,943 | B2 | 8/2016 | Kadoch et al. |
| 9,546,206 | B2 | 1/2017 | Ring et al. |
| 9,546,296 | B2 | 1/2017 | Wang et al. |
| 9,636,323 | B2 | 5/2017 | Lin et al. |
| 9,656,959 | B2 | 5/2017 | Ni et al. |
| 9,694,084 | B2 | 7/2017 | Bradner et al. |
| 9,708,338 | B2 | 7/2017 | Yukimasa et al. |
| 9,708,348 | B2 | 7/2017 | Castro et al. |
| 9,850,543 | B2 | 12/2017 | Jagani et al. |
| 9,919,998 | B2 | 3/2018 | Ebright et al. |
| 9,932,340 | B2 | 4/2018 | Dai et al. |
| 10,105,420 | B2 | 10/2018 | Kadoch et al. |
| 10,131,637 | B2 | 11/2018 | Abdel-Meguid et al. |
| 10,207,998 | B2 | 2/2019 | Derbyshire et al. |
| 10,239,888 | B2 | 3/2019 | Bradner et al. |
| 10,266,850 | B2 | 4/2019 | Doudna et al. |
| 10,308,614 | B2 | 6/2019 | Albrecht et al. |
| 10,464,925 | B2 | 11/2019 | Bradner et al. |
| 10,472,376 | B2 | 11/2019 | Yamamoto et al. |
| 10,646,575 | B2 | 5/2020 | Phillips et al. |
| 10,660,968 | B2 | 5/2020 | Phillips et al. |
| 10,669,253 | B2 | 6/2020 | Bradner et al. |
| 10,849,982 | B2 | 12/2020 | Phillips et al. |
| 10,905,768 | B1 | 2/2021 | Phillips et al. |
| 10,976,320 | B2 | 4/2021 | Dykhuizen et al. |
| 11,149,254 | B2 | 10/2021 | Szalay et al. |
| 11,419,859 | B2 | 8/2022 | Agresta |
| 11,485,732 | B2 | 11/2022 | Vaswani et al. |
| 11,497,752 | B2 | 11/2022 | Anthony et al. |
| 11,639,345 | B2 | 5/2023 | Bloch et al. |
| 11,773,085 | B2 | 10/2023 | Zhou et al. |
| 11,793,802 | B2 | 10/2023 | Bearss et al. |
| 11,851,445 | B2 | 12/2023 | Ruppel et al. |
| 11,865,114 | B2 | 1/2024 | Ramachandra et al. |
| 12,282,014 | B2 | 4/2025 | Kadoch et al. |
| 12,383,560 | B2 | 8/2025 | Anthony et al. |
| 12,441,726 | B2 | 10/2025 | Wilson et al. |
| 2002/0022018 | A1 | 2/2002 | Curiel et al. |
| 2002/0037281 | A1 | 3/2002 | Davidson et al. |
| 2002/0106632 | A1 | 8/2002 | Manfredi |
| 2003/0022375 | A1 | 1/2003 | Itoh et al. |
| 2003/0027335 | A1 | 2/2003 | Ruley et al. |
| 2004/0216178 | A1 | 10/2004 | Jones et al. |
| 2005/0079512 | A1 | 4/2005 | Emerson et al. |
| 2005/0130919 | A1 | 6/2005 | Xu et al. |
| 2006/0058255 | A1 | 3/2006 | Chen et al. |
| 2006/0121005 | A1 | 6/2006 | Berenson et al. |
| 2007/0105181 | A1 | 5/2007 | Pope et al. |
| 2008/0221157 | A1 | 9/2008 | Chakravarty et al. |
| 2009/0163545 | A1 | 6/2009 | Goldfarb |
| 2010/0048565 | A1 | 2/2010 | Frenkel et al. |
| 2010/0197621 | A1 | 8/2010 | Henry et al. |
| 2010/0284990 | A1 | 11/2010 | Kaemmerer et al. |
| 2011/0003809 | A1 | 1/2011 | Ahrendt |
| 2011/0230486 | A1 | 9/2011 | Lau et al. |
| 2012/0034867 | A1 | 2/2012 | Griffin et al. |
| 2012/0035244 | A1 | 2/2012 | Chinnaiyan et al. |
| 2012/0308484 | A1 | 12/2012 | Szalay et al. |
| 2013/0034867 | A1 | 2/2013 | Bomgarden et al. |
| 2014/0068797 | A1 | 3/2014 | Doudna et al. |
| 2014/0287931 | A1 | 9/2014 | Bernards et al. |
| 2015/0018315 | A1 | 1/2015 | Kley et al. |
| 2015/0057169 | A1 | 2/2015 | Siu et al. |
| 2015/0376139 | A1 | 12/2015 | Abdel-Meguid et al. |
| 2016/0032402 | A1 | 2/2016 | Jagani et al. |
| 2016/0130663 | A1 | 5/2016 | Kohno et al. |
| 2016/0176916 | A1 | 6/2016 | Bradner et al. |
| 2016/0200721 | A1 | 7/2016 | Yukimasa et al. |
| 2016/0347708 | A1 | 12/2016 | Ebright et al. |
| 2017/0174688 | A1 | 6/2017 | Dai et al. |
| 2018/0086720 | A1 | 3/2018 | Albrecht et al. |
| 2018/0105500 | A1 | 4/2018 | Derbyshire et al. |
| 2018/0140722 | A1 | 5/2018 | Willis et al. |
| 2018/0258491 | A1 | 9/2018 | Jagani et al. |
| 2018/0328913 | A1 | 11/2018 | Kadoch et al. |
| 2020/0069669 | A1 | 3/2020 | Grassian et al. |
| 2020/0206344 | A1 | 7/2020 | Kadoch et al. |
| 2020/0261434 | A1 | 8/2020 | Choe et al. |
| 2021/0009568 | A1 | 1/2021 | Zhou et al. |
| 2021/0038611 | A1 | 2/2021 | Anthony et al. |
| 2021/0171958 | A1 | 6/2021 | Chan et al. |
| 2021/0230154 | A1 | 7/2021 | Vaswani et al. |
| 2021/0230190 | A1 | 7/2021 | Ruppel et al. |
| 2021/0251988 | A1 | 8/2021 | Zhou et al. |
| 2021/0260171 | A1 | 8/2021 | Zhou et al. |
| 2021/0388040 | A1 | 12/2021 | Kadoch et al. |
| 2022/0016083 | A1 | 1/2022 | Centore et al. |
| 2022/0079940 | A1 | 3/2022 | Centore et al. |
| 2022/0098190 | A1 | 3/2022 | Ruppel et al. |
| 2022/0119378 | A1 | 4/2022 | Anthony et al. |
| 2022/0396604 | A1 | 12/2022 | Kadoch et al. |
| 2023/0035235 | A1 | 2/2023 | Kadoch et al. |
| 2023/0079819 | A1 | 3/2023 | Vaswani et al. |
| 2023/0121497 | A1 | 4/2023 | Vaswani et al. |
| 2023/0129003 | A1 | 4/2023 | Vaswani et al. |
| 2023/0138480 | A1 | 5/2023 | Anthony et al. |
| 2023/0149414 | A1 | 5/2023 | Anthony et al. |
| 2024/0101550 | A1 | 3/2024 | Vaswani et al. |
| 2024/0158387 | A1 | 5/2024 | Vaswani et al. |
| 2024/0189318 | A1 | 6/2024 | Huang |
| 2025/0241931 | A1 | 7/2025 | Reilly et al. |
| 2025/0325553 | A1 | 10/2025 | Schuck et al. |

FOREIGN PATENT DOCUMENTS

| | | | |
|---|---|---|---|
| CN | 107531668 | A | 1/2018 |
| EA | 202192101 | A1 | 12/2021 |
| EP | 0172096 | A1 | 2/1986 |
| JP | 2000-095767 | A | 4/2000 |
| JP | 2011-507910 | A | 3/2011 |
| WO | WO-94/10300 | A1 | 5/1994 |
| WO | WO-95/30761 | A2 | 11/1995 |
| WO | WO-2000/024392 | A1 | 5/2000 |
| WO | WO-00/59888 | A1 | 10/2000 |
| WO | WO-00/59905 | A1 | 10/2000 |
| WO | WO-2005/039643 | A2 | 5/2005 |
| WO | WO-2005/112620 | A2 | 12/2005 |
| WO | WO-2006/005941 | A1 | 1/2006 |
| WO | WO-2006/051063 | A1 | 5/2006 |
| WO | WO-2006/070806 | A1 | 7/2006 |
| WO | WO-2008/022396 | A1 | 2/2008 |
| WO | WO-2008/157500 | A1 | 12/2008 |
| WO | WO-2009/086303 | A2 | 7/2009 |
| WO | WO-2009/111277 | A1 | 9/2009 |
| WO | WO-2010/007046 | A2 | 1/2010 |
| WO | WO-2011/115998 | A2 | 9/2011 |
| WO | WO-2011/132175 | A2 | 10/2011 |
| WO | WO-2012/085650 | A1 | 6/2012 |
| WO | WO-2013/116663 | A1 | 8/2013 |
| WO | WO-2013/116682 | A1 | 8/2013 |
| WO | WO-2014/150395 | A1 | 9/2014 |
| WO | WO-2015/002230 | A1 | 1/2015 |
| WO | WO-2015/005473 | A1 | 1/2015 |
| WO | WO-2015/103317 | A1 | 7/2015 |
| WO | WO-2015/120320 | A1 | 8/2015 |
| WO | WO-2015/121688 | A1 | 8/2015 |
| WO | WO-2016/054491 | A1 | 4/2016 |

(56) References Cited

FOREIGN PATENT DOCUMENTS

| | | | |
|---|---|---|---|
| WO | WO-2016/138114 | A1 | 9/2016 |
| WO | WO-2016/160718 | A1 | 10/2016 |
| WO | WO-2016/207212 | A1 | 12/2016 |
| WO | WO-2017/024318 | A1 | 2/2017 |
| WO | WO-2017/060470 | A1 | 4/2017 |
| WO | WO-2017/087885 | A1 | 5/2017 |
| WO | WO-2017/118734 | A1 | 7/2017 |
| WO | WO-2017/158381 | A1 | 9/2017 |
| WO | WO-2018/148443 | A1 | 8/2018 |
| WO | WO-2018/160636 | A1 | 9/2018 |
| WO | WO-2018/175324 | A1 | 9/2018 |
| WO | WO-2019/038215 | A1 | 2/2019 |
| WO | WO-2019/040098 | A1 | 2/2019 |
| WO | WO-2019/138017 | A1 | 7/2019 |
| WO | WO-2019/142192 | A1 | 7/2019 |
| WO | WO-2019/152437 | A1 | 8/2019 |
| WO | WO-2019/152440 | A1 | 8/2019 |
| WO | WO-2019/226915 | A1 | 11/2019 |
| WO | WO-2020/035779 | A1 | 2/2020 |
| WO | WO-2020/081556 | A2 | 4/2020 |
| WO | WO-2020/081588 | A1 | 4/2020 |
| WO | WO-2020/106915 | A1 | 5/2020 |
| WO | WO-2020/127685 | A1 | 6/2020 |
| WO | WO-2020/160100 | A1 | 8/2020 |
| WO | WO-2020/160180 | A1 | 8/2020 |
| WO | WO-2021/081032 | A1 | 4/2021 |
| WO | WO-2021/155262 | A1 | 8/2021 |
| WO | WO-2021/155264 | A1 | 8/2021 |
| WO | WO-2021/155316 | A1 | 8/2021 |
| WO | WO-2021/155320 | A1 | 8/2021 |
| WO | WO-2021/155321 | A2 | 8/2021 |
| WO | WO-2021/183218 | A1 | 9/2021 |
| WO | WO-2021/236080 | A1 | 11/2021 |
| WO | WO-2022/192621 | A1 | 9/2022 |
| WO | WO-2022/198043 | A1 | 9/2022 |
| WO | WO-2023/009834 | A2 | 2/2023 |
| WO | WO-2023/196560 | A1 | 10/2023 |
| WO | WO-2023/196565 | A1 | 10/2023 |
| WO | WO-2023/196567 | A2 | 10/2023 |
| WO | WO-2024/024428 | A1 | 2/2024 |
| WO | WO-2024/031875 | A1 | 2/2024 |
| WO | WO-2024/086577 | A1 | 4/2024 |
| WO | WO-2024/216136 | A1 | 10/2024 |
| WO | WO-2024/216151 | A1 | 10/2024 |
| WO | WO-2024/249769 | A2 | 12/2024 |
| WO | WO-2025/080767 | A1 | 4/2025 |
| WO | WO-2025/080769 | A1 | 4/2025 |

OTHER PUBLICATIONS

Adamo et al., "The oncogene ERG: a key factor in prostate cancer," Oncogene 35(4):403-14 (Jan. 28, 2016).

Advani et al., "A Phase 1 study of imatinib mesylate in combination with cytarabine and daunorubicin for c-kit positive relapsed acute myeloid leukemia," Leuk Res. 34(12):1622-6 (Dec. 2010).

Alazawi, "Foghorn Therapeutics," Blackseed Bio, last updated Mar. 4, 2022, retrieved Jul. 24, 2023, from <https://blackseedbio.com/reports/fhtx#pipeline> (26 pages).

Anders et al., "HTSeq—a Python framework to work with high-throughput sequencing data," Bioinformatics 31(2):166-9 (Jan. 1, 20155).

Asangani et al., "Therapeutic targeting of BET bromodomain proteins in castration-resistant prostate cancer," available in PMC Dec. 12, 2014. Published in final edited form as: Nature. 510(7504):278-82 (2014) (44 pages).

Attard et al., "Duplication of the fusion of TMPRSS2 to ERG sequences identifies fatal human prostate cancer," available in PMC Feb. 24, 2009. Published in final edited form as: Oncogene. 27(3):253-63 (2008) (19 pages).

Basuyaux et al., "The Ets transcription factors interact with each other and with the c-Fos/c-Jun complex via distinct protein domains in a DNA-dependent and -independent manner," J Biol Chem. 272(42):26188-95 (1997).

Bendall et al., "Prevention of amino acid conversion in SILAC experiments with embryonic stem cells," Mol Cell Proteomics. 7(9):1587-97 (2008).

Berger et al., "Androgen-induced differentiation and tumorigenicity of human prostate epithelial cells," Cancer Res. 64(24):8867-75 (2004).

Börno et al., "Genome-wide DNA methylation events in TMPRSS2-ERG fusion-negative prostate cancers implicate an EZH2-dependent mechanism with miR-26a hypermethylation," Cancer Discov. 2(11):1024-35 (2012).

Camuzeaux et al., "Imaging Erg and Jun transcription factor interaction in living cells using fluorescence resonance energy transfer analyses," Biochem Biophys Res Commun. 332(4):1107-14 (2005).

Cancer Genome Atlas Research Network, "The Molecular Taxonomy of Primary Prostate Cancer," Cell. 163(4):1011-25 (2015) (16 pages).

Carell et al., "A novel procedure for the synthesis of libraries containing small organic molecules," Angew Chem Int Ed Engl. 33(20):2059-2061 (1994).

Carell et al., "A Solution-Phase Screening Procedure for the Isolation of Active Compounds from a Library of Molecules," Angewandte Chemie International Edition in English. 33(20): 2061-2064 (1994).

Centore et al., "Abstract 1224: Discovery of novel BAF inhibitors for the treatment of transcription factor-driven cancers," Poster Presentations—Proffered abstracts, Cancer Research 81(13_Supplement):1224 (Jul. 1, 2021) (2 pages).

Chen et al., "ETS factors reprogram the androgen receptor cistrome and prime prostate tumorigenesis in response to PTEN loss," available in PMC Feb. 1, 2014. Published in final edited form as: Nat Med. 19(8):1023-9 (2013) (21 pages).

Chng et al., "A transcriptional repressor co-regulatory network governing androgen response in prostate cancers," EMBO J. 31(12):2810-23 (2012).

Cho et al., "An unnatural biopolymer," Science. 261(5126):1303-1305 (1993).

Coban et al., "Synthesis, biological activity screening and molecular modeling study of acylaminoacetamide derivatives," Med Chem Res. 24(10):3710-29 (Jul. 25, 2015).

Cull et al., "Screening for receptor ligands using large libraries of peptides linked to the C terminus of the lac repressor," Proc Natl Acad Sci. 89(5): 1865-1869. (1992).

Cwirla et al., "Peptides on phage: A vast library of peptides for identifying ligands," Proc Nati Acad Sci. 87:6378-6382 (1990).

Database Registry, RN 1004932-80-2, entered Feb. 21, 2008 (1 page).

Database Registry, RN 1175782-23-6, entered Aug. 26, 2009 (1 page).

Database Registry, RN 1315743-98-6, entered Aug. 11, 2011 (1 page).

Database Registry, RN 878254-76-3, entered Mar. 28, 2006 (1 page).

Delattre et al., "Gene fusion with an ETS DNA-binding domain caused by chromosome translocation in human tumours," Nature. 359(6391):162-5 (1992).

Devlin et al., "Random Peptide Libraries: a Source of Specific Protein Binding Molecules," Science. 249(4967):404-406 (1990).

DeWitt et al., "'Diversomers'": an approach to nonpeptide, nonoligomeric chemical diversity, Proc Natl Acad Sci. 90(15):6909-6913 (1993).

Dobin et al., "STAR: ultrafast universal RNA-seq aligner," Bioinformatics. 29(1):15-21 (2013).

Dominguez et al. "Beyond editing: Repurposing CRISPR-Cas9 for Precision Genome Regulation and Interrogation," available in PMC Jun. 27, 2016, published in final edited form as: Nat Rev Mol Cell Biol. 17(1):5-15 (Jan. 2016) (24 pages).

Donaldson et al., "Solution structure of the ETS domain from murine Ets-1: a winged helix-turn-helix DNA binding motif," EMBO J. 15(1):125-34 (1996).

Decor et al., "Design, synthesis and biological evaluation of novel aminothiazoles as antiviral compounds acting against human rhinovirus," Bioorg Med Chem Lett. 23(13):3841-7 (Jul. 1, 2013).

Erb et al., "Recursive deconvolution of combinatorial chemical libraries," Proc Natl Acad Sci. 91(24):11422-11426 (1994).

(56) References Cited

OTHER PUBLICATIONS

Extended European Search Report for European Application No. 19748410.8, dated Sep. 24, 2021 (10 pages).
Extended European Search Report for European Application No. 19887386.1, dated Dec. 5, 2022 (18 pages).
Extended European Search Report for European Application No. 20749261.2, dated Oct. 18, 2022 (8 pages).
Extended European Search Report for European Application No. 21748261.1, dated Jan. 29, 2024 (17 pages).
Fathi et al., "Differentiation syndrome with lower-intensity treatments for acute myeloid leukemia," Am J Hematol. 96(6):735-46 (Jun. 1, 2021) (13 Pages).
Felici et al., "Selection of antibody ligands from a large library of oligopeptides expressed on a multivalent exposition vector," J Mol Biol. 222(2):301-10 (1991).
Feng et al., "GFOLD: a generalized fold change for ranking differentially expressed genes from RNA-seq data," Bioinformatics. 28(21):2782-8 (2012).
Fodor et al., "Multiplexed biochemical assays with biological chips," Nature. 364:555-556 (1993).
Gaj et al. "ZFN, TALEN and CRISPR/Cas-based Methods for Genome Engineering," available in PMC Jul. 1, 2014, published in final edited form as: Trends Biotechnol. 31(7):397-405 (Jul. 2013) (20 pages).
Gallop et al., "Applications of Combinatorial Technologies to Drug Discovery. 1. Background and Peptide Combinatorial Libraries," J Med Chem 37(9):1233-51 (1994).
Gene Ontology Consortium, "Gene Ontology Consortium: going forward," Nucleic Acids Res. 43(Database issue):D1049-56 (2015).
Gingras et al., "Advances in protein complex analysis using mass spectrometry," J Physiol. 563(Pt 1):11-21 (Feb. 15, 2005).
Godwin et al., "Gemtuzumab ozogamicin in acute myeloid leukemia," Leukemia 31(9):1855-68 (Sep. 2017).
Helgeson et al., "Characterization of TMPRSS2:ETV5 and SLC45A3:ETV5 gene fusions in prostate cancer," Cancer Res. 68(1):73-80 (2008).
Ho et al., "An embryonic stem cell chromatin remodeling complex, esBAF, is essential for embryonic stem cell self-renewal and pluripotency," Proc Natl Acad Sci U S A. 106(13):5181-6 (2009).
Houghten et al., "The use of synthetic peptide combinatorial libraries for the identification of bioactive peptides," Biotechniques. 13(3):412-21 (1992).
Ichikawa et al., "An RNA-binding protein gene, TLS/FUS, is fused to ERG in human myeloid leukemia with t(16;21) chromosomal translocation," Cancer Res. 54(11):2865-8 (1994).
International Preliminary Report on Patentability for International Application No. PCT/US2016/062911 issued May 22, 2018 (13 pages).
International Preliminary Report on Patentability for International Application No. PCT/US2019/015722, issued Aug. 4, 2020 (6 pages).
International Preliminary Report on Patentability for International Application No. PCT/US2020/033829, issued Nov. 17, 2022 (6 pages).
International Search Report and Written Opinion for International Application No. PCT/US19/15722, mailed May 31, 2019 (12 pages).
International Search Report and Written Opinion for International Application No. PCT/US2016/062911 dated Mar. 3, 2017 (16 pages).
International Search Report and Written Opinion for International Application No. PCT/US2020/015605, mailed Jun. 16, 2020 (15 pages).
International Search Report and Written Opinion for International Application No. PCT/US2020/015723, mailed Jul. 2, 2020 (15 pages).
International Search Report and Written Opinion for International Application No. PCT/US2020/033829, mailed Aug. 17, 2020 (14 pages).
International Search Report and Written Opinion for International Application No. PCT/US2022/019506, dated Jun. 7, 2022 (9 pages).
International Search Report and Written Opinion for International Application No. PCT/US2023/017839, mailed Sep. 6, 2023 (11 pages).
International Search Report and Written Opinion for International Application No. PCT/US2023/077088, mailed Mar. 4, 2024 (17 pages).
International Search Report and Written Opinion for International Application No. PCT/US21/15876, mailed on Apr. 7, 2021 (23 pages).
International Search Report and Written Opinion for International Application No. PCT/US21/15878, dated Jun. 4, 2021 (10 pages).
International Search Report and Written Opinion for International Application No. PCT/US23/17821, mailed Jun. 30, 2023 (9 pages).
International Search Report and Written Opinion for International Application No. PCT/US23/17829, mailed Aug. 23, 2023 (15 pages).
International Search Report and Written Opinion for International Patent Application No. PCT/US2019/062525, mailed Feb. 18, 2020 (14 pages).
International Search Report and Written Opinion for PCT/US2022/020943, dated Jun. 14, 2022 (17 pages).
Jones et al., "A novel series of potent and selective ketone histone deacetylase inhibitors with antitumor activity in vivo," J Med Chem. 51(8):2350-3 (Apr. 24, 2008).
Karim et al., "The ETS-domain: a new DNA-binding motif that recognizes a purine-rich core DNA sequence," Genes Dev. 4(9):1451-3 (1990).
Klezovitch et al., "A causal role for ERG in neoplastic transformation of prostate epithelium," Proc Natl Acad Sci U S A. 105(6):2105-10 (2008).
Kumar-Sinha et al., "Recurrent gene fusions in prostate cancer," available in PMC Jul. 16, 2009. Published in final edited form as: Nat Rev Cancer. 8(7):497-511 (2008) (29 pages).
Kunderfranco et al., "ETS transcription factors control transcription of EZH2 and epigenetic silencing of the tumor suppressor gene Nkx3.1 in prostate cancer," PLoS One. 5(5):e10547 (2010) (17 pages).
Lam et al., "A new type of synthetic peptide library for identifying ligand-binding activity," Nature. 354(6348):82-84 (1991).
Lam, "Application of combinatorial library methods in cancer research and drug discovery," Anticancer Drug Des. 12(3):145-67 (1997).
Langmead et al., "Fast gapped-read alignment with Bowtie 2," available in PMC Apr. 1, 2013. Published in final edited form as: Nat Methods. 9(4):357-9 (2012) (8 pages).
Link et al., "Targeting the BAF57 SWI/SNF subunit in prostate cancer: a novel platform to control androgen receptor activity," Cancer Res. 68(12):4551-8 (2008).
Love et al., "Moderated estimation of fold change and dispersion for RNA-seq data with DESeq2," Genome Biol. 15(12):550 (2014) (21 pages).
Lupien et al., "FoxA1 translates epigenetic signatures into enhancer-driven lineage-specific transcription," Cell. 132(6):958-70 (2008).
Machanick et al., "MEME-ChIP: motif analysis of large DNA datasets," Bioinformatics. 27(12):1696-7 (2011).
Mackereth et al., "Diversity in structure and function of the Ets family PNT domains," J Mol Biol. 342(4):1249-64 (2004).
Madura et al., "N-recognin/Ubc2 interactions in the N-end rule pathway," J Biol Chem. 268(16):12046-54 (1993).
McBride et al., "Disruption of mammalian SWI/SNF and polycomb complexes in human sarcomas: mechanisms and therapeutic opportunities," J Pathol. 244(5): 638-649 (Apr. 2018).
Meléet al., "The human transcriptome across tissues and individuals," available in PMC Aug. 24, 2015. Published in final edited form as: Science. 348(6235):660-5 (2015) (12 pages).
Mill et al., "RUNX1-targeted therapy for AML expressing somatic or germline mutation in RUNX1," Blood 134(1):59-73 (Jul. 4, 2019).
Mounir et al., "ERG signaling in prostate cancer is driven through PRMT5-dependent methylation of the Androgen Receptor," Elife. 5:e13964 (2016) (19 pages).

(56) References Cited

OTHER PUBLICATIONS

Nagaich et al., "Rapid periodic binding and displacement of the glucocorticoid receptor during chromatin remodeling," Mol Cell. 14(2):163-74 (2004).
Nam et al., "Expression of the TMPRSS2: Erg fusion gene predicts cancer recurrence after surgery for localised prostate cancer," Br J Cancer. 97(12):1690-5 (2007).
Office Action for Chinese Patent Application No. 201980023925.9, dated Apr. 20, 2022 (13 pages).
Ong et al., "A practical recipe for stable isotope labeling by amino acids in cell culture (SILAC)," Nat Protoc. 1(6):2650-60 (2006).
Papillon et al., "Discovery of Orally Active Inhibitors of Brahma Homolog (BRM)/SMARCA2 ATPase Activity for the Treatment of Brahma Related Gene 1 (BRG1)/SMARCA4-Mutant Cancers," J Med Chem. 61(22):10155-72 (Nov. 2018).
Partial Supplementary European Search Report for European Patent Application No. 19887386.1, dated Jul. 20, 2022 (23 pages).
Partial Supplementary European Search Report for European Patent Application No. 20936213.6, dated Feb. 8, 2024 (20 pages).
Paulo et al., "FLI1 is a novel ETS transcription factor involved in gene fusions in prostate cancer," Genes Chromosomes Cancer. 51(3):240-9 (2012).
Pescatore et al., "Optimization of a series of potent and selective ketone histone deacetylase inhibitors," Bioorg Med Chem Lett. 18(20):5528-32 (Oct. 15, 2008).
Petrovics et al., "Frequent overexpression of ETS-related gene-1 (ERG1) in prostate cancer transcriptome," Oncogene. 24(23):3847-52 (2005).
Pomerantz et al., "The androgen receptor cistrome is extensively reprogrammed in human prostate tumorigenesis," available in PMC May 1, 2016. Published in final edited form as: Nat Genet. 47(11):1346-51 (2015) (17 pages).
Prensner et al., "The long noncoding RNA SChLAP1 promotes aggressive prostate cancer and antagonizes the SWI/SNF complex," available in PMC May 1, 2014. Published in final edited form as: Nat Genet. 45(11):1392-8 (2013) (26 pages).
PubChem CID 117640569, "N-[2-[[4-(4-Methoxyphenyl)-1,3-thiazol-2-yl]amino]-2-oxoethyl]-1,3-thiazole-5-carboxamide," https://pubchem.ncbi.nlm.nih.gov/compound/117640569, created Feb. 23, 2016 (9 pages).
PubChem CID 56442706, "1-(4-Methoxyphenyl)-N-[2-oxo-2-[4-(1,2,4-triazol-1-yl) anilino]ethyl]pyrazole-3-carboxamide," https://pubchem.ncbi.nlm.nih.gov/compound/56442706, created Jan. 25, 2012 (8 pages).
PubChem CID 91946137, "N-[2-[(1-Ethylpyrazol-3-yl}amino]-2-oxoethyl]-1-methylpyrazole-3-carboxamide," https://pubchem.ncbi.nlm.nih.gov/compound/91946137, created Oct. 22, 2015 (8 pages).
PubChem Compound Summary for CID 155037309, dated Dec. 19, 2020 (9 pages).
PubChem Compound Summary for CID No. 136572628, "4-Chloro-N-[2-(cyclopentylamino)-2-oxoethyl]-5-nitro-1H-pyrazole-3-carboxamide," created Jan. 24, 2019, <https://pubchem.ncbi.nlm.nih.gov/compound/136572628>, (7 pages).
PubChem Compound Summary for CID No. 49726797, "N-Methyl-N-(2-oxo-2-((4-(pyridin-3-yl) thiazol-2-yl)amino)ethyl)-1H-indole-3-carboxamide," created Nov. 27, 2010, <https://pubchem.ncbi.nlm.nih.gov/compound/49726797>, (8 pages).
PubChem Compound Summary for CID No. 91945707, "N-[2-[(4,5-Dimethyl-1,3-thiazol-2-yl)amino]-2-oxoethyl]-1-methylpyrazole-3-carboxamide," created Oct. 22, 2015 <https://pubchem.ncbi.nlm.nih.gov/compound/91945707>, (8 pages).
PubChem Compound Summary for PubChem CID 49726798, "N-(2-((4-(Furan-2-yl)thiazol-2-yl)amino)-2-oxoethyl)-N-methyl-1H-indole-3-carboxamide," created Nov. 27, 2010 <https://pubchem.ncbi.nih.gov/compound/49726798> (8 pages).
PubChem Compound Summary for SID 172131678, dated Dec. 9, 2014 (8 pages).
PubChem, "Compound Summary for CID 108452511," <https://pubchem.ncbi.nlm.nih.gov/compound/108452511>, created Jan. 15, 2016, retrieved Jan. 4, 2021 (7 pages).
PubChem, "Compound Summary for CID 2955118," <https://pubchem.ncbi.nlm.nih.gov/compound/2955118>, created Jul. 29, 2005, retrieved Mar. 22, 2017 (13 pages).
PubChem, "Compound Summary for CID 7325930," <https://pubchem.ncbi.nlm.nih.gov/compound/7325930>, created Jul. 29, 2006, retrieved Mar. 22, 2017 (11 pages).
PubChem, "Compound Summary for CID 970466," <https://pubchem.ncbi.nlm.nih.gov/compound/970466>, created Jul. 9, 2005, retrieved Mar. 22, 2017 (11 pages).
Quinlan et al., "BEDTools: a flexible suite of utilities for comparing genomic features," Bioinformatics. 26(6):841-2 (2010).
Rajput et al., "Frequency of the TMPRSS2:ERG gene fusion is increased in moderate to poorly differentiated prostate cancers," J Clin Pathol. 60(11):1238-43 (2007).
Rappsilber et al., "Protocol for micro-purification, enrichment, pre-fractionation and storage of peptides for proteomics using StageTips," Nat Protoc. 2(8):1896-906 (2007).
Schiefer et al., "Design, synthesis, and optimization of novel epoxide incorporating peptidomimetics as selective calpain inhibitors," J Med Chem. 56(15):6054-68 (Aug. 8, 2013).
Scott et al., "Searching for peptide ligands with an epitope library," Science. 249(4967):386-390 (1990).
Shen et al., "The SWI/SNF ATPase Brm is a gatekeeper of proliferative control in prostate cancer," Cancer Res. 68(24):10154-62 (Dec. 2008).
Shi et al., "Role of SWI/SNF in acute leukemia maintenance and enhancer-mediated Myc regulation," Genes Dev. 27(24):2648-62 (Dec. 2013).
Siegel et al., "Cancer statistics, 2015," CA Cancer J Clin. 65(1):5-29 (2015).
Spickler et al., "Phosphatidylinositol 4-kinase III beta is essential for replication of human rhinovirus and its inhibition causes a lethal phenotype in vivo," Antimicrob Agents Chemother. 57(7):3358-68 (Jul. 2013).
STN Registry Database, RN 1010893-05-6, entered Mar. 30, 2008 (2 pages).
STN Registry Database, RN 1049271-26-2, entered Sep. 14, 2008 (2 pages).
STN Registry Database, RN 1081662-32-9, entered Dec. 8, 2008 (2 pages).
STN Registry Database, RN 1209112-42-4, entered Mar. 12, 2010 (2 pages).
STN Registry Database, RN 1246047-75-5, entered Oct. 12, 2010 (2 pages).
STN Registry Database, RN 1308280-67-2, entered Jun. 9, 2011 (2 pages).
STN Registry Database, RN 1351682-19-3, entered Dec. 22, 2011 (2 pages).
STN Registry Database, RN 1401558-47-1, entered Oct. 22, 2012 (2 pages).
STN Registry Database, RN 1455783-72-8, entered Oct. 6, 2013 (2 pages).
STN Registry Database, RN 1576383-94-2, entered Mar. 31, 2014 (2 pages).
STN Registry Database, RN 1586193-45-4, entered Apr. 17, 2014 (2 pages).
STN Registry Database, RN 1827759-12-5, entered Dec. 13, 2015 (2 pages).
STN Registry Database, RN 1831899-24-1, entered Dec. 17, 2015 (2 pages).
STN Registry Database, RN 1839545-15-1, entered Dec. 31, 2015 (2 pages).
STN Registry Database, RN 923768-18-7, entered Feb. 28, 2007 (2 pages).
STN Registry Database, RN 923809-79-4, entered Feb. 28, 2007 (2 pages).
STN Registry Database, RN 931893-54-8, entered Apr. 23, 2007 (2 pages).
STN Registry Database, RN 932130-00-2, entered Apr. 24, 2007 (2 pages).
STN Registry Database, RN 938283-11-5, entered Jun. 22, 2007 (2 pages).

(56) References Cited

OTHER PUBLICATIONS

Subramanian et al., "Gene set enrichment analysis: a knowledge-based approach for interpreting genome-wide expression profiles," Proc Natl Acad Sci USA. 102(43):15545-50 (2005).
Sun et al., "TMPRSS2-ERG fusion, a common genomic alteration in prostate cancer activates C-MYC and abrogates prostate epithelial differentiation," available in PMC Oct. 4, 2020. Published in final edited form as: Oncogene. 27(40)5348-53 (2008) (12 pages).
Tikdari et al., "Reaction of 2-Aminothiazoles with 5-Oxazolones," ChemInform. 18(47):Abstract 199 (1987) (1 page).
Tikdari et al., "Reaction of 2-Aminothiazoles with 5-Oxazolones," Indian Journal of Chemistry 26B:478-9 (May 1987).
Tomlins et al., "Recurrent fusion of TMPRSS2 and ETS transcription factor genes in prostate cancer," Science.310(5748):644-8 (2005).
Tomlins et al., "Role of the TMPRSS2-ERG gene fusion in prostate cancer," Neoplasia. 10(2):177-88 (2008) (21 pages).
Tomlins et al., "TMPRSS2:ETV4 gene fusions define a third molecular subtype of prostate cancer," Cancer Res. 66(7):3396-400 (2006).
Triandafillidi et al., "tert-Butyl ester or benzylamide of the dipeptide Pro-Gly as organocatalysts for the asymmetric aldol reaction," Tetrahedron 71:932-40 (2015).
Tsai et al. "Dimeric CRISPR RNA-guided FokI Nucleases for Highly Specific Genome Editing," available in PMC Dec. 1, 2014, published in final edited form as: Nat Biotechnol. 32(6):569-576 (Jun. 2014) (22 pages).
Tuoc et al., "Chromatin regulation by BAF170 controls cerebral cortical size and thickness," Dev Cell. 25(3):256-69 (May 2013).
Vachtenheim et al., "SWI/SNF chromatin remodeling complex is critical for the expression of microphthalmia-associated transcription factor in melanoma cells," Biochemical and Biophysical Research Communications. 392(3):454-459 (2010).
Varambally et al., "The polycomb group protein EZH2 is involved in progression of prostate cancer," Nature. 419(6907):624-9 (2002).
Vela et al., "Discovery of Enhancers of the Secretion of Leukemia Inhibitory Factor for the Treatment of Multiple Sclerosis," J Biomol Screen. 21(5):437-45 (Jun. 2016).
Verger et al., "Identification of amino acid residues in the ETS transcription factor Erg that mediate Erg-Jun/Fos-DNA ternary complex formation," J Biol Chem. 276(20):17181-9 (2001).
Wahedy et al., "Facile Synthesis and In-Vitro Antimicrobial Activity of Some Novel 2-Hetroamido-5-Amino Benzimidazoles," Am J PharmTech Res. 3(2):868-82 (2013).
Wollenick et al., "Synthetic transactivation screening reveals ETV4 as broad coactivator of hypoxia-inducible factor signaling," Nucleic Acids Res. 40(5):1928-43 (2012).
Yang et al., "EZH2, an epigenetic driver of prostate cancer," Protein Cell. 4(5):331-41 (2013).
Yildirim et al., "Mbd3/NURD complex regulates expression of 5-hydroxymethylcytosine marked genes in embryonic stem cells," Cell. 147(7):1498-510 (2011).
Yu et al., "An integrated network of androgen receptor, polycomb, and TMPRSS2-ERG gene fusions in prostate cancer progression," Cancer Cell. 17(5):443-54 (2010).
Yu et al., "Direct recruitment of polycomb repressive complex 1 to chromatin by core binding transcription factors," Mol Cell. 45(3):330-43 (2012).
Zervos et al., "Mxi1, a protein that specifically interacts with Max to bind Myc-Max recognition sites," Cell. 72(2):223-32 (1993).
Zhang et al., "Discovery of novel dual-action antidiabetic agents that inhibit glycogen phosphorylase and activate glucokinase," Eur J Med Chem. 58:624-39 (Dec. 2012).
Zhang et al., "Model-based analysis of ChIP-Seq (MACS)," Genome Biol. 9(9):R137 (2008) (9 pages).
Zong et al., "ETS family transcription factors collaborate with alternative signaling pathways to induce carcinoma from adult murine prostate cells," Proc Natl Acad Sci U S A. 106(30):12465-70 (Jul. 2009).
Zuckermann et al., "Discovery of Nanomolar Ligands for 7-Transmembrane G-Protein-Coupled Receptors from a Diverse N-(Substituted)glycine Peptoid Library," J Med Chem. 37(17):2678-2685 (1994).
Zvarec et al., "5-Benzylidenerhodanine and 5-benzylidene-2-4-thiazolidinedione based antibacterials," Bioorg Med Chem Lett. 22(8):2720-2 (2012).
International Preliminary Report on Patentability for International Application No. PCT/US2022/019506, issued Sep. 12, 2023 (6 pages).
U.S. Appl. No. 18/855,015, filed Oct. 8, 2024, Schuck et al.
U.S. Appl. No. 19/121,614, filed Apr. 16, 2025, Wan et al.
U.S. Appl. No. 19/474,359, filed Oct. 10, 2025, Adam et al.
"Compound Summary: N-[(S)-1-[[4-[6-[(2R,6S)-2,6-Dimethylmorpholino]-2-pyridyl]-2-thiazolyl]amino]-3-methoxy-1-oxo-2-propyl]-1-(methylsulfonyl)-1H-pyrrole-3-carboxamide," PubChem. CID: 156818027, <https://pubchem.ncbi.nlm.nih.gov/compound/156818027>, created Nov. 10, 2021, accessed Jan. 19, 2025 (9 pages).
"FLI1 gene," MedlinePlus, published May 1, 2012, <https://medlineplus.gov/genetics/> (3 pages).
"Form S-1 Registration Statement: Foghorn Therapeutics Inc.," as filed with the United States Securities and Exchange Commission on Oct. 2, 2020 (230 pages).
Adam et al., International Application No. PCT/US2024/024407, filed Apr. 12, 2024 by applicant Foghorn Therapeutics Inc. (42 pages).
Adam et al., International Application No. PCT/US2024/024428, filed Apr. 12, 2024 by applicant Foghorn Therapeutics Inc. (40 pages).
Adam et al., International Application No. PCT/US25/51009, filed by Foghorn Therapeutics Inc. (65 pages).
Boulay et al., "Cancer-Specific Retargeting of BAF Complexes by a Prion-like Domain," Cell 171(1):163-78 (Sep. 21, 2017) (36 pages).
Caira, Mino R. "Crystalline polymorphism of organic compounds." Design of Organic Solids (1998): 163-208 (46 pages).
CAS RN: 1212404-62-0; 2010. C18H17N3O4.
CAS RN: 1223164-86-0; STN entry date: May 14, 2010; N-[2-[[4-(3-Fluoro-4-methoxyphenyl)-2-thiazolyl]amino]-2-oxoethyl]-2-methyl-3-furancarboxamide (1page).
CAS RN: 1300403-14-8; STN entry date May 25, 2011; 5-Methyl-N-[2-oxo-2-[ (5-phenyl-2-pyridinyl)amino]ethyl]-2-thiophenecarboxamide (1 page).
CAS RN: 1644411-35-7; 2015. C24H32ClN8O4.
CAS RN: 924410-17-3; STN entry date: Mar. 2, 2007; 5-Methyl-N-[2-oxo-2-[ (4-phenyl-2-thiazolyl)amino]ethyl]-2-thiophenecarboxamide (1 page).
CAS RN: 924420-04-2; STN entry date: Mar. 2, 2007; 5-Methyl-N-[2-oxo-2-[[4-(4-pyridinyl)-2-thiazolyl]amino]ethyl]-2-thiophenecarboxamide (1 page).
CAS, "FHD-286 CAS registration information," dated Feb. 19, 2025 (6 pages).
Chandler et al., "ARID1a-DNA interactions are required for promoter occupancy by SWI/SNF," Mol Cell Biol. 33(2):265-80 (Jan. 2013).
Chattopahdyay et al., "Uveal melanoma: From diagnosis to treatment and the science in between," Cancer. 122(15):2299-2312 (26 pages) (Aug. 2016).
Collins et al., "Abstract 2122: The dual BRM/BRG1 (SMARCA2/4) inhibitor FHD-286 induces differentiation in preclinical models of AML," Cancer Res. 83(7_Supplement) (Apr. 2023) (5 pages).
Danziger et al., Automated site-directed drug design: a general algorithm for knowledge acquisition about hydrogen-bonding regions at protein surfaces, Proc R Soc Lond B Biol Sci. 236(1283): 101-113 (Mar. 1989) (14 pages).
Database Registry, RN 1323331-37-8, entered Aug. 25, 2011 (1 page).
Database Registry, RN 1323542-96-6, entered Aug. 26, 2011 (1 page).
Database Registry, RN 1324163-01-0, entered Aug. 28, 2011 (1 page).

(56) References Cited

OTHER PUBLICATIONS

Database Registry, RN 1327304-26-6, entered Sep. 2, 2011 (1 page).
Fadul et al., "EWS/FLI utilizes NKX2-2 to repress mesenchymal features of Ewing sarcoma," Genes Cancer 6(3-4):129-43 (Mar. 2015).
Fiskus et al., "Pre-Clinical Efficacy of Targeting Baf Complexes through Inhibition of the Dual Atpases BRG1 and BRM By FHD-286 in Cellular Models of AML of Diverse Genetic Background," Blood. 140(Supplement 1):8819-20 (Nov. 2022) (15 pages).
Grohar et al., "Ecteinascidin 743 interferes with the activity of EWS-FLI1 in Ewing sarcoma cells," Neoplasia 13(2):145-53 (Feb. 2011).
Hentemann, "Abstract ND14: Pharmacological profile and anti-tumor properties of FHD-286: A novel BAF inhibitor for the treatment of transcription factor-driven cancers," Cancer Res. 82(12_Supplement): ND14 (Jun. 2022) (4 pages).
Herrero-Martin et al., "Stable interference of EWS-FLI1 in an Ewing sarcoma cell line impairs IGF-1/IGF-1R signalling and reveals TOPK as a new target," Br J Cancer 101(1):80-90 (Jul. 7, 2009).
Hohmann et al., "Sensitivity and engineered resistance of myeloid leukemia cells to BRD9 inhibition," Nat Chem Biol. 12(9): 672-679 (Sep. 2016) (12 pages).
Kedage et al., "An Interaction with Ewing's Sarcoma Breakpoint Protein EWS Defines a Specific Oncogenic Mechanism of ETS Factors Rearranged in Prostate Cancer," Cell Rep. 17(5):1289-301 (Oct. 25, 2016) (14 pages).
Kumar et al., "Diazanaphthalen-3-yl carboxamides as inhibitors of proteins of the Wnt pathway and their preparation," Database CAPLUS. (Jan. 2019) (12 pages).
Michel et al., "Abstract PR15: BRD9 defines a novel mammalian SWI/SNF (BAF) complex configuration which supports proliferation in AML," Clin Cancer Res. 23(24_Suppl) Abstract PR15 (2017) (4 pages).
Piel et al., International Application No. PCT/US2024/031875, filed May 31, 2024 by applicant Foghorn Therapeutics Inc. (47 pages).
Piel et al., International Application No. PCT/US2024/050660, filed Oct. 10, 2024 by applicant Foghorn Therapeutics Inc. (35 pages).
PubChem CID 110712084, N-[(1-cyclopropylbenzimidazol-2-yl)methyl]furan-2-carboxamide. National Center for Biotechnology Information (2025). Retrieved Sep. 4, 2025 from https://pubchem.ncbi.nlm.nih.gov/compound/110712084, (8 pages).
PubChem CID 60478710, 5-nitro-N-(1-phenylbenzimidazol-2-yl)furan-2-carboxamide. National Center for Biotechnology Information (2025). Retrieved Sep. 4, 2025 from https://pubchem.ncbi.nlm.nih.gov/compound/60478710, (8 pages).
Rago et al., "Exquisite Sensitivity to Dual BRG1/BRM ATPase Inhibitors Reveals Broad SWI/SNF Dependencies in Acute Myeloid Leukemia," Mol Cancer Res. 20(3):361-72 (Mar. 1, 2022).
Ramos et al., "Current Approaches in the Treatment of Relapsed and Refractory Acute Myeloid Leukemia," J Clin Med. 4(4):665-95 (Apr. 2015).
Riggi et al., "EWS-FLI1 utilizes divergent chromatin remodeling mechanisms to directly activate or repress enhancer elements in Ewing sarcoma," Cancer Cell 26(5):668-81 (Nov. 10, 2014) (28 pages).
Sankar et al., "Promiscuous partnerships in Ewing's sarcoma," Cancer Genet. 204(7):351-65 (Jul. 2011) (28 pages).
Selleck Chemicals, "Safety Data Sheet: FHD-286," <https://www.selleckchem.com/msds/MSDS_E1178.pdf>, entry date Jan. 1, 2025 (2 pages).
Simone, Part XIV: Oncology: Introduction, Textbook of Medicine, Bennett et al., 20(1), 1004-1010 (1997) (8 pages).
STN Registry Database, CAS RN 858073-83-3, Albany Molecular Research, Inc., entered Aug. 3, 2005 (1 page).
Takigami et al., "Synthetic siRNA targeting the breakpoint of EWS/Fli-1 inhibits growth of Ewing sarcoma xenografts in a mouse model," Int J Cancer 128(1):216-26 (Jan. 1, 2011).
Wan et al., International Application No. PCT/US2024/050665, filed Oct. 10, 2024 by applicant Foghorn Therapeutics Inc. (112 pages).
Wu et al., "Targeting the chromatin remodeling enzyme BRG1 increases the efficacy of chemotherapy drugs in breast cancer cells," Oncotarget 7(19):27158-75 (May 10, 2016).

CRYSTALLINE FORMS, COMPOSITIONS CONTAINING SAME, AND METHODS OF THEIR USE

BACKGROUND

The invention relates to crystalline forms, compositions containing them, and methods of their use, e.g., in inhibiting the activity of a BAF complex in a subject or in treating cancer in a subject.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWI2-like ATPases known as BRG1 (Brahma-related gene-1) and BRM (Brahma). The transcription activator BRG1, also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

SUMMARY OF THE INVENTION

The present invention features crystalline forms of a compound useful for modulating a BAF complex.

In one aspect, the invention provides a crystalline form of the compound of formula (I):

(I)

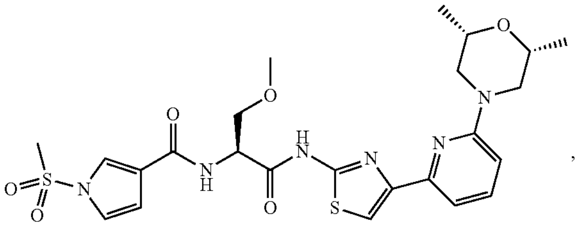

, where the crystalline form is characterized by a powder x-ray diffraction pattern having peaks at 14.4 °2θ±0.2 °2θ and 17.4 °2θ±0.2 °2θ. In some embodiments, the crystalline form is further characterized by a powder x-ray diffraction pattern having peaks at 11.7 °2θ±0.2 °2θ and 15.2 °2θ±0.2 °2θ. In some embodiments, the crystalline form is further characterized by a powder x-ray diffraction pattern having peaks at 14.9 °2θ±0.2 °2θ and 18.5 °2θ±0.2 °2θ. In some embodiments, the crystalline form is further characterized by a powder x-ray diffraction pattern having peaks at 16.0 °2θ±0.2 °2θ and 19.1 °2θ±0.2 °2θ. In some embodiments, the crystalline form is further characterized by a powder x-ray diffraction pattern having a peak at 16.3 °2θ±0.2 °2θ. In some embodiments, the crystalline form is further characterized by a powder x-ray diffraction pattern having peaks at 20.6 °2θ±0.2 °2θ and 26.3 °2θ±0.2 °2θ. In some embodiments, the crystalline form is further characterized by a powder x-ray diffraction pattern having peaks at 21.2 °2θ±0.2 °2θ and 26.6 °2θ±0.2 °2θ.

In some embodiments, the crystalline form is further characterized by a differential scanning calorimetry thermogram having an endothermic event onset at 173.5° C. to 180.1° C.

In another aspect, the invention provides a crystalline form of the compound of formula (I):

(I)

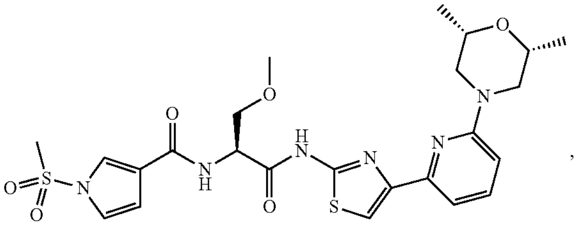

, where the crystalline form is characterized by a powder x-ray diffraction pattern having peaks at 7.7 °2θ±0.2 °2θ, 9.4 °2θ±0.2 °2θ and 17.0 °2θ±0.2 °2θ. In some embodiments, the crystalline form is further characterized by a powder x-ray diffraction pattern having peaks at 18.8 °2θ±0.2 °2θ and 20.0 °2θ±0.2 °2θ. In some embodiments, the crystalline form is further characterized by a powder x-ray diffraction pattern having a peak at 23.7 °2θ±0.2 °2θ. In some embodiments, the crystalline form is further characterized by a powder x-ray diffraction pattern having a peak at 14.8 °2θ±0.2 °2θ.

In some embodiments, the crystalline form is further characterized by a differential scanning calorimetry thermogram having an endothermic event onset at 196.0° C. to 198.8° C.

In yet another aspect, the invention provides a pharmaceutical composition including a crystalline form described herein.

In still another aspect, the invention provides a unit dosage form including the crystalline form described herein. In some embodiments, the unit dosage form is a capsule. In some embodiments, the unit dosage form includes one or more of a filler (e.g., microcrystalline cellulose, mannitol, or a combination thereof), a disintegrant (e.g., croscarmellose sodium), a wetting agent (e.g., sodium lauryl sulfate), a glidant (e.g., colloidal silicon dioxide), a lubricant (e.g., magnesium stearate), and a capsule shell.

In some embodiments, the unit dosage form includes 70 to 90% (w/w) of the filler. In some embodiments, the unit dosage form includes 4 to 6% (w/w) of the disintegrant. In some embodiments, the unit dosage form includes 0.5 to 1.5% (w/w) of the wetting agent. In some embodiments, the unit dosage form includes 1.5 to 2.5% (w/w) of the glidant. In some embodiments, the unit dosage form includes 0.4 to 0.6% (w/w) of the lubricant.

In some embodiments, the capsule shell includes a polymeric shell. In some embodiments, the polymeric shell includes hypromellose and titanium dioxide.

In a further aspect, the invention provides a method of decreasing the activity of a BAF complex in a subject, the method including administering to the subject an effective amount of the crystalline form described herein, the pharmaceutical composition described herein, or the unit dosage form described herein.

In yet further aspect, the invention provides a method of inhibiting BRM in a subject, the method including administering to the subject an effective amount of the crystalline form described herein, the pharmaceutical composition described herein, or the unit dosage form described herein.

In still further aspect, the invention provides a method of inhibiting BRG1 in a subject, the method including administering to the subject an effective amount of the crystalline form described herein, the pharmaceutical composition described herein, or the unit dosage form described herein.

In another aspect, the invention provides a method of inhibiting BRM and BRG1 in a subject, the method including administering to the subject an effective amount of the crystalline form described herein, the pharmaceutical composition described herein, or the unit dosage form described herein.

In yet another aspect, the invention provides a method of inducing apoptosis in a subject, the method including administering to the subject an effective amount of the crystalline form described herein, the pharmaceutical composition described herein, or the unit dosage form described herein.

In some embodiments, the subject has cancer.

In still another aspect, the invention provides a method of treating a BAF complex-related disorder in a subject in need thereof, the method including administering to the subject an effective amount of the crystalline form described herein, the pharmaceutical composition described herein, or the unit dosage form described herein.

In a further aspect, the invention provides a method of treating a disorder related to a BRG1 loss of function mutation in a subject in need thereof, the method including administering to the subject an effective amount of the crystalline form described herein, the pharmaceutical composition described herein, or the unit dosage form described herein.

In some embodiments, the subject is determined to have a BRG1 loss of function disorder. In some embodiments, the BAF complex-related disorder or disorder related to a BRG1 loss of function mutation is a cancer, a viral infection, coffin siris, neurofibromatosis (e.g., selected from the group consisting of neurofibromatosis type I (NF-1), neurofibromatosis type II (NF-2), and Schwannomatosis), or multiple meningioma.

In yet further aspect, the invention provides a method of treating cancer in a subject in need thereof, the method including administering to the subject an effective amount of the crystalline form described herein, the pharmaceutical composition described herein, or the unit dosage form described herein.

In still further aspect, the invention provides a method of reducing tumor growth of cancer in a subject in need thereof, the method including administering to the subject an effective amount of the crystalline form described herein, the pharmaceutical composition described herein, or the unit dosage form described herein.

In another aspect, the invention provides a method of suppressing metastatic progression of cancer in a subject in need thereof, the method including administering to the subject an effective amount of the crystalline form described herein, the pharmaceutical composition described herein, or the unit dosage form described herein.

In yet another aspect, the invention provides a method of suppressing metastatic colonization of cancer in a subject in need thereof, the method including administering to the subject an effective amount of the crystalline form described herein, the pharmaceutical composition described herein, or the unit dosage form described herein.

In still another aspect, the invention provides a method of reducing the level and/or activity of BRG1 and/or BRM in a cancer in a subject in need thereof, the method including administering to the subject an effective amount of the crystalline form described herein, the pharmaceutical composition described herein, or the unit dosage form described herein.

In some embodiments, the cancer is non-small cell lung cancer, colorectal cancer, bladder cancer, cancer of unknown primary, glioma, breast cancer, melanoma, non-melanoma skin cancer, endometrial cancer, esophageal cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, adrenocortical carcinoma, appendiceal cancer, small bowel cancer, penile cancer, bone cancer, or hematologic cancer. In some embodiments, the cancer is esophageal cancer.

In some embodiments, the cancer is non-small cell lung cancer, colorectal cancer, bladder cancer, cancer of unknown primary, glioma, breast cancer, melanoma, non-melanoma skin cancer, endometrial cancer, penile cancer, bone cancer, renal cell carcinoma, prostate cancer, or hematologic cancer. In some embodiments, the cancer is non-small cell lung cancer.

In some embodiments, the cancer is melanoma, prostate cancer, breast cancer, bone cancer, renal cell carcinoma, or hematologic cancer. In some embodiments, the cancer is melanoma (e.g., uveal melanoma, mucosal melanoma, or cutaneous melanoma). In some embodiments, the melanoma is uveal melanoma.

In some embodiments, the cancer is prostate cancer.

In some embodiments, the cancer is hematologic cancer (e.g., multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia, diffuse large cell lymphoma, or non-Hodgkin's lymphoma). In some embodiments, the hematologic cancer is acute myeloid leukemia.

In some embodiments, the cancer is breast cancer (e.g., an ER positive breast cancer, an ER negative breast cancer, triple positive breast cancer, or triple negative breast cancer).

In some embodiments, the cancer is a bone cancer (e.g., Ewing's sarcoma).

In some embodiments, the cancer is a renal cell carcinoma (e.g., a microphthalmia transcription factor family translocation renal cell carcinoma).

In some embodiments, the cancer is non-small cell lung cancer, prostate cancer, esophagogastric cancer, hematologic cancer, or melanoma. In some embodiments, the hematologic cancer is acute myeloid leukemia. In some embodiments, melanoma is uveal melanoma.

In some embodiments, the cancer expresses BRG1 and/or BRM protein.

In some embodiments, the subject or cancer has a BRG1 loss of function mutation. In some embodiments, the BRG1 loss of function mutation is in the ATPase catalytic domain of the protein. In other embodiments, the BRG1 loss of function mutation is a deletion at the C-terminus of BRG1.

In some embodiments, the cancer does not have, or has been determined not to have, an epidermal growth factor receptor mutation and/or an anaplastic lymphoma kinase driver mutation.

In some embodiments, the cancer has, or has been determined to have, a KRAS mutation, a mutation in GNAQ, a mutation in GNA11, a mutation in PLCB4, a mutation in CYSLTR2, a mutation in BAP1, a mutation in SF3B1, a mutation in EIF1AX, a TFE3 translocation, a TFEB translocation, a MITF translocation, an EZH2 mutation, a SUZ12 mutation, and/or an EED mutation.

In some embodiments, the cancer is metastatic.

In some embodiments, the cancer is resistant to, or failed to respond to prior treatment with, an anticancer therapy (e.g., a chemotherapeutic or cytotoxic agent (e.g., a mitogen-activated protein kinase (MEK) inhibitor and/or a protein kinase C (PKC) inhibitor), immunotherapy, surgery, radiotherapy, thermotherapy, or photocoagulation, or a combination thereof). In some embodiments, the cancer is resistant to, or failed to respond to prior treatment with a PKC inhibitor.

In some embodiments, the method further includes administering to the subject an anticancer therapy (e.g., a chemotherapeutic or cytotoxic agent, immunotherapy, surgery, radiotherapy, thermotherapy, or photocoagulation, or a combination thereof). In some embodiments, the anticancer therapy is surgery, a MEK inhibitor (e.g., selumetinib, binimetinib, or tametinib), and/or a PKC inhibitor (e.g., sotrastaurin or IDE196), or a combination thereof.

In a further aspect, the invention provides a method for treating a viral infection in a subject in need thereof, the method including administering to the subject an effective amount of the crystalline form described herein, the pharmaceutical composition described herein, or the unit dosage form described herein.

In some embodiments, the viral infection is an infection with a virus of the Retroviridae family, a virus of the Hepadnaviridae family, a virus of the Flaviviridae family, a virus of the Adenoviridae family, a virus of the Herpesviridae family, a virus of the Papillomaviridae family, a virus of the Parvoviridae family, a virus of the Polyomaviridae family, a virus of the Paramyxoviridae family, or a virus of the Togaviridae family.

In some embodiments, the effective amount of the crystalline form of the compound reduces the level and/or activity of BRG1 by at least 5% as compared to a reference. In some embodiments, the effective amount of the crystalline form of the compound reduces the level and/or activity of BRG1 by at least 5% as compared to a reference for at least 12 hours.

In some embodiments, the effective amount of the crystalline form of the compound reduces the level and/or activity of BRM by at least 5% as compared to a reference. In some embodiments, the effective amount of the crystalline form of the compound reduces the level and/or activity of BRM by at least 5% as compared to a reference for at least 12 hours.

Definitions

In this application, unless otherwise clear from context, (i) the term "a" may be understood to mean "at least one"; (ii) the term "or" may be understood to mean "and/or"; and (iii) the terms "comprising" and "including" may be understood to encompass itemized components or steps whether presented by themselves or together with one or more additional components or steps.

As used herein, the terms "about" and "approximately" refer to a value that is within 10% above or below the value being described. For example, the term "about 5%" indicates a range of from 4.5 to 5.5 As used herein, the term "administration" refers to the administration of a composition (e.g., a compound or a preparation that includes a compound as described herein) to a subject or system.

Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "BAF complex" refers to the BRG1- or HBRM-associated factors complex in a human cell.

As used herein, the term "BAF complex-related disorder" refers to a disorder that is caused or affected by the level of activity of a BAF complex.

As used herein, the term "BRG1 loss of function mutation" refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term "BRG1 loss of function disorder" refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

By a "decreased level" or an "increased level" of a protein or RNA is meant a decrease or increase, respectively, in a protein or RNA level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein in a sample.

By "decreasing the activity of a BAF complex" is meant decreasing the level of an activity related to a BAF complex, or a related downstream effect. A non-limiting example of decreasing an activity of a BAF complex is Sox2 activation. The activity level of a BAF complex may be measured using any method known in the art, e.g., the methods described in Kadoch et al. Cell, 2013, 153, 71-85, the methods of which are herein incorporated by reference.

A cancer "determined to be drug resistant," as used herein, refers to a cancer that is drug resistant, based on unresponsiveness or decreased responsiveness to a chemotherapeutic agent, or is predicted to be drug resistant based on a prognostic assay (e.g., a gene expression assay).

By a "drug resistant" is meant a cancer that does not respond, or exhibits a decreased response to, one or more chemotherapeutic agents (e.g., any agent described herein).

As used herein, the term "failed to respond to a prior therapy" or "refractory to a prior therapy," refers to a cancer that progressed despite treatment with the therapy.

As used herein, the term "inhibiting BRM" and/or "inhibiting BRG1" refers to blocking or reducing the level or activity of the ATPase catalytic binding domain or the bromodomain of the protein. BRM and/or BRG1 inhibition may be determined using methods known in the art, e.g., a BRM and/or BRG1 ATPase assay, a Nano DSF assay, or a BRM and/or BRG1 Luciferase cell assay.

As used herein, the term "LXS196," also known as IDE196, refers to the PKC inhibitor having the structure:

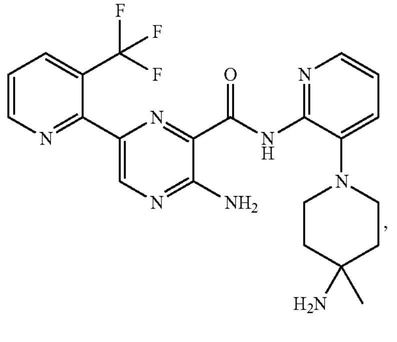 [SMILES: CC1(N)CCN(c2cccnc2NC(=O)c2nc(-c3ncccc3C(F)(F)F)cnc2N)CC1]

or a pharmaceutically acceptable salt thereof.

As used herein, "metastatic nodule" refers to an aggregation of tumor cells in the body at a site other than the site of the original tumor.

As used herein, "metastatic cancer" refers to a tumor or cancer in which the cancer cells forming the tumor have a high potential to or have begun to, metastasize, or spread from one location to another location or locations within a subject, via the lymphatic system or via haematogenous spread, for example, creating secondary tumors within the subject. Such metastatic behavior may be indicative of malignant tumors. In some cases, metastatic behavior may be associated with an increase in cell migration and/or invasion behavior of the tumor cells.

Examples of cancers that can be defined as metastatic include but are not limited to lung cancer (e.g., non-small cell lung cancer), breast cancer, ovarian cancer, colorectal cancer, biliary tract cancer, bladder cancer, brain cancer including glioblastomas and medullablastomas, cervical cancer, choriocarcinoma, endometrial cancer, esophageal cancer, gastric cancer, hematological neoplasms, multiple myeloma, leukemia, intraepithelial neoplasms, liver cancer, lymphomas, neuroblastomas, oral cancer, pancreatic cancer, prostate cancer, sarcoma, skin cancer including melanoma, basocellular cancer, squamous cell cancer, testicular cancer, stromal tumors, germ cell tumors, thyroid cancer, and renal cancer.

"Non-metastatic cell migration cancer" as used herein refers to cancers that do not migrate via the lymphatic system or via haematogenous spread.

The term "pharmaceutical composition," as used herein, represents a composition containing a compound described herein formulated with a pharmaceutically acceptable excipient and appropriate for administration to a mammal, for example a human. Typically, a pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration.

"Proliferation" as used in this application involves reproduction or multiplication of similar forms (cells) due to constituting (cellular) elements.

By a "reference" is meant any useful reference used to compare protein or RNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein or RNA (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein or RNA, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean therapeutic treatment or any measures whose object is to slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total); an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. Compounds of the invention may also be used to "prophylactically treat" or "prevent" a disorder, for example, in a subject at increased risk of developing the disorder.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION

Figure 1A:
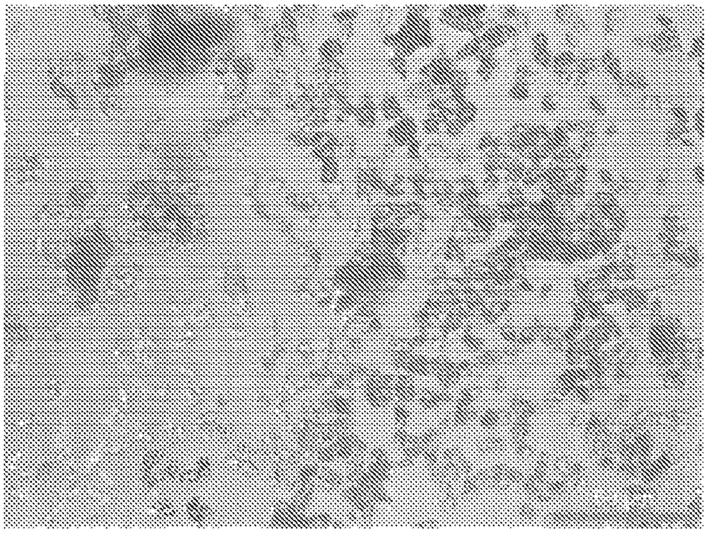
FIGS. 1A and 1B are a series of microscopic images of the first and second crystalline forms, respectively, of the compound of formula (I). The images were made in polarized, visible light.

In general, the invention provides crystalline forms of the compound of formula (I):

(I)

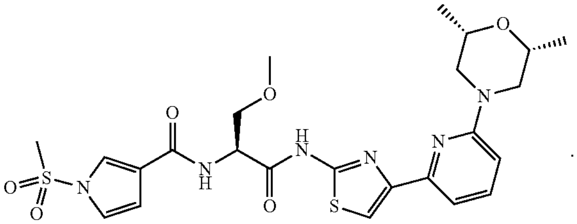
.

In particular, the invention provides two crystalline forms of the compound of formula (I): a first crystalline form and a second crystalline form.

Methods

A crystalline form described herein (e.g., the first or second crystalline form of the compound of formula (I)) is useful in the methods of the invention and, while not bound by theory, are believed to exert their ability to modulate the level, status, and/or activity of a BAF complex, i.e., by inhibiting the activity of the BRG1 and/or BRM proteins within the BAF complex in a mammal. BAF complex-related disorders include, but are not limited to, BRG1 loss of function mutation-related disorders.

An aspect of the present invention relates to methods of treating disorders related to BRG1 loss of function mutations such as cancer (e.g., non-small cell lung cancer, colorectal cancer, bladder cancer, cancer of unknown primary, glioma, breast cancer, melanoma, non-melanoma skin cancer, endometrial cancer, or penile cancer) in a subject in need thereof. In some embodiments, the present invention relates to methods of treating melanoma (e.g., uveal melanoma), prostate cancer, breast cancer, bone cancer, renal cell carcinoma, or a hematologic cancer.

In some embodiments, the compound is administered in an amount and for a time effective to result in one or more (e.g., two or more, three or more, four or more) of: (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, (i) increased progression free survival of subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Exemplary cancers that may be treated by the invention include, but are not limited to, non-small cell lung cancer, small-cell lung cancer, colorectal cancer, bladder cancer, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, hematologic cancer, and penile cancer.

Combination Formulations and Uses Thereof

The compounds of the invention can be combined with one or more therapeutic agents. In particular, the therapeutic agent can be one that treats or prophylactically treats any cancer described herein.

Combination Therapies

A compound of the invention can be used alone or in combination with an additional therapeutic agent, e.g., other agents that treat cancer or symptoms associated therewith, or in combination with other types of treatment to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), ABraxane®, cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chloranbucil; Gemzar® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (Avastin®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituxan (Rituximab); Zenapax (Daclizumab); Simulect (Basiliximab); Synagis (Palivizumab); Remicade (Infliximab); Herceptin (Trastuzumab); Mylotarg (Gemtuzumab ozogamicin); Campath (Alemtuzumab); Zevalin (lbritumomab tiuxetan); Humira (Adalimumab); Xolair (Omalizumab); Bexxar (Tositumomab-I-131); Raptiva (Efalizumab); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab). Also included are antibody-drug conjugates.

The second agent may be a therapeutic agent which is a non-drug treatment. For example, the second therapeutic agent is radiation therapy, cryotherapy, hyperthermia and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody such as ipilimumab/Yervoy or tremelimumab). In some embodiments, the inhibitor of checkpoint is an inhibitor (e.g., an inhibitory antibody or small molecule inhibitor) of PD-1 (e.g., nivolumab/Opdivo®; pembrolizumab/Keytruda®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MED14736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK1, CHK2, A2aR, B-7 family ligands, or a combination thereof.

In some embodiments, the compound of the invention is used in combination with another anti-cancer therapy used for the treatment of uveal melanoma such as surgery, a MEK inhibitor, and/or a PKC inhibitor, or a combination thereof. For example, in some embodiments, the method further comprises performing surgery prior to, subsequent to, or at the same time as administration of the compound of the invention. In some embodiments, the method further comprises administration of a MEK inhibitor (e.g., selumetinib, binimetinib, or tametinib) and/or a PKC inhibitor (e.g., sotrastaurin or IDE196) prior to, subsequent to, or at the same time as administration of the compound of the invention.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

A crystalline form described herein (e.g., the crystalline forms of the compound of formula (I)) may be formulated into pharmaceutical compositions for administration to human subjects in a biologically compatible form suitable for administration in vivo. Pharmaceutical compositions typically include an active agent as described herein and a physiologically acceptable excipient (e.g., a pharmaceutically acceptable excipient). Formulation principles for the compound of formula (I) have been described in WO 2020/160180, the disclosure of which is incorporated by reference herein in its entirety. The crystalline forms described herein are especially beneficial for solid pharmaceutical compositions, e.g., solid dosage forms (e.g., tablets, powders, lozenges, sachets, cachets, and soft and hard gelatin capsules).

The compound of formula (I) of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time. Preferably, a crystalline form of the compound of formula (I) is administered orally.

Suitable pharmaceutical carriers, as well as pharmaceutical necessities for use in pharmaceutical formulations, are described in *Remington: The Science and Practice of Pharmacy,* 21st Ed., Gennaro, Ed., Lippencott Williams & Wilkins (2005), a well-known reference text in this field, and in the USP/NF (United States Pharmacopeia and the National Formulary).

Unit Dosage Forms

A crystalline form described herein (e.g., the second crystalline form of the compound of formula (I)) may be formulated into a unit dosage form for oral administration (e.g., a capsule). The crystalline form of the compound of formula (I) (e.g., the second crystalline form of the compound of formula (I)) may be supplied in different capsule strengths for oral administration (e.g., 1 to 2.5 mg, 2.5 to 5 mg, 5 to 10 mg, 10 to 15 mg, 15 to 20 mg, 20 to 25 mg, or 50 to 100 mg). In some examples, the crystalline form of the compound of formula (I) is supplied in 2.5 mg or 20 mg capsule strengths for oral administration.

The unit dosage form may contain suitable pharmaceutical carriers and excipients as described in the pharmaceutical compositions section. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. The unit dosage form may contain one or more of a filler, a disintegrant, a wetting agent, a glidant, a lubricant, and a capsule shell.

In some examples, the filler may be 70 to 90% (w/w) of the unit dosage form. The filler may be microcrystalline cellulose, mannitol, or a combination thereof.

In some examples, the disintegrant may be 4 to 6% (w/w) of the unit dosage form. The disintegrant may be croscarmellose sodium.

In some examples, the wetting agent may be 0.5 to 1.5% (w/w) of the unit dosage form. The wetting agent may be sodium lauryl sulfate.

In some examples, the glidant may be 1.5 to 2.5% (w/w) of the unit dosage form. The glidant may be colloidal silicon dioxide.

In some examples, the lubricant may be 0.4 to 0.6% (w/w) of the unit dosage form. The lubricant may be magnesium stearate.

In some examples, the capsule shell is made of a polymeric shell. The polymeric shell can be made from hypromellose and titanium dioxide.

A crystalline form described herein (e.g., the second crystalline form of the compound of formula (I)) may be formulated into a unit dosage form for oral administration (e.g., a capsule) as described in Table 1.

TABLE 1

| | | 2.5 mg Capsule | | 20 mg Capsule | |
|---|---|---|---|---|---|
| Component | Function | Amount per Capsule (mg) | Content (%) | Amount per Capsule (mg) | Content (%) |
| Second crystalline form of a compound of formula (I) | Active ingredient | 2.50 | 2.63 | 20.00 | 17.39 |
| Microcrystalline cellulose | Filler | 48.24 | 50.78 | 48.20 | 41.91 |
| Mannitol | Filler | 36.18 | 38.08 | 36.95 | 32.13 |
| Croscarmellose Sodium | Disintegrant | 4.75 | 5.00 | 5.80 | 5.04 |
| Sodium lauryl sulfate | Wetting agent | 0.95 | 1.00 | 1.15 | 1.00 |
| Colloidal silicon dioxide | Glidant | 1.90 | 2.00 | 2.30 | 2.00 |
| Magnesium stearate | Lubricant | 0.48 | 0.51 | 0.60 | 0.52 |
| Size 4, Swedish Orange HPMC Capsules | Capsule Shell | 1 capsule | — | — | — |
| Size 3, Blue Green HPMC Capsules | Capsule Shell | — | — | 1 capsule | — |
| Total | | 95.00 | 100 | 115.00 | 100 |

The composition of the Swedish orange hypromellose capsule shells is described in Table 2.

TABLE 2

| Composition of capsule body and cap | Function | Content |
|---|---|---|
| FDA/E172 RED IRON OXIDE | Colorant | 1.1817% |
| TITANIUM DIOXIDE | Opacifier | 0.4916% |
| Hypromellose | Structure | qs 100% |

The composition of blue green hypromellose capsule shells is described in Table 3.

TABLE 3

| Composition of capsule body and cap | Function | Content |
|---|---|---|
| FD&C Blue #1 | Colorant | 0.0281% |
| FD&C Yellow #5 | Colorant | 0.0069% |
| TITANIUM DIOXIDE | Opacifier | 2.2306% |
| Hypromellose | Structure | qs 100% |

EXAMPLES

The abbreviations below are used throughout the examples section

2-MeTHF 2-Methyl tetrahydrofuran
BSA Benzenesulfonic acid
EtOAc Ethyl acetate
EtOH Ethanol
iPrOAc Isopropyl acetate
iPrOH Isopropanol
KOH Potassium hydroxide
MeCN Acetonitrile
MEK Methyl ethyl ketone
MeOH Methanol
$MgSO_4$ Magnesium sulfate
MTBE Methyl tert-butyl ether
NaOH Sodium hydroxide
THF Tetrahydrofuran
TSA p-Toluenesulfonic acid

Example 1. Preparation of the Crystalline Forms of the Compound of Formula (I)

Preparation of the compound of formula (I) is described in WO 2020/160180, the disclosure of which is incorporated by reference herein in its entirety.

The First Crystalline Form of the Compound of Formula (I).

A reactor with overhead stirring was charged with the compound of formula (I) (250.0 g) and acetonitrile (1250 mL). The contents were stirred at 22° C. for 5 minutes until all solid had dissolved. Purified water (125 mL) and seed (50 mg) were then charged and the mixture was stirred for 10 minutes. Purified water (125 mL) and seed (50 mg) were then charged and the mixture was stirred for 30 minutes. Purified water (250 mL) and seed (100 mg) were then charged and the mixture was stirred for 1 hour. Purified water (875 L) was charged intermittently over the next 21 hours and the reaction was slowly cooled to 9° C. The slurry was filtered and washed with purified water (500 mL). The damp solid was dried under vacuum at 40° C. with a nitrogen purge for 19 hours. Product was obtained as a beige solid (180.3 g). The dried compound of formula (I) (180.3 g) was charged to a 5 L jacketed reactor with overhead stirring and MTBE (901 mL) was added. The slurry was stirred at 7° C. for 1 hour. The slurry was filtered and washed with MTBE (200 mL, 7° C.). The damp solid was dried under vacuum at 40° C. with a nitrogen purge for 24 hours. Pure compound of formula (I) was obtained as an off-white powder (161.2 g), having an XRPD diffractogram consistent with the first crystalline form of the of the compound of formula (I).

The Second Crystalline Form of the Compound of Formula (I).

A 5 L jacketed reactor with overhead stirring was charged with the compound of formula (I) (349.1 g) and acetonitrile (2250 mL, 6.5 vols with respect to the compound of formula (I) weight). The contents were heated to 75° C. and aged for 15 minutes to dissolve all the solid. The brown solution was cooled to 28° C. over 30 minutes and seeded (250 mg) to give a very light seed bed. Purified water (2.3 L) was charged over the next 4 hours. The slurry was cooled to 4° C. The slurry was then stirred for 14 hours. The slurry was filtered and washed with a mixture of acetonitrile (250 mL) and purified water (500 mL), pre-cooled to 5° C. The damp solid was dried under vacuum at 40° C. with a nitrogen purge for 30 hours. The product was obtained as an off-white solid (278.78 g).

A 5 L jacketed reactor with overhead stirring was charged with the compound of formula (I) (700.8 g, obtained from the previous step) and MTBE (3000 mL). The contents were stirred at 20° C. for 15 minutes and then cooled to 5° C. and stirred for 60 minutes. The slurry was filtered and washed with MTBE (1000 mL, pre-cooled to 5° C.). The damp solid was dried under vacuum at 40° C. with a nitrogen purge for 18 hours. Pure compound of formula (I) was obtained as an off-white powder (691.6 g), having an XRPD diffractogram consistent with the second crystalline form of the of the compound of formula (I).

Example 2. Analysis of the Crystalline Forms of the Compound of Formula (I)

X-Ray Powder Diffraction.

X-Ray Powder Diffraction patterns were collected on a Bruker D2 Phaser Gen 2 using Cu Kα radiation (30 kV, 10 mA), θ-θ goniometer, divergence slit (0.2 mm) and an SSD160 (1 D Mode) Detector with a 4.7990 opening. The software used for data collection was Diffrac.Commander version 6.5.0.1 and the data was presented using Diffra.Eva version 4.2.1.11.XRPD diffractograms were acquired under ambient conditions via reflection on a flat silica zero background plate with rotation at 15 revolutions per minute. The data collection range was 3.0-4(%) 2 with a step size of 0.020250 and a collection time of 0.25 seconds per step. Samples were prepared by placing powder onto a flat silica zero background plate and ensuring the sample surface is flat.

The XRPD peak list for the first crystalline form of the compound of formula (I) is provided in Table 4, and the XRPD peak list for the second crystalline form of the compound of formula (I) is provided in Table 5.

TABLE 4

| No. | Angle (°2θ) | d Value (Å) | Net Intensity | Gross Intensity | Relative Intensity (%) |
|---|---|---|---|---|---|
| 1 | 9.862 | 8.96179 | 40.8 | 66.4 | 6.2 |
| 2 | 10.269 | 8.60739 | 79.9 | 105.0 | 12.1 |
| 3 | 10.521 | 8.40146 | 95.5 | 120.0 | 14.5 |
| 4 | 10.821 | 8.16932 | 48.1 | 70.8 | 7.3 |
| 5 | 11.650 | 7.58961 | 92.3 | 116.0 | 14.0 |
| 6 | 11.829 | 7.47514 | 178.0 | 202.0 | 27.1 |
| 7 | 12.251 | 7.21876 | 104.0 | 128.0 | 15.8 |
| 8 | 14.375 | 6.15661 | 167.0 | 192.0 | 25.4 |
| 9 | 14.903 | 5.93985 | 312.0 | 339.0 | 47.3 |
| 10 | 15.190 | 5.82815 | 282.0 | 310.0 | 42.8 |
| 11 | 16.023 | 5.52702 | 184.0 | 212.0 | 28.0 |
| 12 | 16.295 | 5.43544 | 151.0 | 178.0 | 22.9 |
| 13 | 17.369 | 5.10142 | 659.0 | 686.0 | 100.0 |
| 14 | 18.452 | 4.80441 | 226.0 | 254.0 | 34.3 |
| 15 | 19.065 | 4.65142 | 471.0 | 497.0 | 71.4 |
| 16 | 19.358 | 4.58160 | 53.1 | 79.1 | 8.1 |
| 17 | 20.589 | 4.31029 | 332.0 | 361.0 | 50.3 |
| 18 | 21.199 | 4.18773 | 548.0 | 577.0 | 83.2 |
| 19 | 23.190 | 3.83247 | 134.0 | 161.0 | 20.4 |
| 20 | 24.121 | 3.68657 | 23.6 | 47.2 | 3.6 |
| 21 | 24.266 | 3.66499 | 107.0 | 130.0 | 16.3 |
| 22 | 25.161 | 3.53653 | 230.0 | 251.0 | 34.9 |
| 23 | 26.298 | 3.38614 | 62.8 | 81.9 | 9.5 |
| 24 | 26.635 | 3.34411 | 144.0 | 163.0 | 21.9 |
| 25 | 28.225 | 3.15924 | 93.8 | 110.0 | 14.2 |
| 26 | 28.653 | 3.11303 | 10.1 | 26.1 | 1.5 |
| 27 | 31.082 | 2.87505 | 24.0 | 37.5 | 3.6 |
| 28 | 31.660 | 2.82381 | 15.4 | 28.8 | 2.3 |
| 29 | 35.498 | 2.52681 | 23.1 | 39.8 | 3.5 |
| 30 | 36.400 | 2.46625 | 28.8 | 44.9 | 4.4 |
| 31 | 39.541 | 2.27730 | 26.0 | 39.6 | 3.9 |

TABLE 5

| No. | Angle (°2θ) | d Value (Å) | Net Intensity | Gross Intensity | Relativ Intensity (%) |
|---|---|---|---|---|---|
| 1 | 7.655 | 11.53919 | 943.0 | 968.0 | 70.4 |
| 2 | 8.341 | 10.59243 | 261.0 | 288.0 | 19.5 |
| 3 | 9.369 | 9.43180 | 1340.0 | 1366.0 | 100.0 |
| 4 | 10.643 | 8.30546 | 170.0 | 190.0 | 12.7 |
| 5 | 12.080 | 7.32059 | 138.0 | 153.0 | 10.3 |
| 6 | 13.665 | 6.47491 | 22.7 | 37.4 | 1.7 |
| 7 | 14.822 | 5.97215 | 986.0 | 1005.0 | 73.6 |
| 8 | 15.288 | 5.79109 | 37.8 | 58.7 | 2.8 |
| 9 | 15.892 | 5.57208 | 546.0 | 567.0 | 40.7 |
| 10 | 16.996 | 5.21276 | 1323.0 | 1344.0 | 98.7 |
| 11 | 17.657 | 5.01891 | 22.4 | 43.5 | 1.7 |
| 12 | 18.757 | 4.72715 | 547.0 | 573.0 | 40.9 |
| 13 | 19.227 | 4.61258 | 42.5 | 69.0 | 3.2 |
| 14 | 19.979 | 4.44064 | 536.0 | 564.0 | 40.0 |
| 15 | 20.554 | 4.31770 | 163.0 | 190.0 | 12.2 |
| 16 | 21.239 | 4.17989 | 92.4 | 116.0 | 6.9 |
| 17 | 22.012 | 4.03493 | 161.0 | 185.0 | 12.1 |
| 18 | 22.759 | 3.90404 | 92.1 | 116.0 | 6.9 |
| 19 | 23.026 | 3.85936 | 223.0 | 247.0 | 16.6 |
| 20 | 23.722 | 3.74769 | 274.0 | 300.0 | 20.4 |
| 21 | 24.322 | 3.65655 | 132.0 | 158.0 | 9.9 |
| 22 | 25.241 | 3.52552 | 151.0 | 174.0 | 11.3 |
| 23 | 26.017 | 3.42209 | 182.0 | 204.0 | 13.6 |
| 24 | 28.174 | 3.16483 | 19.3 | 38.0 | 1.4 |
| 25 | 29.079 | 3.06831 | 156.0 | 174.0 | 11.6 |
| 26 | 30.833 | 2.89770 | 42.4 | 57.2 | 3.2 |
| 27 | 31.943 | 2.79946 | 12.6 | 25.4 | 0.9 |
| 28 | 32.735 | 2.73356 | 21.3 | 34.2 | 1.6 |
| 29 | 33.722 | 2.65577 | 18.6 | 31.8 | 1.4 |
| 30 | 34.750 | 2.57952 | 63.5 | 77.9 | 4.7 |
| 31 | 35.682 | 2.51422 | 26.9 | 41.7 | 2.0 |
| 32 | 36.108 | 2.48552 | 35.8 | 51.0 | 2.7 |

TABLE 5-continued

| No. | Angle (°2θ) | d Value (Å) | Net Intensity | Gross Intensity | Relativ Intensity (%) |
|---|---|---|---|---|---|
| 33 | 36.712 | 2.44602 | 20.2 | 36.3 | 1.5 |
| 34 | 37.971 | 2.36775 | 36.3 | 51.1 | 2.7 |
| 35 | 38.616 | 2.32969 | 14.2 | 28.5 | 1.1 |

Differential Scanning Calorimetry (DSC) and Thermal Gravimetric Analysis (TGA).

Figure 2A:
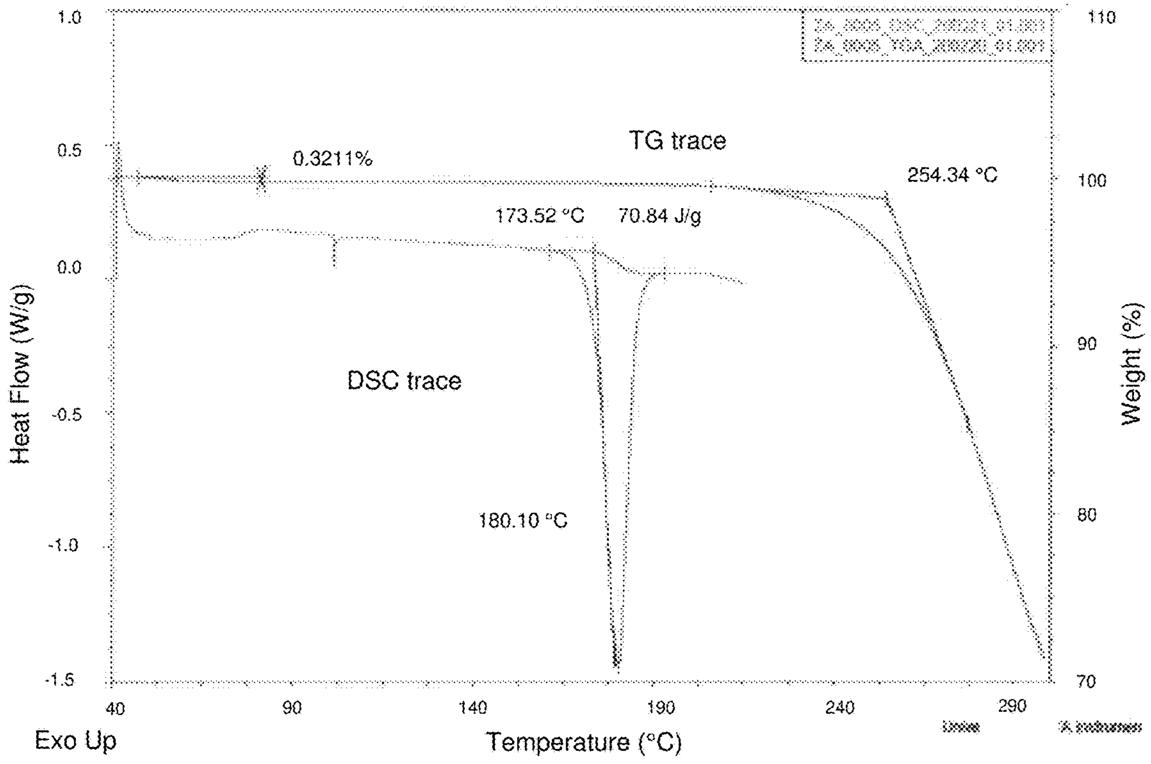
FIG. 2A is a plot showing TG and DSC traces for the first crystalline form of the compound of formula (I). The TG trace exhibited low temperature weight loss of 0.3% (w/w) due to loss of the free water in the sample. The DSC trace displayed a sharp endothermic event (onset at about 173.5° C.) which was likely due to the sample melting.
Figure 2B:
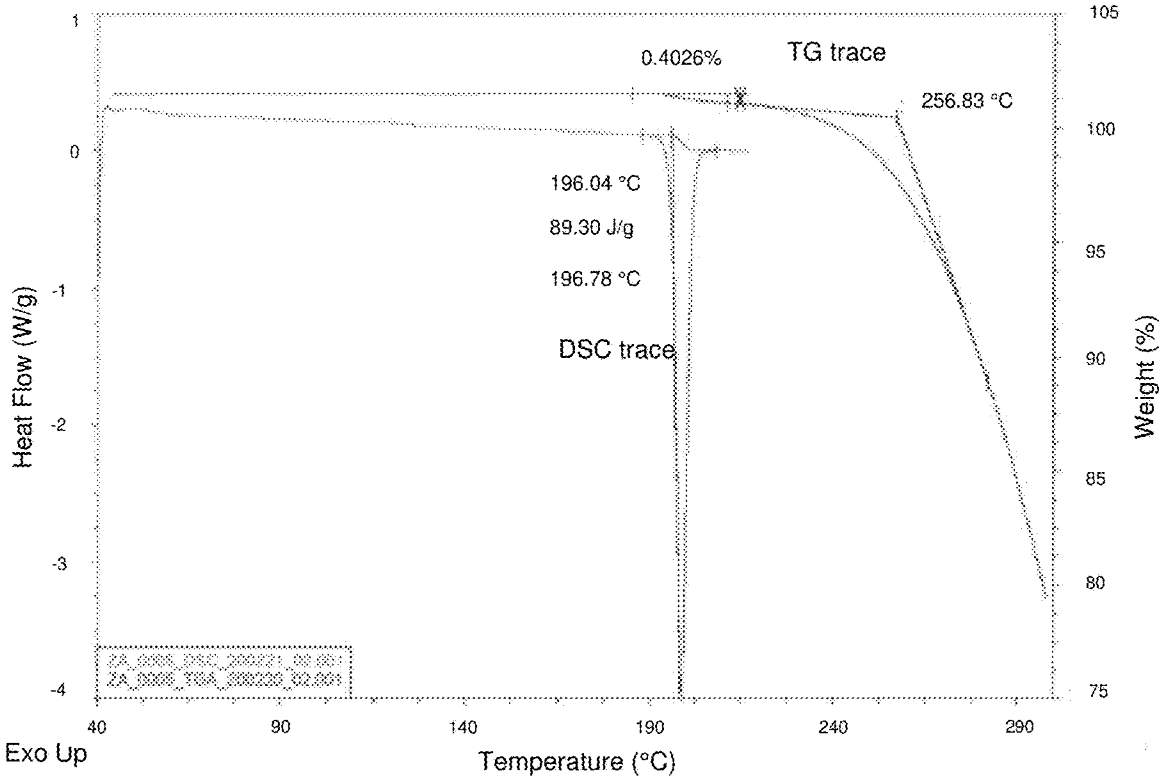
FIG. 2B is a plot showing TG and DSC traces for the second crystalline form of the compound of formula (I). The TG trace showed no significant loss in mass prior melting, with a weight loss of 0.4% (w/w), indicating the inclusion of solvent in the crystal structure. The DSC trace displayed a sharp endothermic event (onset at about 196.0° C.) which was likely due to the sample melting.
Figure 3:
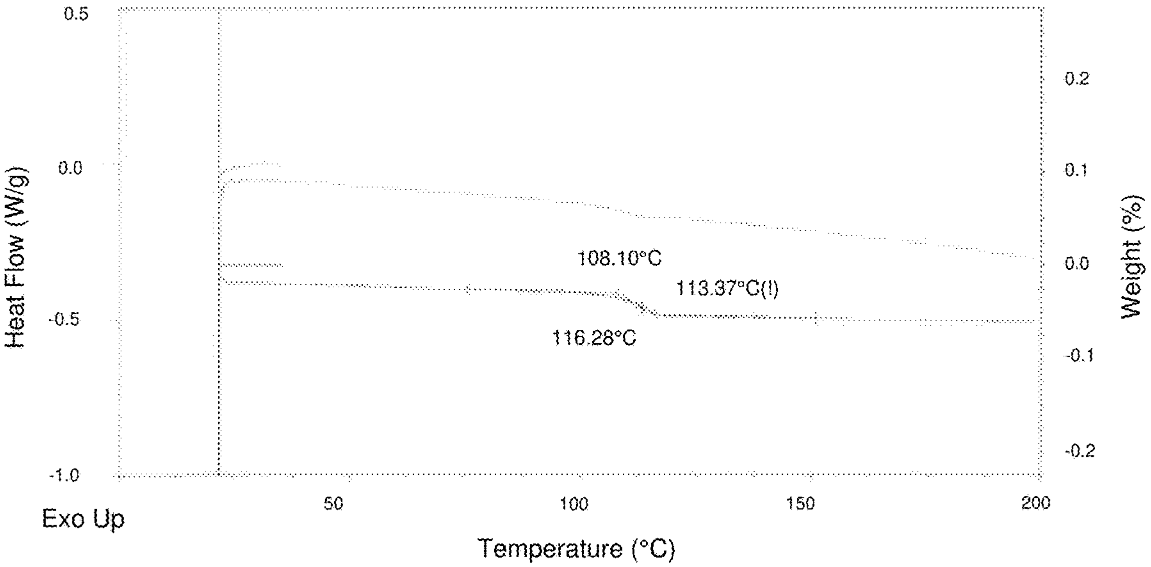
FIG. 3 is a plot showing modulated DSC traces for the first crystalline form of the compound of formula (I) with two heating cycles.

DSC data was collected on a TA Instruments Q2000 DSC. A predefined amount of the sample, 2.0 to 10.0 mg, was placed in an aluminum pan and heated at 5° C./minute from 25° C. to 220° C. A purge of dry nitrogen at 100 mL/minute was maintained over the sample. The instrument control and data acquisition are acquired using Q Advantage software release version 5.5.23. The data was processed and presented using the TA Universal Analysis 2000 software version 4.5A build 4.5.0.5. FIG. 2A shows the DSC trace for the first crystalline form of the compound of formula (I) and FIG. 2B shows the DSC trace for the second crystalline form of the compound of formula (I). FIG. 3 shows the modulated DSC performed for the first crystalline form of the compound of formula (I) with two heating cycles.

TGA data was collected on a TA Instruments Q5000 TGA. A predefined amount of the sample, 2.0 to 10.0 mg, was placed in an aluminum pan and heated at 10° C./minute from 40° C. to 300° C., or varied as experimentation dictated. A purge of dry nitrogen at 25 mL/minute was maintained over the sample. The instrument control and data acquisition are acquired using Q Advantage software release version 5.5.23. The data was processed and presented using the TA Universal Analysis 2000 software version 4.5A build 4.5.0.5. FIG. 2A shows the TGA trace for the first crystalline form of the compound of formula (I) and FIG. 2B shows the TGA trace for the second crystalline form of the compound of formula (I).

The First Crystalline Form of the Compound of Formula (I).

TGA and DSC analysis exhibited low temperature weight loss of 0.3% (w/w) due to loss of the free water in the sample, and molecular degradation from 220° C. with onset at 254.3° C. (FIG. 2A). A melting endotherm was observed at 180.1° C. with an onset at 173.5° C. Modulated DSC performed with two heating cycles showed a glass transition temperature between 108.1° C. and 116.3° C. during the second cycle, indicating that under these measurement conditions the material remained amorphous after melting during the first heating cycle (FIG. 3).

The Second Crystalline Form of the Compound of Formula (I).

TGA and DSC analysis exhibited molecular degradation at 240° C. with no low temperature weight loss (FIG. 2B). A melting endotherm was observed at 198.8° C. with an onset at 196.0° C., accompanied by a weight loss of 0.4% (w/w), indicating the inclusion of solvent in the crystal structure that is only released upon melting. Modulated DSC performed with two heating cycles showed a glass transition temperature between 108.1° C. and 116.3° C. during the second cycle, indicating that under these measurement conditions the material remained amorphous after melting during the first heating cycle (FIG. 3).

Dynamic Vapor Sorption (DVS).

Dynamic vapor sorption (DVS) was carried out using the TA Instruments Q5000 SA. A predefined amount of the sample, 2.0 to 10.0 mg, was placed in a platinum pan. The sample was allowed to equilibrate at 50° C. at 0% RH for a period of 60 minutes. The sample was then equilibrated at 25° C. before ramping the humidity from 0 to 95% RH at 5% increments every hour. A similar ramp profile was used for desorption cycle. XRPD analysis was also performed on post DVS sample.

The First Crystalline Form of the Compound of Formula (I).

Figure 4A:
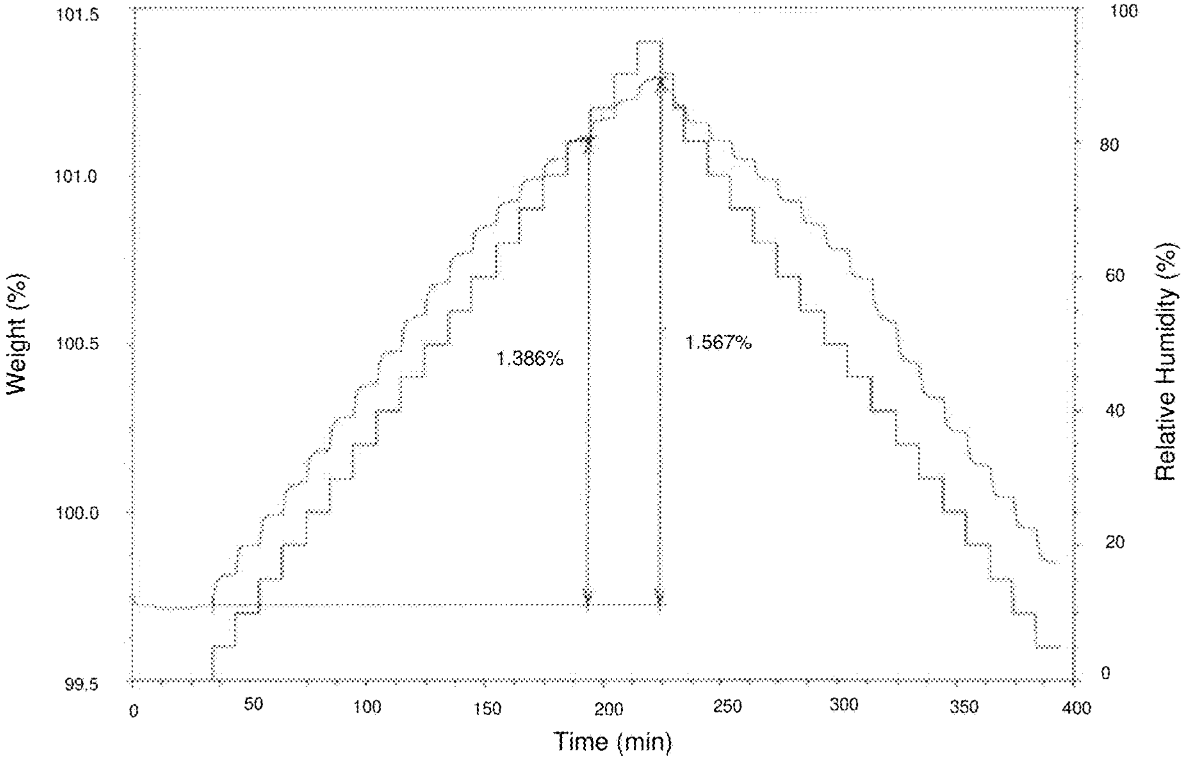
FIG. 4A is a plot showing the DVS cycles for the first crystalline form of the compound of formula (I). The DVS analysis showed at total of 1.4% mass increase up to 80% RH. The material was thus slightly hygroscopic.

DVS analysis showed a weight increase of 1.4% (w/w) during exposure to 80% RH, hence the material is classified as slightly hygroscopic (FIG. 4A). Slight hysteresis is observed but XRPD analysis performed on the sample after DVS showed that no structural changes occurred as a result of exposure to high humidity.

The Second Crystalline Form of the Compound of Formula (I).

Figure 4B:
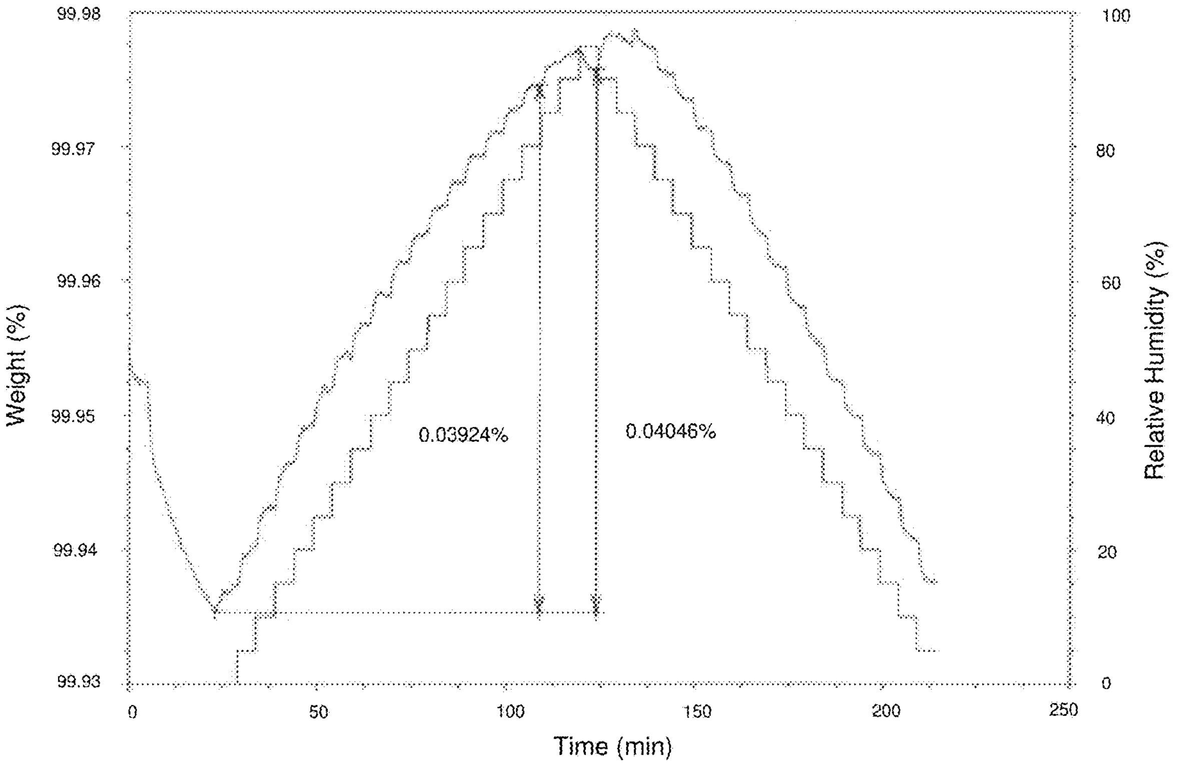
FIG. 4B is a DVS kinetic plot for the first crystalline form of the compound of formula (I).
Figure 5A:
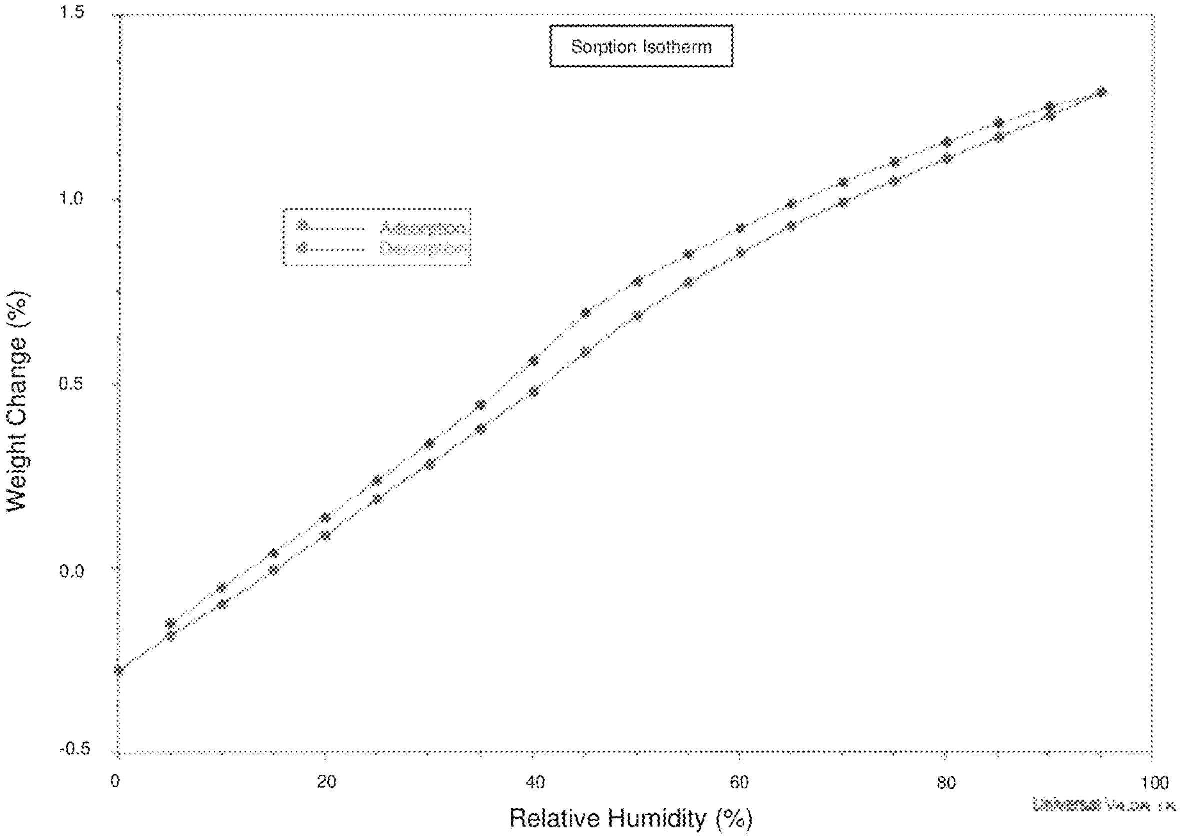
FIG. 5A is a plot showing the DVS cycles for the second crystalline form of the compound of formula (I). The DVS analysis showed at total of 0.04% mass increase up to 80% RH. The material was non-hygroscopic.
Figure 5B:
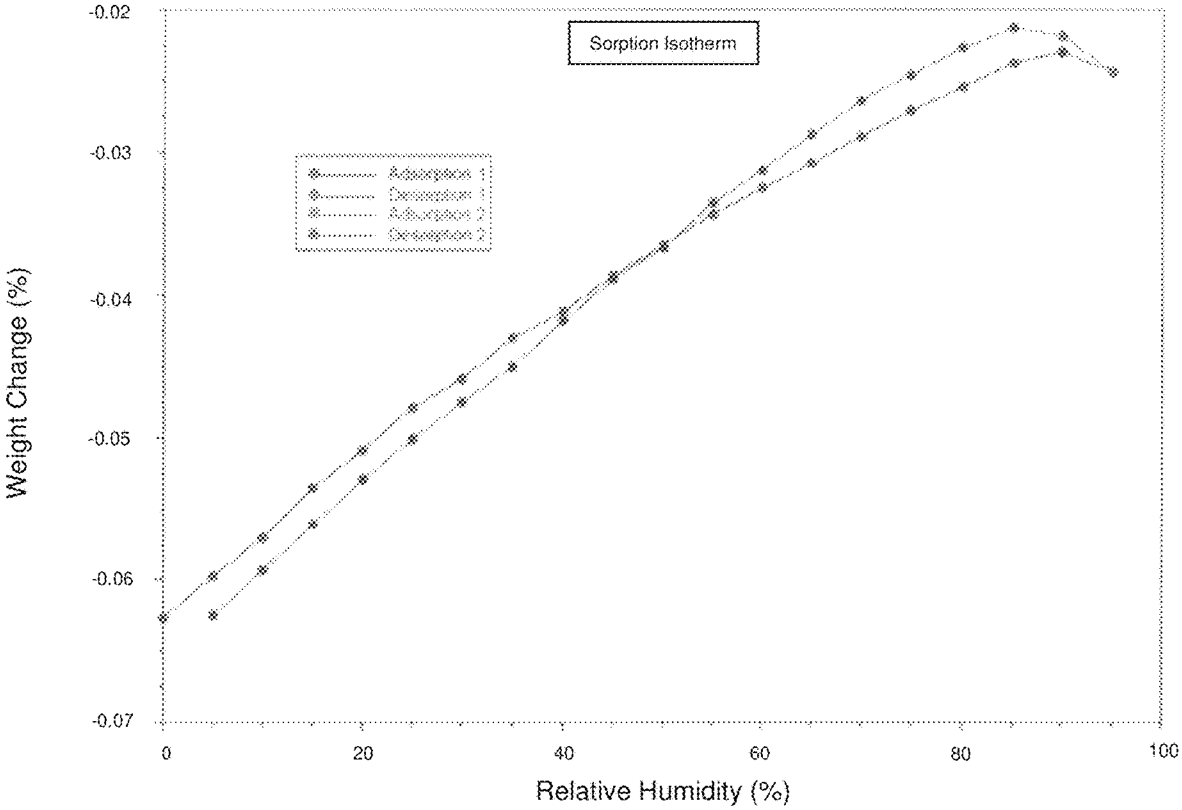
FIG. 5B is a DVS kinetic plot for the second crystalline form of the compound of formula (I).
Figure 6:
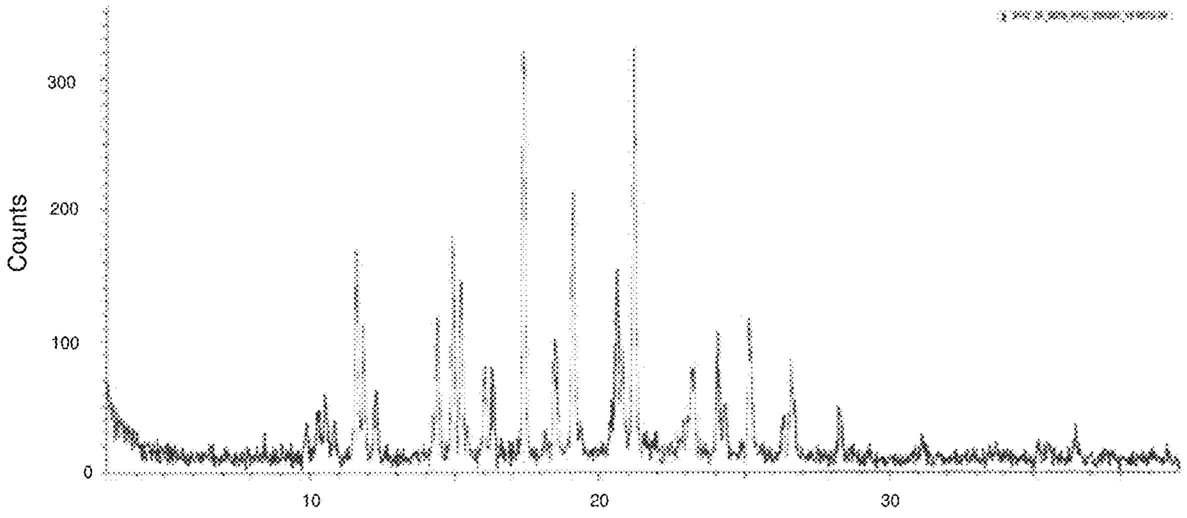
FIG. 6 is a XRPD pattern of the first crystalline form of the compound of formula (I).
Figure 7:
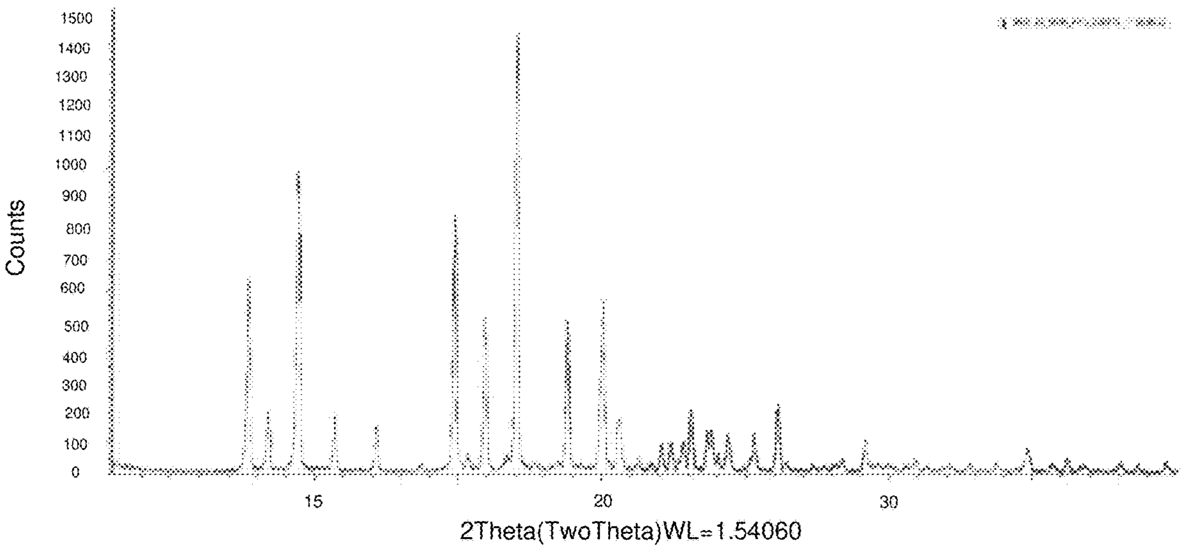
FIG. 7 is a XRPD pattern of the second crystalline form of the compound of formula (I).
Figure 8:
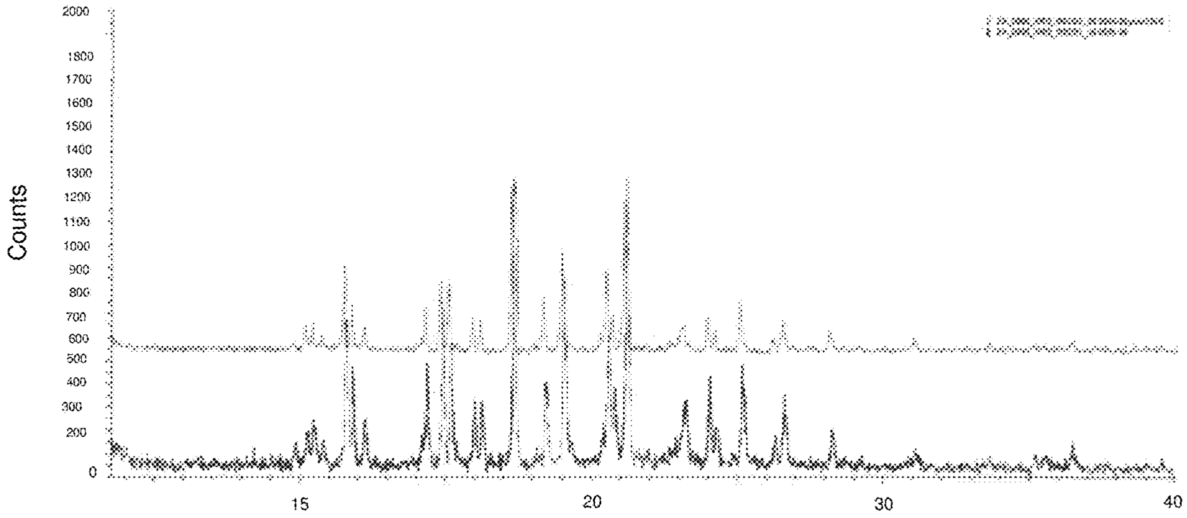
FIG. 8 is an overlay of the XRPD pattern of the first crystalline form of the compound of formula (I) (trace in black) and the XRPD pattern of the first crystalline form of the compound of formula (I) after exposure to high humidity after DVS analysis (trace in magenta).
Figure 9:
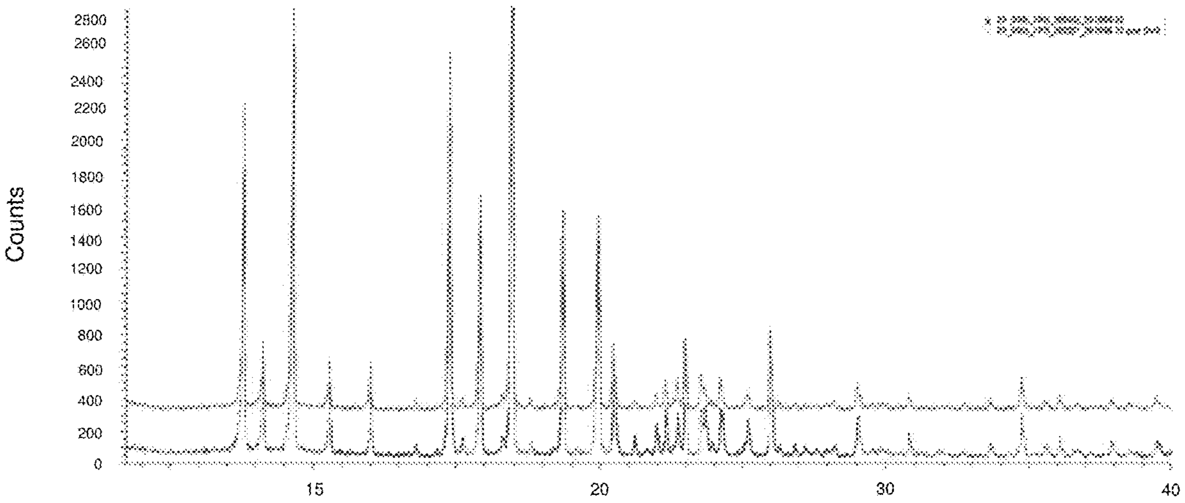
FIG. 9 is an overlay of the XRPD pattern of the second crystalline form of the compound of formula (I) (trace in black) and the XRPD pattern of the second crystalline form of the compound of formula (I) after exposure to high humidity after DVS analysis (trace in blue).

DVS analysis showed an increase of 0.04% (w/w) during exposure to water up to 80% RH, indicating that the material is non-hygroscopic (FIG. 4B). XRPD analysis performed on the sample after DVS showed that no structural changes occurred as a result of exposure to high humidity.

Nuclear Magnetic Resonance (NMR).

$^1$H NMR was performed by dissolving the samples at approximately 10 mg/mL in 0.6 mL volume of deuterated DMSO-d6 and referenced to the TMS at 0.00 ppm before analyzing by Bruker 400 MHz NMR Spectrometer using the parameters shown in Table 6 below. The sample was analyzed using Top Spin software.

TABLE 6

| Method Name | Parameters | Value |
|---|---|---|
| Proton.icon (identity determination) | Pulse angle | 30° |
| | Spectral width (SW) | 30 ppm |
| | Transmitter offset (O1P) | 5 ppm |
| | Digitazation (TD) | 131K |
| | Number of scans (NS) | ≥32 |
| | Pulse repetition time (D1) | ≥3 s |

Figure 10:
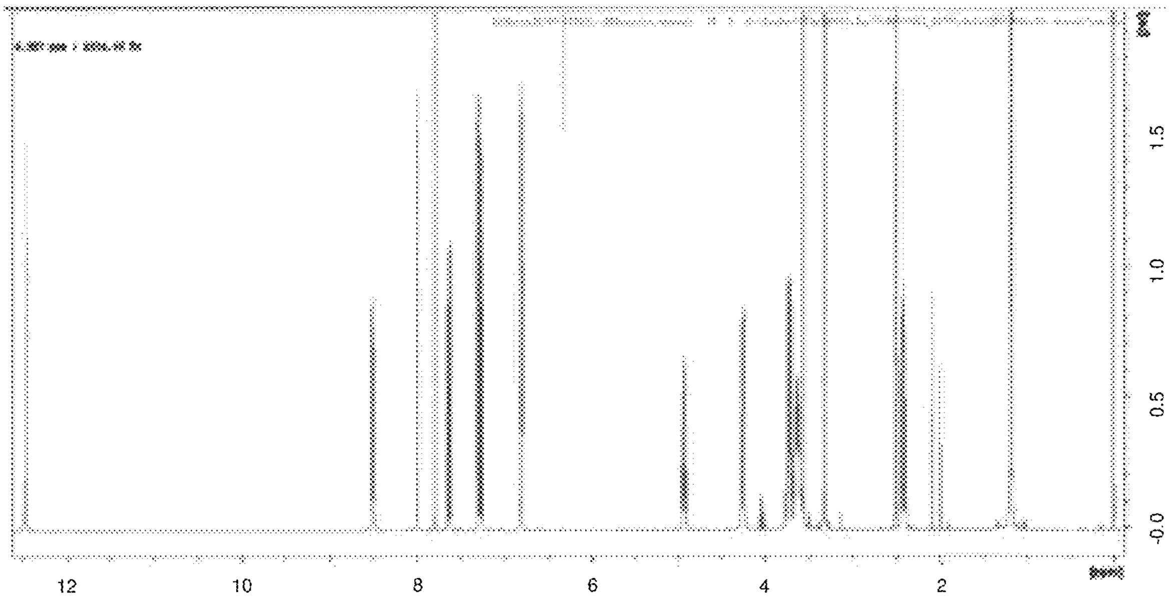
FIG. 10 is an $^1$H NMR spectra of the second crystalline form of the compound of formula (I).

FIG. 10 shows the $^1$H NMR spectrum of the second crystalline form of the compound of formula (I).

Polarized Light Microscopy (PLM).

Figure 1B:
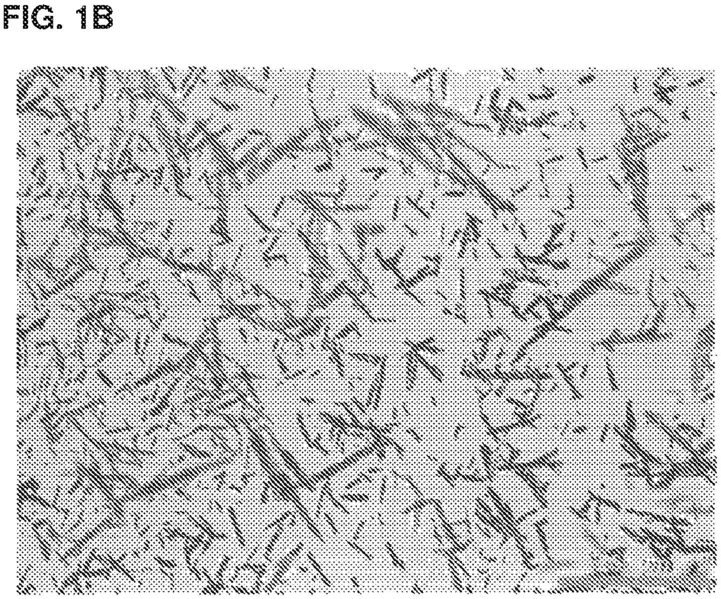

Optical microscopy was performed using the Nikon Eclipse E400 Optical Microscope equipped with 2, 4, 10, 25, and 40× objective lens. The microscope is coupled with a QImaging digital camera. The camera is controlled by the proprietary QCapture Pro 7 software. The camera software measurement tool is calibrated using a calibration slide (Pyser-SGI S8 Micrometer scale 1 mm/0.01 mm). Samples were prepared either by distributing a powder over a microscope slide with mineral oil or by placing a drop of suspension directly onto a microscope slide. A cover slip was then placed on top. FIG. 1A shows a microscopic image of the first crystalline form of the compound of formula (I) and FIG. 1B shows a microscopic image of the second crystalline form of the compound of formula (I).

The First Crystalline Form of the Compound of Formula (I).

Optical microscopy showed the material consists mostly of fine particles less than 20 μm in length (FIG. 1A).

The Second Crystalline Form of the Compound of Formula (I).

Optical microscopy showed the material consists mostly of columnar crystals of up to 250 μm in length (FIG. 1B).

Example 3. Screening for Stable Forms Via Slurry Conversions

Single Solvent Slurry Screen.

A single solvent slurry screen was conducted to allow phase transformations of the second crystalline form of the compound of formula (I) to a more thermodynamically stable form in single solvent systems (Table 7). Saturated solutions were prepared with additional crystalline compound (e.g., the second crystalline form of the compound of formula (I)) in quantities sufficient to perform solid state analysis on resulting samples. Magnetic stirrers were added to vials, and the suspensions were allowed to stir at room temperature for 4 days. Solid samples generated were analyzed via XRPD to assess crystallinity and crystal structure.

TABLE 7

| Solvent | Crystal Structure |
|---|---|
| Methanol | Second crystalline form of the compound of formula (I) |
| Ethanol | Second crystalline form of the compound of formula (I) |
| Isopropanol | Second crystalline form of the compound of formula (I) |
| 2-Butanol | Second crystalline form of the compound of formula (I) |
| Acetone | Second crystalline form of the compound of formula (I) |
| MEK | Second crystalline form of the compound of formula (I) |
| Acetonitrile | Second crystalline form of the compound of formula (I) |
| MTBE | Second crystalline form of the compound of formula (I) |
| Ethyl acetate | Second crystalline form of the compound of formula (I) |
| Isopropyl acetate | Second crystalline form of the compound of formula (I) |
| 2-MeTHF | Second crystalline form of the compound of formula (I) |
| THF | Dissolved |
| Toluene | Second crystalline form of the compound of formula (I) |
| Xylenes | Second crystalline form of the compound of formula (I) |
| Water | Second crystalline form of the compound of formula (I) |
| n-Heptane | Second crystalline form of the compound of formula (I) |

Figure 11:
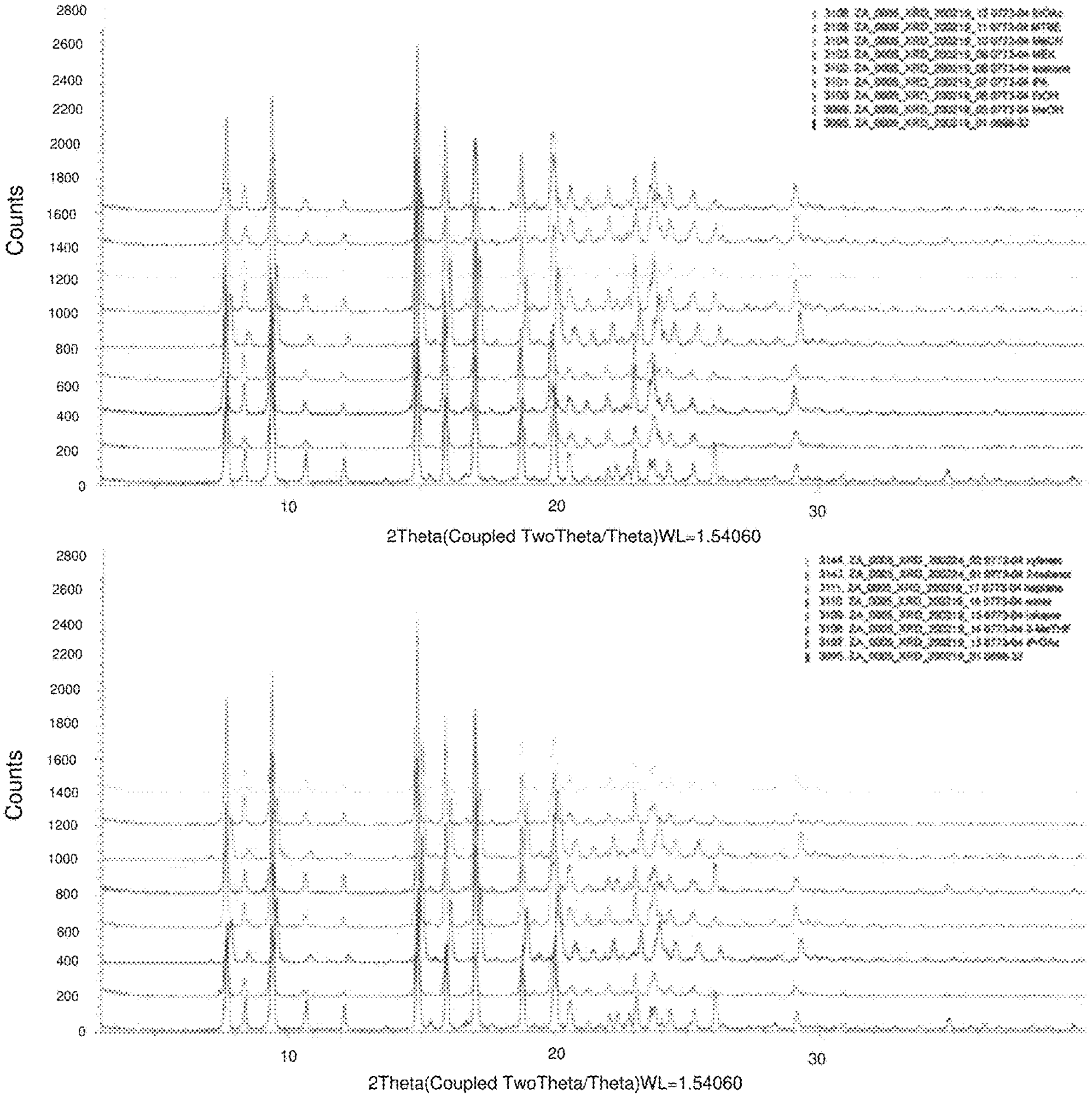
FIG. 11 is an overlay of the XRPD patterns obtained from solid samples isolated from single solvent slurries of the second crystalline form of the compound of formula (I) (traces from top to bottom: solid from ethyl acetate, solid from methyl tert-butyl ether, solid from acetonitrile, solid from methyl ethyl ketone, solid from acetone, solid from isopropanol, solid from ethanol, solid from methanol, the second crystalline form of the compound of formula (I), solid from xylenes, solid from 2-butanol, solid from heptane, solid from water, solid from toluene, solid from 2-methyl tetrahydrofuran, solid from isopropyl acetate, and the second crystalline form of the compound of formula (I)). Each diffraction pattern displays the characteristic reflections of the second crystalline form of the compound of formula (I), with reflections at 7.5 °2θ, 9.5 °2θ, 15.0 °2θ, and 17.0 °2θ.

The second crystalline form of the compound of formula (I) could not be slurried in THF as the solubility is extremely high and the API dissolved. Solid samples were obtained from slurries in all other solvents screened. XRPD analysis showed that each solid sample exhibits the same diffraction pattern, and hence the same crystal structure, as the second form crystalline form of the compound of formula (I) (FIG. 11). Each diffraction pattern displays the characteristic reflections of the second crystalline form of the compound of formula (I), with reflections at 7.5 °2θ, 9.5 °2θ, 15.0 °2θ, and 17.0 °2θ.

Temperature Cycled Single Solvent Slurry Screen.

Figure 12:
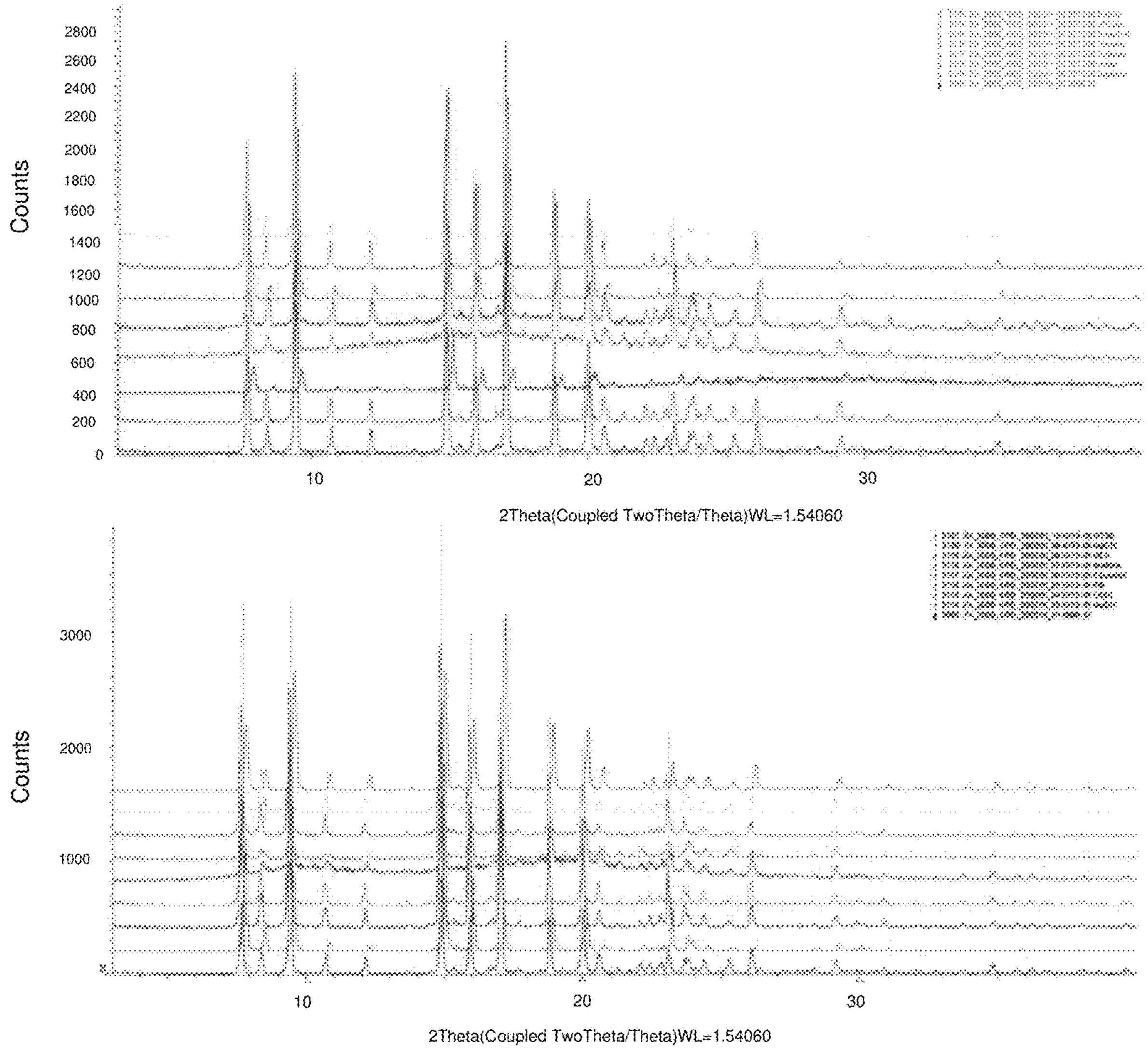
FIG. 12 is an overlay of the XRPD patterns obtained from solid samples isolated from temperature cycled single solvent slurries of the second crystalline form of the compound of formula (I) (traces from top to bottom: solid from ethyl acetate, solid from isopropyl acetate, solid from 2-methyl tetrahydrofuran, solid from toluene, solid from xylenes, solid from water, solid from heptane, the second crystalline form of the compound of formula (I), solid from methyl tert-butyl ether, solid from acetonitrile, solid from methyl ethyl ketone, solid from acetone, solid from 2-butanol, solid from isopropanol, solid from ethanol, solid from methanol, and the second crystalline form of the compound of formula (I)). Each diffraction pattern displays the characteristic reflections of the second crystalline form of the compound of formula (I), with reflections at 7.5 °2θ, 9.5 °2θ, 15.0 °2θ, and 17.0 °2θ, although samples obtained from 2-butanol and xylenes exhibited poor crystallinity.

A single solvent slurry screen was conducted to allow phase transformations of the second crystalline form of the compound of formula (I) to a more thermodynamically stable form in single solvent systems (Table 8). Saturated solutions were prepared with additional crystalline compound (e.g., the second crystalline form of the compound of formula (I)) in quantities sufficient to perform solid state analysis on resulting samples. Magnetic stirrers were added to vials, and the suspensions were cycled between 50° C. and 5° C. for three cycles with agitation. Solid samples generated were analyzed via XRPD to assess crystallinity and crystal structure. The second crystalline form of the compound of formula (I) could not be slurried in THE as the solubility is extremely high and the API dissolved. Solid samples were obtained from slurries in all other solvents screened. XRPD analysis showed that each solid sample exhibits the same diffraction pattern, and hence the same crystal structure, as the second form crystalline form of the compound of formula (I) (FIG. 12). Each diffraction pattern displays the characteristic reflections of the second crystalline form of the compound of formula (I), with reflections at 7.5 °2θ, 9.5 °2θ, 15.0 °2θ, and 17.0 °2θ, although samples obtained from 2-butanol and xylenes exhibited poor crystallinity.

TABLE 8

| Solvent | Crystal Structure |
|---|---|
| Methanol | Second crystalline form of the compound of formula (I) |
| Ethanol | Second crystalline form of the compound of formula (I) |
| Isopropanol | Second crystalline form of the compound of formula (I) |
| 2-Butanol | Second crystalline form of the compound of formula (I) (low crystallinity) |
| Acetone | Second crystalline form of the compound of formula (I) |
| MEK | Second crystalline form of the compound of formula (I) |
| Acetonitrile | Second crystalline form of the compound of formula (I) |
| MTBE | Second crystalline form of the compound of formula (I) |
| Ethyl acetate | Second crystalline form of the compound of formula (I) |
| Isopropyl acetate | Second crystalline form of the compound of formula (I) |
| 2-MeTHF | Second crystalline form of the compound of formula (I) |
| THF | Dissolved |
| Toluene | Second crystalline form of the compound of formula (I) |
| Xylenes | Second crystalline form of the compound of formula (I) (low crystallinity) |
| Water | Second crystalline form of the compound of formula (I) |
| n-Heptane | Second crystalline form of the compound of formula (I) |

Binary Solvent Slurry Screen.

A binary solvent slurry screen was conducted to allow phase transformations of the second crystalline form of the compound of formula (I) to a more thermodynamically stable form in binary solvent systems (Table 9). Solvent combinations were selected based on solvent properties, functionality, and miscibility. Saturated solutions were prepared in 50/50 (v/v) solvent mixtures with additional crystalline compound (e.g., the second crystalline form of the compound of formula (I)) in quantities sufficient to perform solid state analysis on resulting samples. Magnetic stirrers were added to vials, and the suspensions were allowed to stir at room temperature for 5 days.

TABLE 9

| Solvent 1 | Solvent 2 | Crystal Structure |
|---|---|---|
| Methanol | Toluene | Second crystalline form of the compound of formula (I) |
| Methanol | THF | Dissolved |
| Methanol | Acetonitrile | Second crystalline form of the compound of formula (I) |
| Methanol | Ethyl acetate | Second crystalline form of the compound of formula (I) |
| Toluene | THF | Second crystalline form of the compound of formula (I) |
| Toluene | Acetonitrile | Second crystalline form of the compound of formula (I) |
| Toluene | Ethyl acetate | Second crystalline form of the compound of formula (I) |
| n-Heptane | THF | Second crystalline form of the compound of formula (I) |
| n-Heptane | Ethyl acetate | Second crystalline form of the compound of formula (I) |
| THF | Acetonitrile | Second crystalline form of the compound of formula (I) |
| THF | Ethyl acetate | Second crystalline form of the compound of formula (I) (low crystallinity) |
| Acetonitrile | Ethyl acetate | Second crystalline form of the compound of formula (I) |

Solid samples were obtained from slurries in all solvent mixtures screened except methanol/THF as the solubility was high. XRPD analysis showed that each solid sample exhibits the same diffraction pattern, and hence the same crystal structure, as the second crystalline form of the compound of formula (I). Each diffraction pattern displays the characteristic reflections of the second crystalline form of the compound of formula (I), with reflections at 7.5 °2θ, 9.5 °2θ, 15.0 °2θ, and 17.0 °2θ, although samples obtained from THF/ethyl acetate exhibited poor crystallinity.

Example 4. Screening for Metastable Forms Via Nucleation

Excess compound of formula (I) (e.g., the second crystal form of the compound of formula (I)) was slurried in each solvent at 45° C. for 2 hours before separating the solids and liquors by centrifugation. The liquors were transferred to fresh vials for low temperature evaporation, high temperature evaporation and cooling crystallization screen.

Low Temperature Evaporation Screen.

Figure 13:
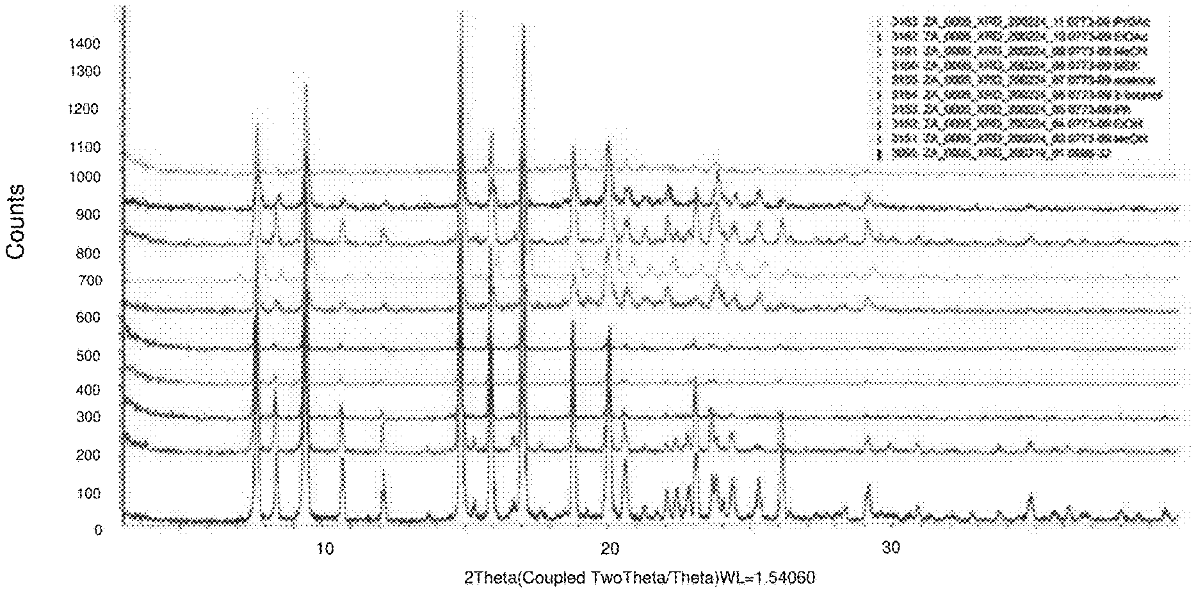
FIG. 13 is an overlay of the XRPD patterns obtained from solid samples isolated from a low temperature evaporation screen of the second crystalline form of the compound of formula (I) in various solvents, generated by slow solvent evaporation under ambient conditions (traces from top to bottom: solid from isopropyl acetate, solid from ethyl acetate, solid from acetonitrile, solid from methyl ethyl ketone, solid from acetone, solid from 2-butanol, solid from isopropanol, solid from ethanol, solid from methanol, and the second crystalline form of the compound of formula (I)). Each diffraction pattern displays the characteristic reflections of the second crystalline form of the compound of formula (I), with reflections at 7.5 °2θ, 9.5 029, 15.0 °2θ, and 17.0 °2θ, although samples obtained from tetrahydrofuran and 2-methyl tetrahydrofuran resulted in an oil.

A low temperature evaporation screen was conducted to isolate crystal structures that may form as a result of super-saturation generated by slow solvent evaporation under ambient conditions (Table 10). Sufficient material for analysis was not obtained from toluene, xylenes, water, and n-heptane. The evaporation of THF and 2-MeTHF resulted in an oil, and the second crystalline form of the compound of formula (I) was formed in all other solvents (FIG. 13).

TABLE 10

| Solvent | Crystal Structure |
|---|---|
| Methanol | Second crystalline form of the compound of formula (I) |
| Ethanol | Second crystalline form of the compound of formula (I) |
| Isopropanol | Second crystalline form of the compound of formula (I) |
| 2-Butanol | Second crystalline form of the compound of formula (I) |
| Acetone | Second crystalline form of the compound of formula (I) |
| MEK | Second crystalline form of the compound of formula (I) |
| Acetonitrile | Second crystalline form of the compound of formula (I) |
| MTBE | Second crystalline form of the compound of formula (I) |
| Ethyl acetate | Second crystalline form of the compound of formula (I) |
| Isopropyl acetate | Second crystalline form of the compound of formula (I) |
| 2-MeTHF | Oil |
| THF | Oil |
| Toluene | N/A |
| Xylenes | N/A |
| Water | N/A |
| n-Heptane | N/A |

High Temperature Evaporation Screen.

Figure 14:
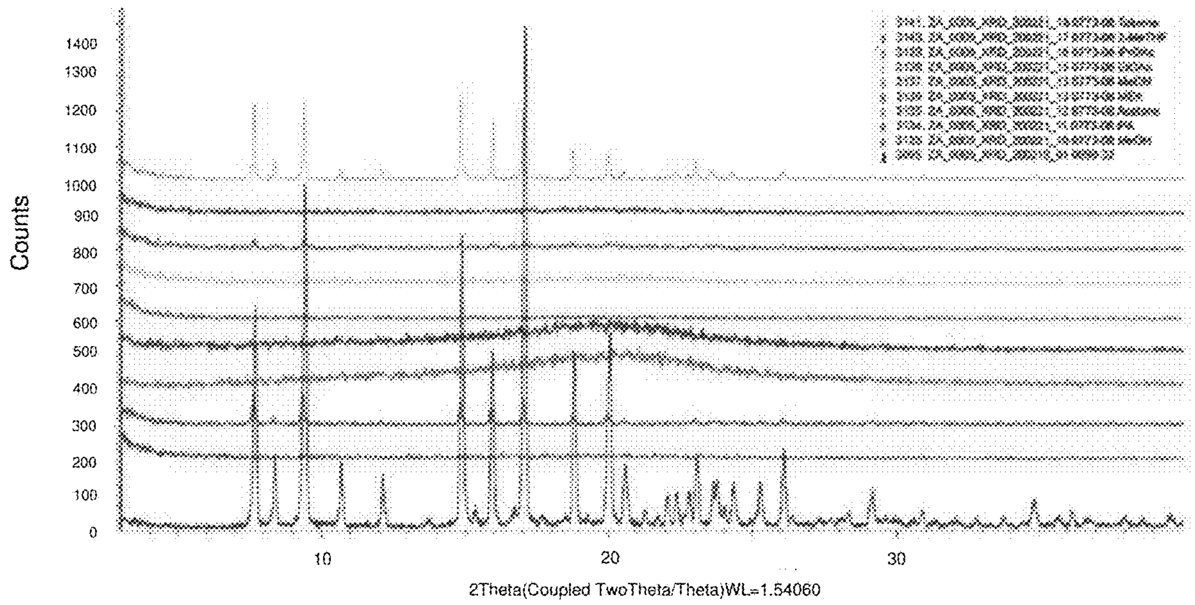
FIG. 14 is an overlay of the XRPD patterns obtained from solid samples isolated from a high temperature evaporation screen of the second crystalline form of the compound of formula (I) in various solvents (traces from top to bottom: solid from toluene, solid from 2-methyl tetrahydrofuran, solid from isopropyl acetate, solid from ethyl acetate, solid from acetonitrile, solid from methyl ethyl ketone, solid from acetone, solid from isopropanol, solid from methanol, and the second crystalline form of the compound of formula (I)). The liquors were heated from 45° C. to 50° C. to ensure all solids were fully dissolved before the solvent was evaporated at 50° C. XRPD analysis showed that material produced by the evaporation of isopropanol, isopropyl acetate, and toluene formed the second crystalline form of the compound of formula (I). All other solid samples were amorphous.

A high temperature evaporation screen was conducted to isolate metastable phases that may form as a result of super-saturation generated by rapid solvent evaporation (Table 11). The liquors were heated from 45° C. to 50° C. to ensure all solids were fully dissolved before the solvent was evaporated at 50° C. A controlled air flow across the vials of −0.8 bar was generated using the Crystal Breeder. Once evaporation was complete, solid samples were analyzed using XRPD to assess crystallinity and crystal structure (FIG. 14).

TABLE 11

| Solvent | Crystal Structure |
|---|---|
| Methanol | Amorphous |
| Ethanol | N/A |
| Isopropanol | Second crystalline form of the compound of formula (I) |
| 2-Butanol | N/A |
| Acetone | Amorphous |
| MEK | Amorphous |
| Acetonitrile | Amorphous |

TABLE 11-continued

| Solvent | Crystal Structure |
|---|---|
| MTBE | N/A |
| Ethyl acetate | Amorphous |
| Isopropyl acetate | Second crystalline form of the compound of formula (I) |
| 2-MeTHF | Oil |
| THF | Oil |
| Toluene | Second crystalline form of the compound of formula (I) |
| Xylenes | N/A |
| Water | N/A |
| n-Heptane | N/A |

The compound of formula (I) converted to an oil phase after the evaporation of 2-MeTHF and THF. Sufficient material for analysis was not obtained from ethanol, 2-butanol, MTBE, xylenes, water, and n-heptane. Solid samples were obtained from the evaporation of all other solvents screen. XRPD analysis showed that material produced by the evaporation of isopropanol, isopropyl acetate, and toluene formed the second crystalline form of the compound of formula (I). All other solid samples were amorphous.

Cooling Crystallization Screen.

A cooling crystallization screen was conducted to isolate metastable phases that may form as a result of supersaturation generated by rapid decrease in temperature (Table 12). The liquors were heated to 50° C. to ensure all solids were fully dissolved. The vials were then cooled to 5° C. at 20° C./minute and held at low temperature overnight. Any solid samples generated were isolated and analyzed via XRPD to assess crystallinity and crystal structure.

TABLE 12

| Solvent | Crystal Structure |
|---|---|
| Methanol | Second crystalline form of the compound of formula (I) |
| Ethanol | Second crystalline form of the compound of formula (I) |
| Isopropanol | Second crystalline form of the compound of formula (I) |
| 2-Butanol | N/A |
| Acetone | N/A |
| MEK | Second crystalline form of the compound of formula (I) |
| Acetonitrile | Second crystalline form of the compound of formula (I) |
| MTBE | N/A |
| Ethyl acetate | Second crystalline form of the compound of formula (I) |
| Isopropyl acetate | N/A |
| 2-MeTHF | N/A |
| THF | N/A |
| Toluene | N/A |
| Xylenes | N/A |
| Water | N/A |
| n-Heptane | N/A |

Figure 15:
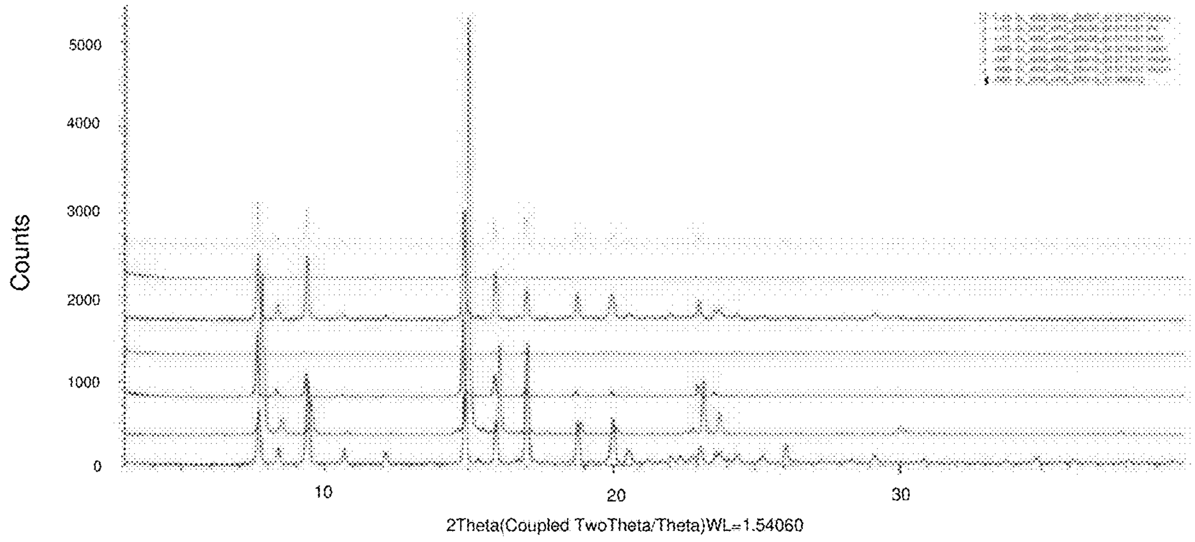
FIG. 15 is an overlay of the XRPD patterns obtained from solid samples isolated by crash cooling in ethyl acetate, isopropanol, methyl ethyl ketone, ethanol, methanol, and acetonitrile (traces from top to bottom, with the bottom trace being the second crystalline form of the compound of formula (I)). The XRPD patterns are consistent with the second crystalline form of the compound of formula (I).

Small quantities of solid samples were obtained by crash cooling in methanol, ethanol, isopropanol, MEK, acetonitrile, and ethyl acetate. XRPD analysis showed that each solid sample is consistent with the second crystalline form of the compound of formula (I) (FIG. 15). Crystallinity appeared low in samples from ethanol and isopropanol; however, this could be due to small sample size. In all other solvents screened, the compound of formula (I) remained in solution, indicating the maximum concentration generated in this study does not approach the meta-stable zone boundary at 5° C.

Hydrate Screen.

A hydrate screen was conducted to observe solvated or hydrated structures that may be formed from the compound of formula (I) in solvent/water mixtures (Table 13). Solvents were selected based on miscibility with water. 0.5 mL aliquots of solvent were added to approximately 50 mg of the second crystalline form of the compound of formula (I) until the solids were dissolved in the minimum solvent required. 1 mL aliquots of water were added until a cloud point was observed or until 20 mL had been added. The vials were heated to 50° C. and cooled to room temperature. After stirring at room temperature for 2 days, the solvent was allowed to evaporate to increase the material available for characterization. When sufficient crystals had formed, a sample was removed for initial XRPD analysis. The remaining solvent was evaporated until dry to produce a larger sample for further characterization, with the crystals already present acting as a seed.

TABLE 13

| Solvent/ water | Solvent:water ratio | Crystal Structure Wet | Crystal Structure Dry |
|---|---|---|---|
| Methanol | 1:1 | Second crystalline form + reflections | Second crystalline form |
| Ethanol | 1:1 | Second crystalline form | Second crystalline form |
| Isopropanol | 3:2 | Second crystalline form | Second crystalline form |
| Acetonitrile | 1:2 | Second crystalline form | Second crystalline form |
| Acetone | 1:1 | Second crystalline form | Second crystalline form |
| THF | 1:2 | Amorphous | Amorphous |

Figure 16:
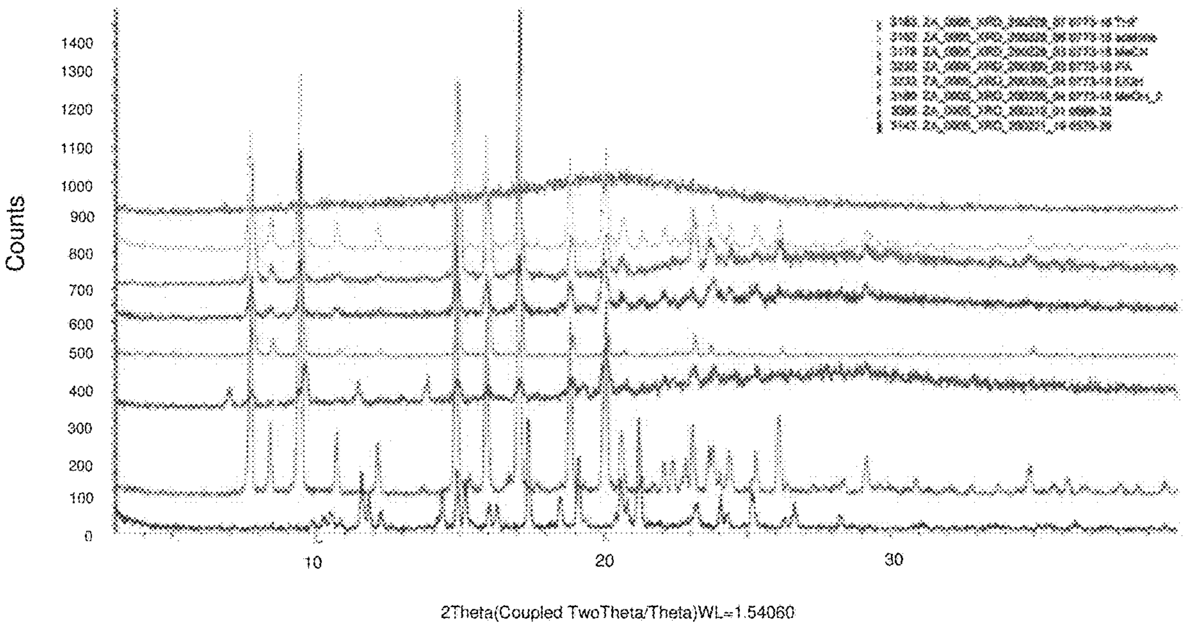
FIG. 16 is an overlay of the XRPD patterns obtained from solid samples isolated after a hydrate screen (traces from top to bottom: solid from tetrahydrofuran/water, solid from acetone/water, solid from acetonitrile/water, solid from isopropanol/water, solid from ethanol/water, solid from methanol/water, the second crystalline form of the compound of formula (I), and the first crystalline form of the compound of formula (I)). The XRPD patterns were performed on wet samples to ensure any alterations resulting from drying were observed. The XRPD patterns are consistent with the second crystalline form of the compound of formula (I), except the XRPD pattern of the solid sample from tetrahydrofuran/water, which is amorphous.
Figure 17:
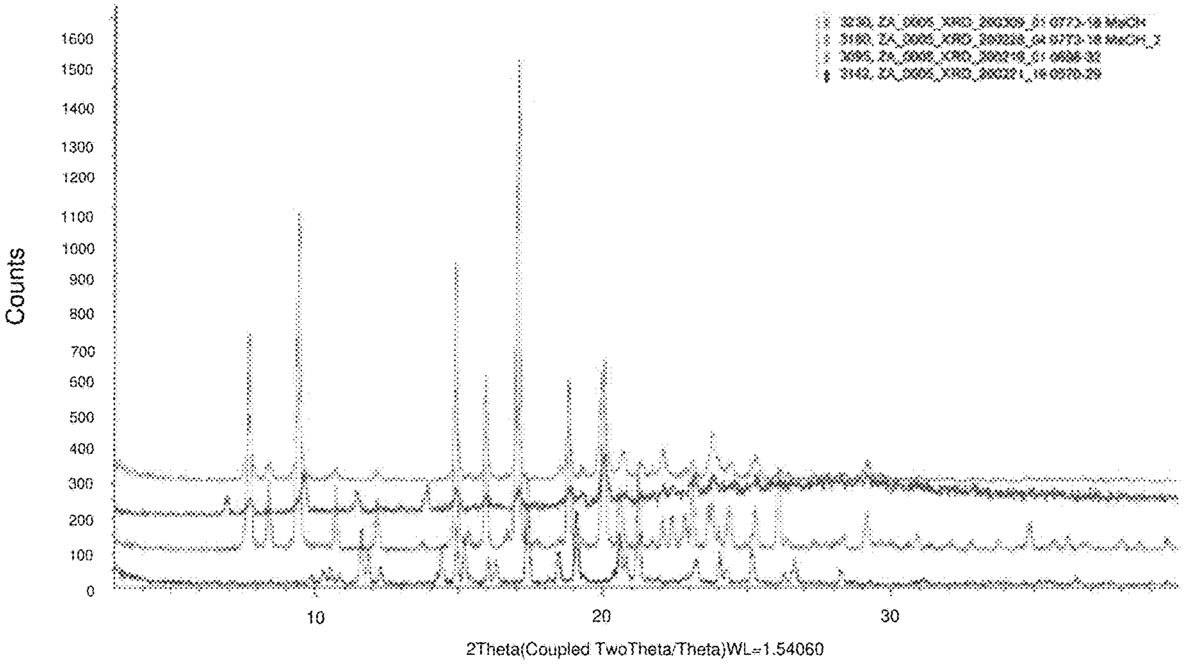
FIG. 17 is an overlay of the XRPD patterns performed on wet and dry samples of the solid obtained from a hydrate screen with methanol/water with the XRPD patterns of the first and second crystalline forms of the compound of formula (I) (black and magenta traces, respectively). The XRPD pattern of the wet solid obtained from methanol/water (trace in blue), which exhibited an additional reflection at 11.5 °2θ, corresponding with the first crystalline form of the compound of formula (I). The dry solid (trace in green) exhibited only peaks corresponding with the second crystalline form of the compound of formula (I).

Initial analysis was performed on wet samples to ensure any alterations resulting from drying were observed. XRPD showed that the sample obtained from THF/water was amorphous and all other samples have the second crystalline form of the compound of formula (I) (FIG. 16). However, the sample obtained from methanol/water exhibits additional reflections at 11.5 °2θ (which may correspond to the first crystalline form of the compound of formula (I)) and 7 °2θ (which was not assigned). XRPD analysis on the dry sample showed only the second crystalline form of the compound of formula (I) remains (FIG. 17).

Example 5. Competitive Suspension Equilibration Study

A competitive suspension equilibration study was carried out to identify the relative stability of the two crystalline forms of the compound of formula (I) in aqueous and organic solvent systems. Competitive suspension equilibration experiments were conducted in ethyl acetate, 50% methanol/water (v/v) and 50% acetonitrile/water (v/v) at room temperature and 60° C. The second crystalline form of the compound of formula (I) was added to each solvent to create a saturated solution. Further crystalline forms of the compound of formula (I) (e.g., the first and second crystalline forms of the compound of formula (I)) were added for conversion material and to act as seeds. Each suspension was allowed to stir for 7 or 14 days, and were analyzed via XRPD to determine which form the solids had converted to. Table 14 summarizes the competitive suspension equilibration conditions.

TABLE 14

| Solvent | Temperature | Crystal Structure |
|---|---|---|
| Ethyl acetate | room temperature | Second crystalline form of the compound of formula (I) |

TABLE 14-continued

| Solvent | Temperature | Crystal Structure |
|---|---|---|
| Ethyl acetate | 60° C. | Second crystalline form of the compound of formula (I) |
| Methanol | room temperature | Second crystalline form of the compound of formula (I) |
| Methanol | 60° C. | Second crystalline form of the compound of formula (I) |
| Acetonitrile | room temperature | Second crystalline form of the compound of formula (I) |
| Acetonitrile | 60° C. | Second crystalline form of the compound of formula (I) |
| Methanol/water* | room temperature | First + second crystalline forms of the compound of formula (I) |
| Methanol/water* | 60° C. | First + second crystalline forms of the compound of formula (I) |
| Acetonitrile/water | room temperature | First + second crystalline forms of the compound of formula (I) |
| Acetonitrile/water | 60° C. | First + second crystalline forms of the compound of formula (I) |

*Suspension stirred for 14 days

Figure 18:
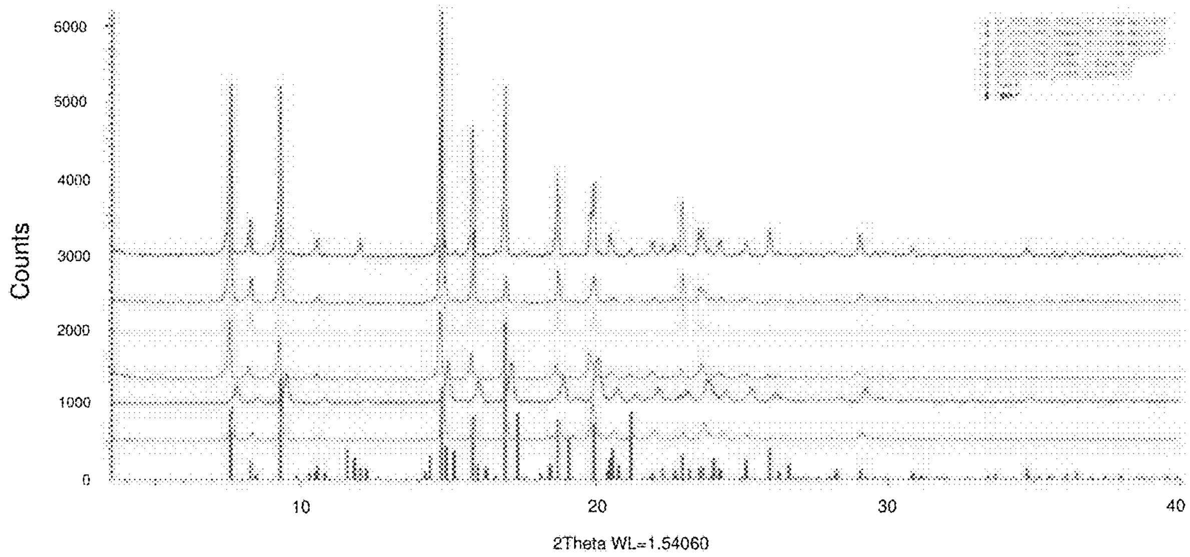
FIG. 18 is an overlay of the XRPD patterns obtained from solid samples stirred in acetonitrile at 60° C., acetonitrile at room temperature, methanol at 60° C., methanol at room temperature, ethyl acetate at 60° C., and ethyl acetate at room temperature. The bottom traces are the first and second crystalline forms of the compound of formula (I) (black and magenta traces, respectively).
Figure 19:
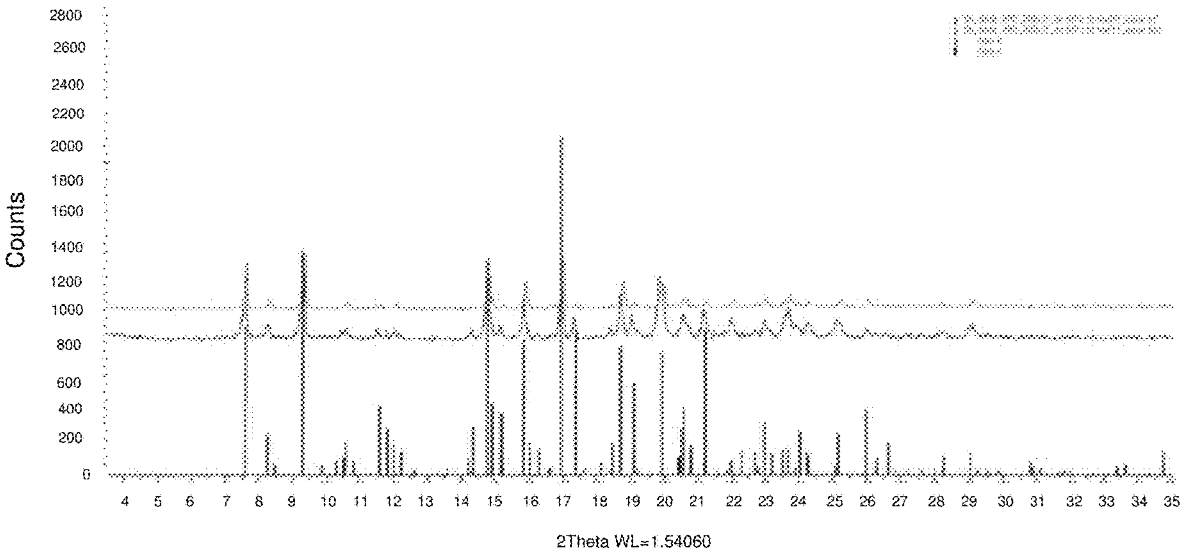
FIG. 19 is an overlay of the XRPD patterns of solids stirred for 14 days in methanol/water (green trace: solid from methanol/water, room temperature; blue trace: solid from methanol/water, 60° C.; black trace: the first crystalline form of the compound of formula (I); magenta trace: the second crystalline form of the compound of formula (I)). These samples showed a majority of the second crystalline form, with reflections characteristic of the first crystalline form visible at 14.4 °2θ and 17.4 °2θ.
Figure 20:
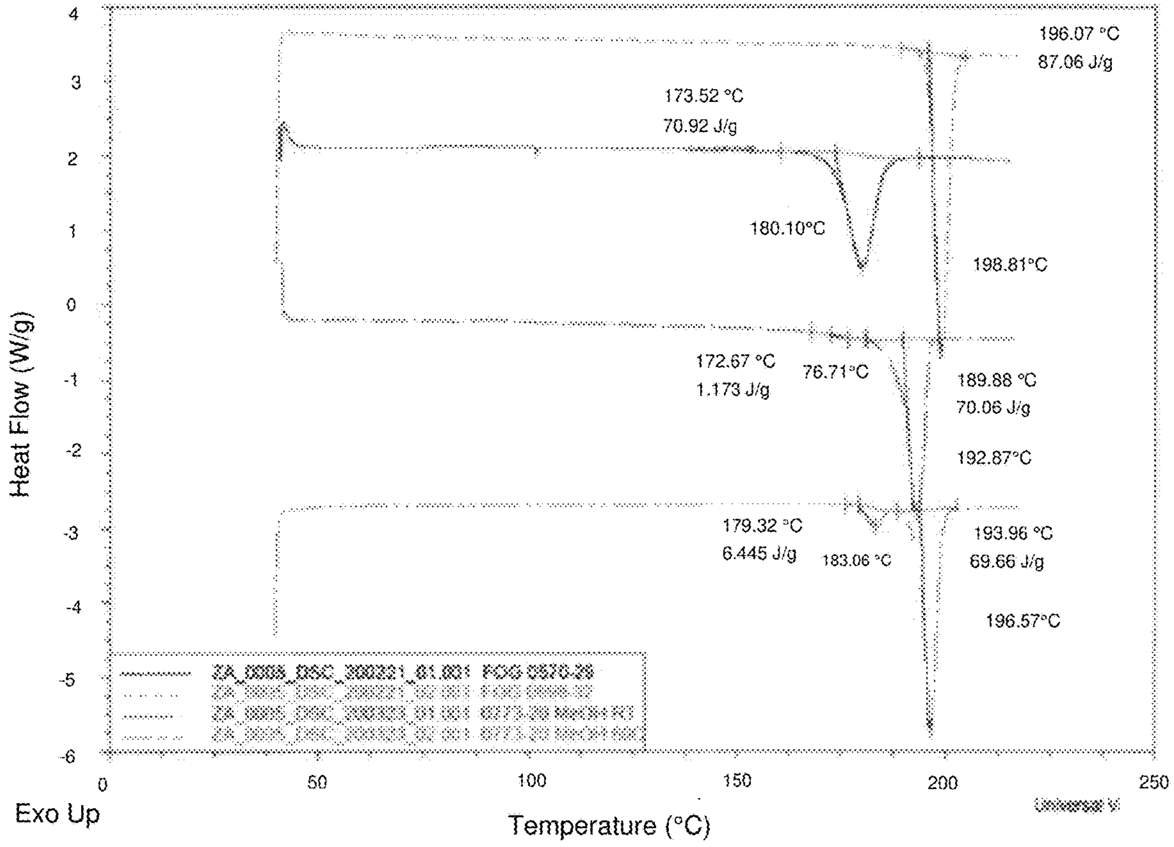
FIG. 20 is an overlay of DSC traces of the first and second crystalline forms (black and magenta traces, respectively) of the compound of formula (I) with samples stirred in methanol/water at room temperature and 60° C. (blue and green traces, respectively).
Figure 21:
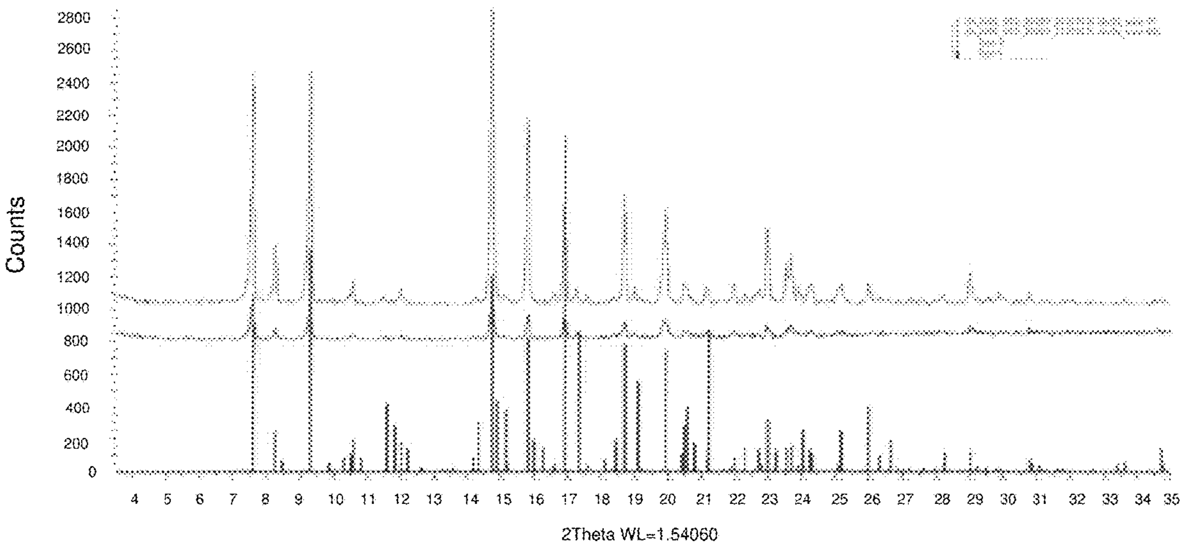
FIG. 21 is an overlay of the XRPD patterns of solids stirred for 7 days in acetonitrile/water (green trace: solid from acetonitrile/water, 60° C.; blue trace: solid from acetonitrile/water, room temperature; black trace: the first crystalline form of the compound of formula (I); magenta trace: the second crystalline form of the compound of formula (I)).
Figure 22:
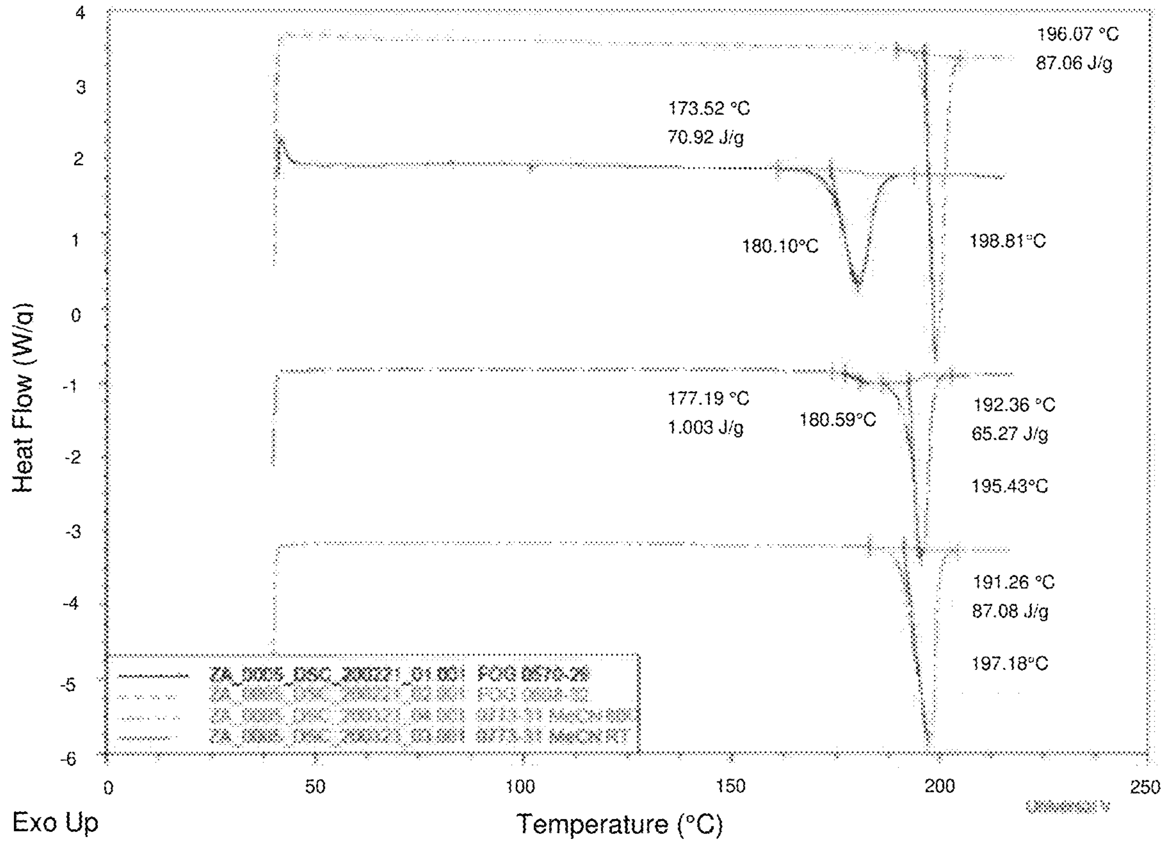
FIG. 22 is an overlay of DSC traces of the first and second crystalline forms (black and magenta traces, respectively) of the compound of formula (I) with samples stirred in acetonitrile/water at room temperature and 60° C. (blue and green traces, respectively).

XRPD analysis showed that the compound of formula (I) fully converted to the second crystalline form within seven days of stirring both crystalline forms at room temperature and 60° C. in ethyl acetate, methanol, and acetonitrile (FIG. 18). However, stirring in aqueous solvents did not result in the conversion of either crystalline form to the other. XRPD analysis of solids stirred for 14 days in methanol/water showed a majority of the second crystalline form, with reflections characteristic of the first crystalline form visible at 14.4 °2θ and 17.4 °2θ (FIG. 19). Although it appears from this analysis that the second crystalline form is the dominant form, this may be due to a greater proportion of the second crystalline form in the input material. DSC analysis also showed a mixture of the first and second crystalline forms, although there is a shift in the melting point for each form due to the impurity presence of the competing structures (FIG. 20). Similarly, XRPD analysis of solids stirred for seven days in acetonitrile/water showed the second crystalline form of the compound of formula (I) with additional reflections at 14.4 °2θ and 17.4 °2θ, corresponding to the first crystalline form of the compound of formula (I) (FIG. 21). DSC analysis showed the first and second crystalline forms of the compound of formula (I) are present when stirred at room temperature; however, only the first crystalline form was detected when stirred at 60° C. (FIG. 22).

Example 6. Salt and Co-Crystal Screen

A salt screen of the compound of formula (I) was carried out with a variety of counterions to identify crystalline salt and co-crystal forms that may be used for purification purposes or to influence the solubility and stability of the final solid form.

The potential for salt and co-crystal crystallization was evaluated via liquid assisted grinding, a slow evaporation screen, slurrying, and temperature cycling of the compound of formula (I) combined with 15 counterions, and in a selection of 16 solvents (Table 15). This allowed the investigation to survey a broad array of conditions that may influence the formation and stability of crystalline salt and co-crystal forms.

TABLE 15

| Solvents | Counterions |
|---|---|
| Methanol | Benzenesulfonic acid (BSA) |
| Ethanol/water | p-toluenesulfonic acid (TSA) |
| Isopropanol | Hydrochloric acid (HCl) |
| 2-Butanol | Sulfuric acid |
| Acetone | Malonic acid |
| Acetonitrile | Oxalic acid |
| Ethyl acetate | Phosphoric acid |
| Isopropyl acetate | Ethane disulfonic acid (EdSA) |
| Toluene | Serine |
| Xylenes | Lysine |
| THF | Glutamic acid |
| MTBE | Magnesium sulfate |
| | Sodium hydroxide |
| | Potassium hydroxide |

Liquid Assisted Grinding Screen.

Counterions were screened via liquid assisted grinding to encourage the formation of co-crystals by minimizing the influence of solvent-molecule interactions. Approximately 50 mg of the second crystalline form of the compound of formula (I) was combined with 50 mg counterion in a mortar and pestle (Table 15). Two to five drops of methanol were added and the mixture was ground in periods of 2 minutes, followed by analysis by XRPD. Grinding was repeated as necessary.

All mixtures with acidic counterions formed a thick gel that showed mixtures of the input components of the second crystalline form of the formula of compound 1 and the respective acids once solidified. Mixtures with basic counterions remained as free flowing powders; however, the composition did not alter from the input components of the second crystalline form and the respective counterions.

Evaporative Screen.

A stock solution of the compound of formula (I) (0.1 M) was made in acetone, and 150 μL was dispensed into each well across two 96 well plates. 0.1 M stock solutions of each acid were made in methanol or water and dispensed at an equimolar ratio into 12 wells each. The solvent was allowed to evaporate until nitrogen flow, after which 250 μL of each crystallization solvent was added to the API/counterion mixtures and agitated to ensure mixing. The arrangement was such that, each row on the well plate represented a counterion and each column represented a crystallization solvent used for the salt screen. The wells were covered with parafilm with a pin hole, and the solvents were allowed to evaporate slowly at room temperature.

All powder samples obtained from the screen were analyzed via XRPD to identify crystalline salts. All other samples were first studied by PLM and where birefringence was observed, XRPD was also performed. Crystalline samples were grouped by their crystal structure and named by the counterion.

Many crystalline samples were identified as the second crystalline form of the compound of formula (I) or a mixture of the second crystalline form and the input counterion. Novel reflections were observed when the compound of formula (I) was combined with serine, magnesium sulfate, sodium hydroxide, and potassium hydroxide (Table 16). Novel crystal structures identified by XRPD were analyzed by DSC, and where possible by $^{1}H$ NMR.

TABLE 16

| | MeOH | EtOH/ water | iPrOH | 2- Butanol | MeCN | EtOAc | iPrOAc | Xylenes | MTBE |
|---|---|---|---|---|---|---|---|---|---|
| Serine | | | Serine + U | | | | | | Serine + U |
| $MgSO_4$ | Type B + MG1 | MG1 | MG1 | MG1 | Type B + MG1 | Type B + MG1 | Type B + MG1 | MG1 | MG1 |
| NaOH | | D | D | | D | D | D | D | D |
| KOH | | | | | | D | | | |

U = unidentified reflections;
D = degradant;
Type B = the second crystalline form of the compound of formula (I);
MG1 = magnesium salt.

Figure 23:
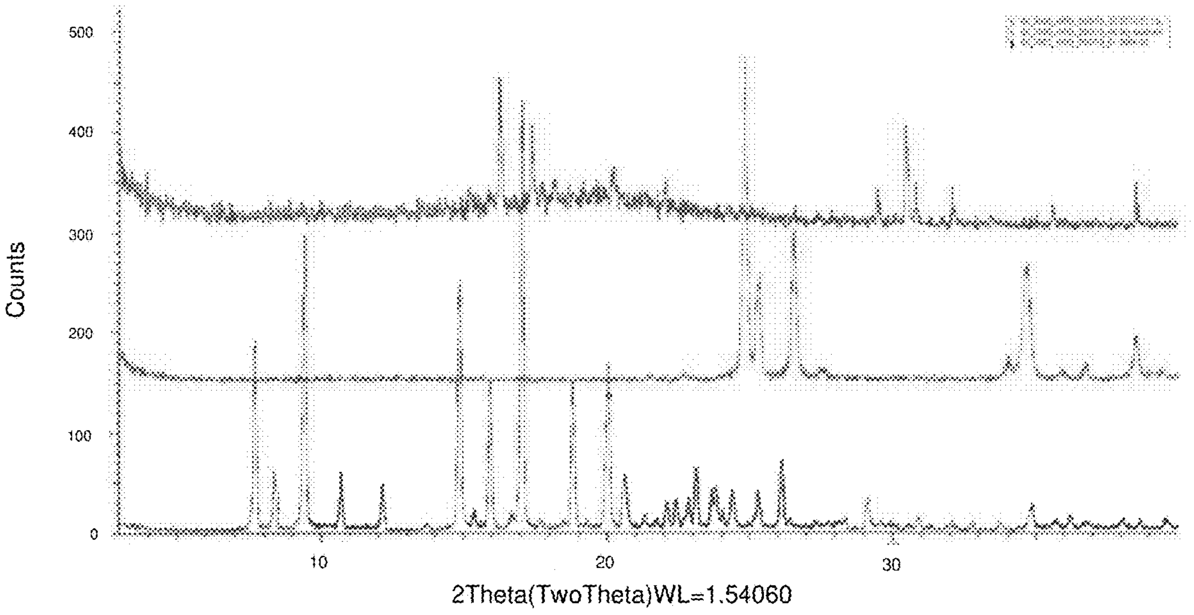
FIG. 23 is an overlay of XRPD patterns of the second crystalline form of the compound of formula (I) (black trace), magnesium sulfate (magenta trace), and the magnesium sulfate salt of the compound of formula (I) (blue trace).
Figure 24:
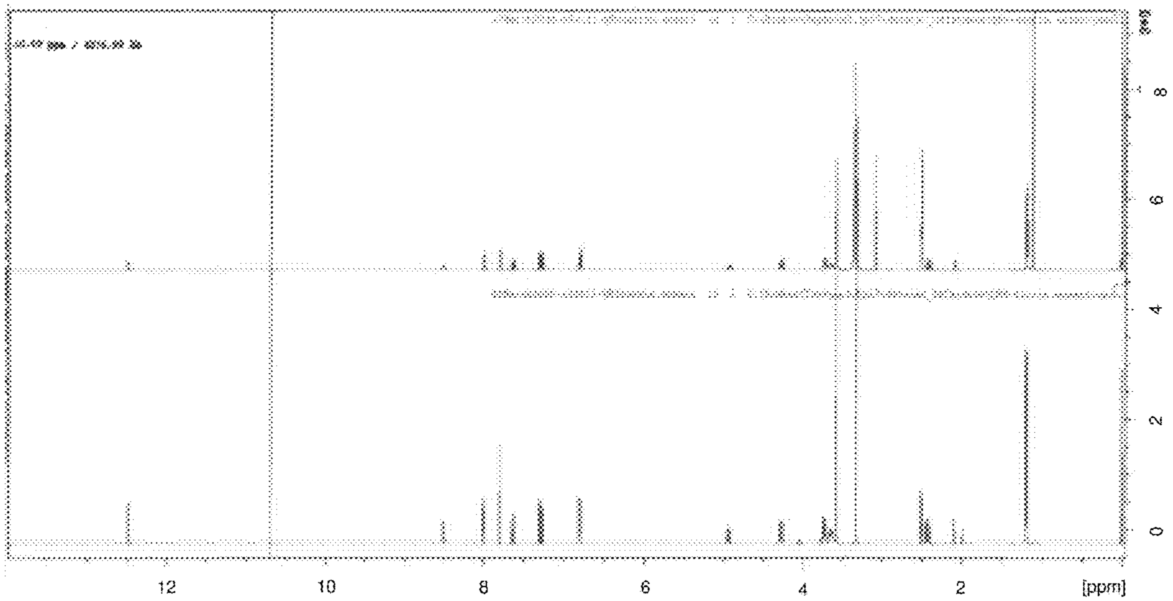
FIG. 24 is an overlay of $^{1}H$ NMR spectra of the second crystalline form of the compound of formula (I) (blue trace) and the magnesium sulfate salt of the compound of formula (I) (magenta trace).
Figure 25:
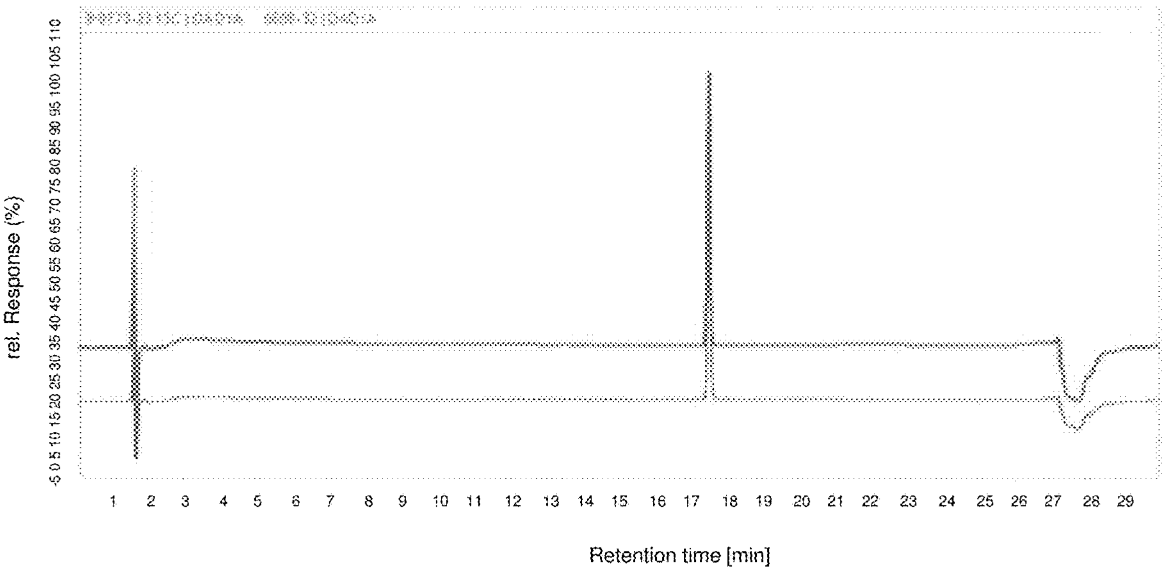
FIG. 25 is an overlay of HPLC traces of the compound of formula (I) (top trace) and the magnesium sulfate salt (bottom trace).
Figure 26:
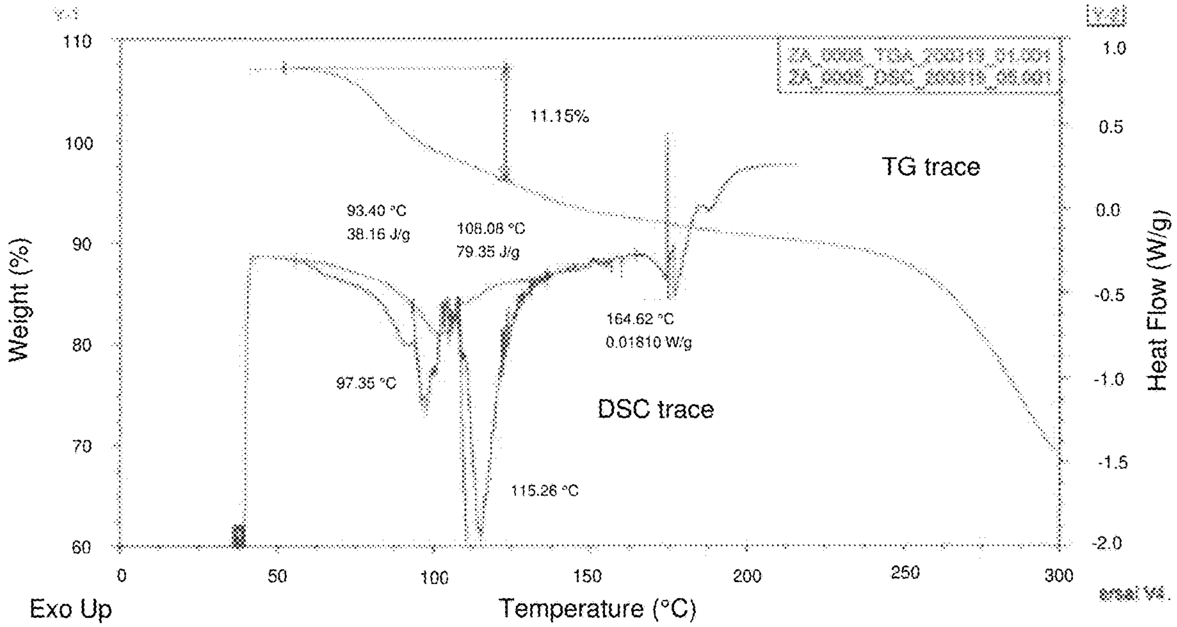
FIG. 26 is a plot showing TG and DSC traces for the magnesium sulfate salt of the compound of formula (I). The TG trace exhibited a significant low temperature weight loss of 11% (w/w) with a corresponding low temperature endotherm in the DSC trace suggesting solvent evaporation. A melting endotherm was observed at 115° C., followed by degradation from 165° C.

The XRPD analysis of solids formed by the combination of the compound of formula (I) with magnesium sulfate showed a new diffraction pattern, and hence, a new crystal structure (FIG. 23). No molecular degradation was visible via $^1$H NMR spectroscopy and HPLC analysis, indicating successful co-crystal formation, identified as MG1 (FIG. 24, FIG. 25). TG and DSC analysis showed significant low temperature weight loss of 11% (w/w) with a corresponding low temperature endotherm suggesting solvent evaporation (FIG. 26). A melting endotherm was observed at 115° C., followed by degradation from 165° C.

Figure 27:
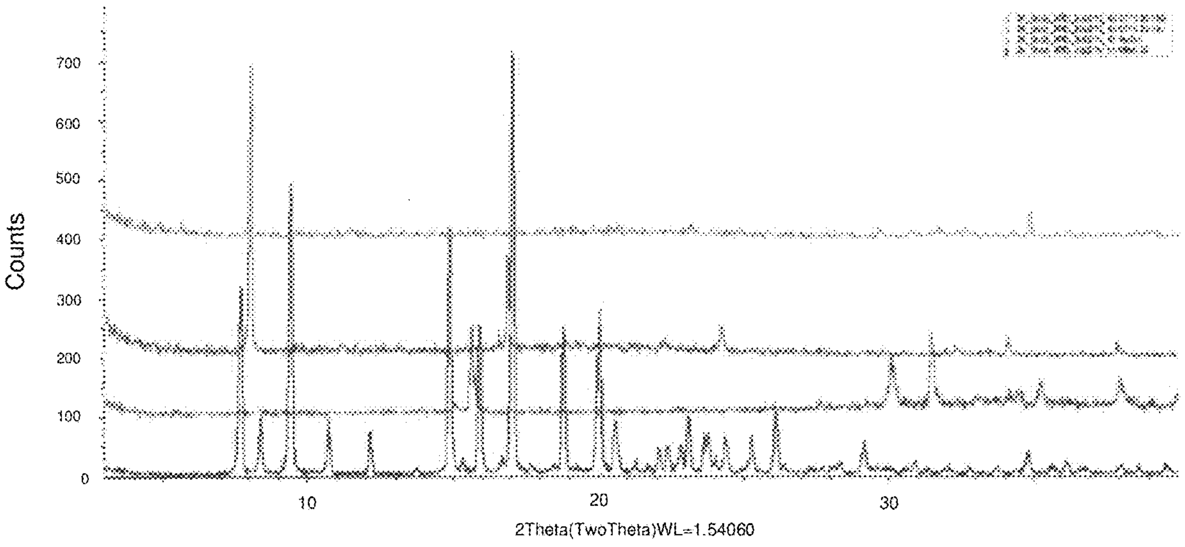
FIG. 27 is an overlay of XPRD patterns obtained from solid samples reacted with sodium hydroxide (blue trace) and potassium hydroxide (green trace) (the black trace is the second crystalline form of the compound of formula (I), and the magenta trace is sodium hydroxide). The new peaks in the blue and green traces represent new crystal structures; however, molecular degradation was visible via $^1$H NMR spectroscopy.
Figure 28:
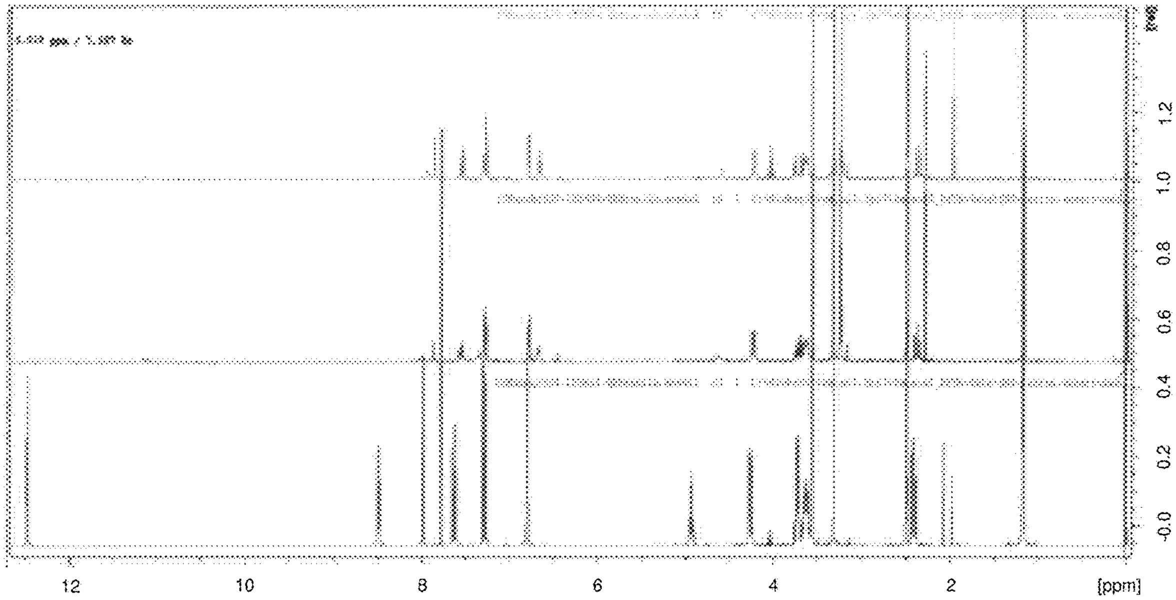
FIG. 28 is an overlay of $^1$H NMR spectra of the second crystalline form of the compound of formula (I) (blue trace) and materials formed in combining the compound of formula (I) with sodium hydroxide (magenta trace) and potassium hydroxide (green trace).
Figure 29:
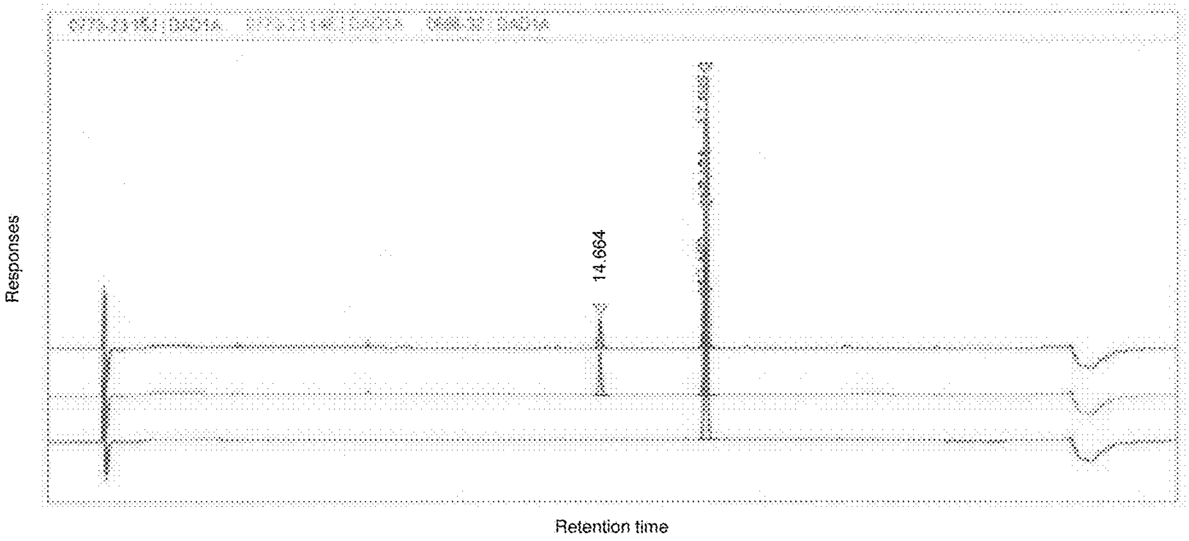
FIG. 29 is an overlay of HPLC chromatograms of the compound of formula (I) (bottom trace), and the materials formed in combining the compound of formula (I) with sodium hydroxide (middle trace) and potassium hydroxide (top trace). New peaks at 14.7 minutes in the sodium hydroxide and potassium hydroxide traces represent a degradation product.

The XRPD analysis of solids formed by the combination of the compound of formula (I) with sodium hydroxide and potassium hydroxide showed a new diffraction pattern, and hence, a new crystal structure (FIG. 27). However, molecular degradation was visible via $^1$H NMR spectroscopy in the increased noise of the baseline and HPLC analysis showed a new molecule eluting at 14.7 minutes (FIG. 28, FIG. 29). This suggests the new structure is a product of molecular degradation in a basic environment.

Figure 30:
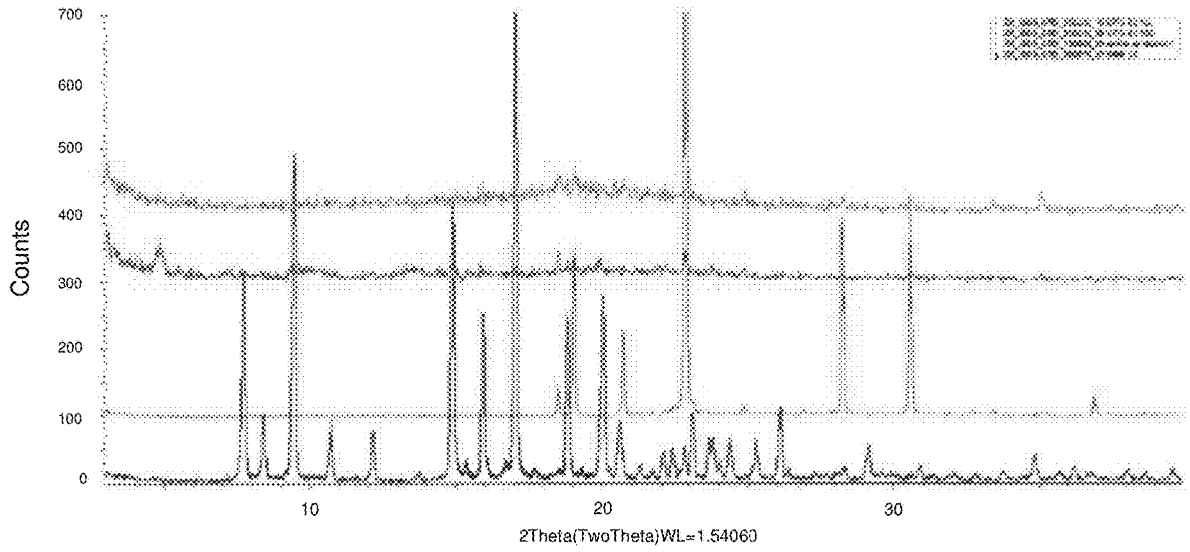
FIG. 30 is an overlay of XPRD patterns of the second crystalline form of the compound of formula (I) (black trace), serine (magenta trace), material formed by the evaporation of isopropanol with the compound of formula (I) and serine (blue trace), and material formed by the evaporation of methyl tert-butyl ether with the compound of formula (I) and serine (green trace). The green and blue traces show previously unobserved reflections at low intensity, suggesting the early stages of formation of a new crystalline form.
Figure 31:
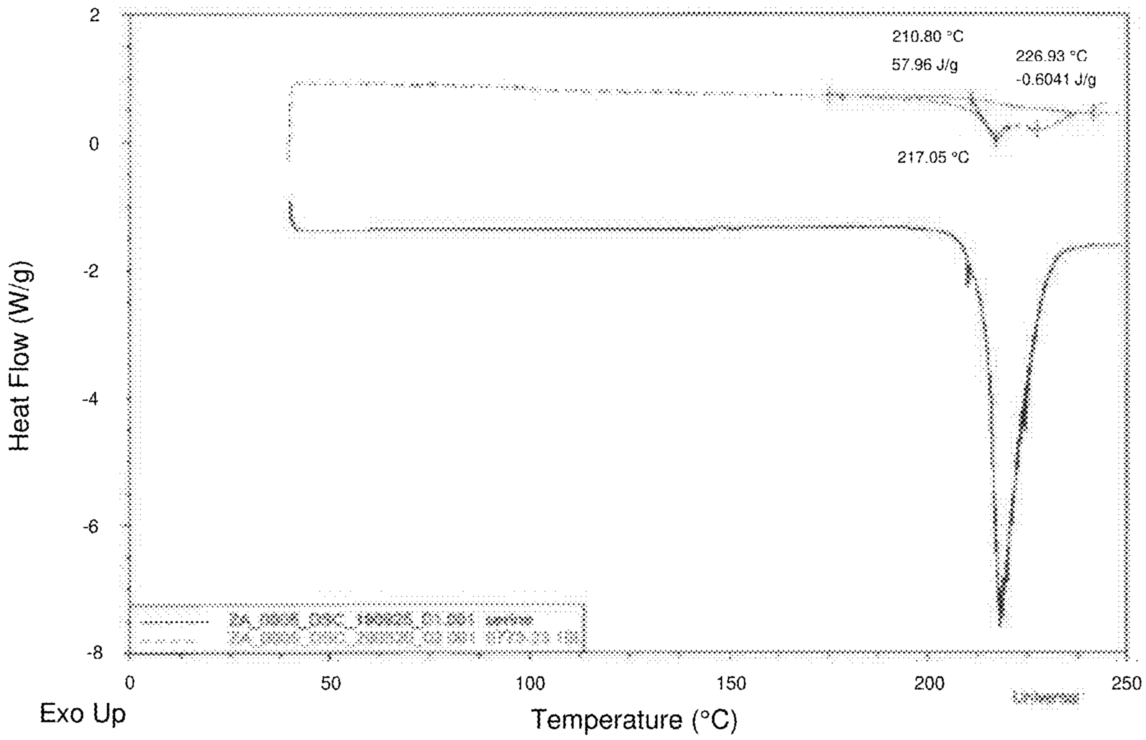
FIG. 31 is an overlay of DSC traces, comparing serine (bottom trace) with the material formed by the evaporation of methyl tert-butyl ether with the compound of formula (I) and serine (top trace). The endotherm at 217° C. corresponds with the serine melting temperature and the endotherm at 227° C. may indicate the presence of a second structure.

The XRPD analysis of solids formed by the combination of the compound of formula (I) with serine in isopropanol and MTBE showed previously unobserved reflections at low intensity, suggesting the early stages of formation of a new structure (FIG. 30). DSC analysis showed a melting endotherm at 217° C. which corresponds to serine melting temperature, followed by a second endotherm at 227° C. which potentially indicates the presence of a second structure (FIG. 31). Further characterization was not performed due to insufficient material, so serine was combined with the compound of formula (I) in isopropanol and MTBE and temperature cycled between 20° C. and 50° C. (for 10 cycles) in an attempt to recreate the new structure. However, the reproduction of the novel diffraction pattern was unsuccessful as XRPD analysis showed the samples are mixtures of serine and the second crystalline form of the compound of formula (I).

Amorphous Slurries.

Amorphous samples formed in the evaporative screen were transferred to vials, and the appropriate solvents were added dropwise to form a suspension. The suspensions were allowed to stir at room temperature for 2 days to allow transformation to crystalline structures. The solvent was then evaporated at room temperature, allowing any potential crystals present to seed further crystallization, in order to extract sufficient material for analysis.

Figure 32:
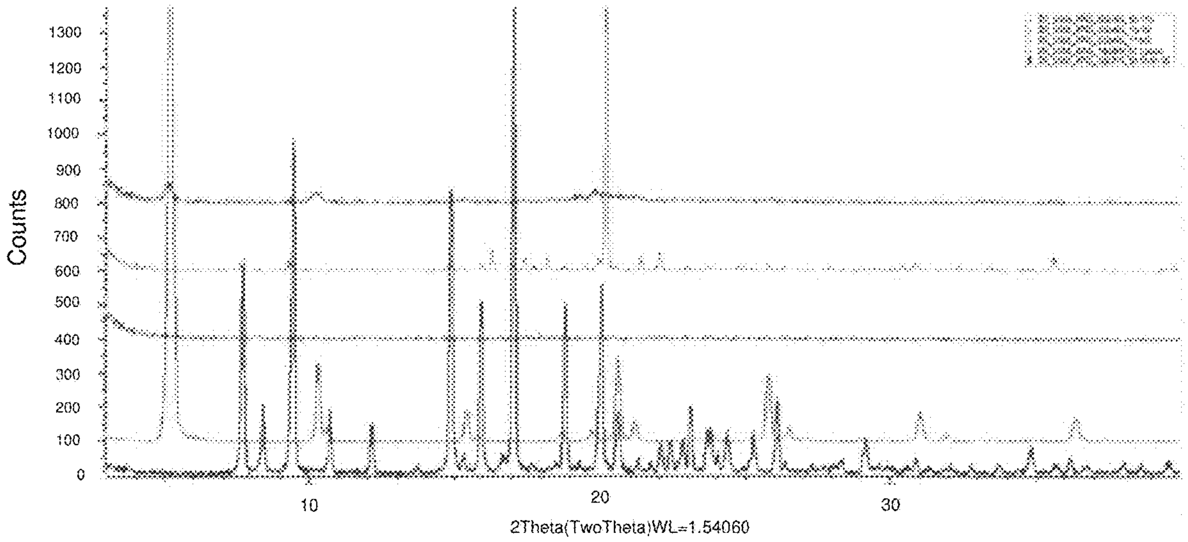
FIG. 32 is an overlay of XRPD patterns obtained from HCl in ethyl acetate (blue trace), magnesium sulfate in toluene (green trace), and lysine in xylenes (purple trace). The black and red traces are references of the second crystalline form of the compound of formula (I) and lysine, respectively. XRPD analysis showed the HCl material was amorphous, the magnesium sulfate material showed reflections characteristic of the second crystal form of the compound of formula (I) only, and the lysine material showed lysine reflections

Solid samples were obtained with HCl in ethyl acetate, magnesium sulfate in toluene, and lysine in xylenes. XRPD analysis showed the HCl material was amorphous, the magnesium sulfate material showed reflections characteristic of the second crystal form of the compound of formula (I) only, and the lysine material showed lysine reflections (FIG. 32). All other slurried samples formed oils.

Temperature Cycling in Toluene.

Based on the results of the evaporative screen, which showed a high percentage of solid amorphous material formed in toluene, the second crystalline form of the compound of formula (I) was suspended with 9 acids and temperature cycled between 5° C. and 50° C. (for 10 cycles) to encourage salt crystallization (Table 17). This experiment was also performed with HCl, oxalic acid, and ethane disulfonic acid in ethyl acetate. Solid samples were analyzed by XRPD, which showed that no new crystal structures were formed.

TABLE 17

| Acid | Solvent | Outcome |
|---|---|---|
| BSA | Methanol | Gel |
| TSA | Ethanol/water | Gel |
| Sulphuric acid | Isopropanol | Viscous solution |
| Malonic acid | 2-Butanol | The second crystalline form of the compound of formula (I) |
| Maleic acid | Acetone | The second crystalline form of the compound of formula (I) |
| Oxalic acid | Acetonitrile | The second crystalline form of the compound of formula (I) |
| Phosphoric acid | Ethyl acetate | Oil |
| HCl | Isopropyl acetate | Gel |
| EdSA | Toluene | Gel |
| HCl | Xylenes | Viscous solution |
| Oxalic acid | THF | The second crystalline form of the compound of formula (I) |
| EdSA | MTBE | Gel |

Reactive Screen in Ethyl Acetate.

The second crystalline form of the compound of formula (I) was combined with 8 acids in 1:1 equivalents, and ethyl acetate was added until dissolved or up to a maximum of 50 mL. Heptane was then added until a cloud point was observed. Amorphous material was initially generated but quickly converted to gels on the vial walls. The vials were allowed to stir at room temperature for up to 10 days and solid samples were analyzed by XRPD. Solids were formed when the compound of formula (I) was combined with oxalic acid and malonic acid; however, XRPD data showed the isolated solids were amorphous with oxalic acid, and were the second crystalline form of the compound of formula (I) with malonic acid. Table 18 summarizes the outcomes of the reactive screen of the compound of formula (I) with acidic counterions in ethyl acetate/heptane.

TABLE 18

| Acid | Outcome |
|---|---|
| Malonic acid | The second crystalline form of the compound of formula (I) |
| Maleic acid | Gel |
| Oxalic acid | Amorphous |
| TSA | Gel |
| BSA | Gel |
| HCl, sulfuric acid, EdSA | Did not dissolve |

Vials from the reactive screen were temperature cycled between 20° C. and 50° C. (for 10 cycles) to encourage crystallization. Solid material was observed in combinations with malonic acid, HCl, and ethane disulfonic acid; however, XRPD analysis showed the second crystalline form of the compound of formula (I) or amorphous diffraction patterns.

Hydrochloride Salt.

Several experiments were carried out in ethyl acetate to generate the hydrochloride salt:

The second crystalline form of the compound of formula (I) was suspended with HCl in ethyl acetate (1:1 equivalents) and allowed to stir for 3 days.

The second crystalline form of the compound of formula (I) was fully dissolved in ethyl acetate with HCl (1:1 equivalents), and 33% heptane anti-solvent was added to initiate nucleation. The vial was then temperature cycled between 20° C. and 50° C. (10 cycles) to encourage crystallization.

The second crystalline form of the compound of formula (I) was fully dissolved in ethyl acetate with HCl (1:1 equivalents) and a small amount of HCl salt seed was added to the solution before the addition of heptane. The suspension was allowed to stir at 30° C. for 3 days.

XRPD analysis showed that the unseeded experiments yield amorphous solids. However, the seeded sample exhibited low intensity reflections corresponding to the hydrochloride salt (HCl1).

Figure 33:
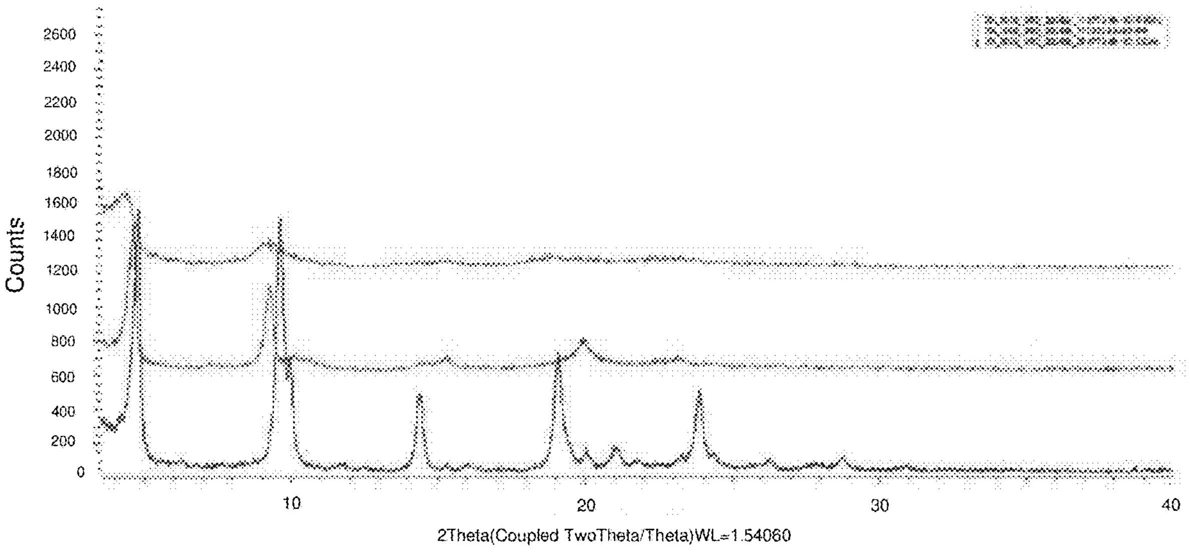
FIG. 33 is an overlay of XRPD patterns of hydrochloride salts formed in ethyl acetate (black trace), isopropanol (red trace), and isopropyl acetate (blue trace).
Figure 34:
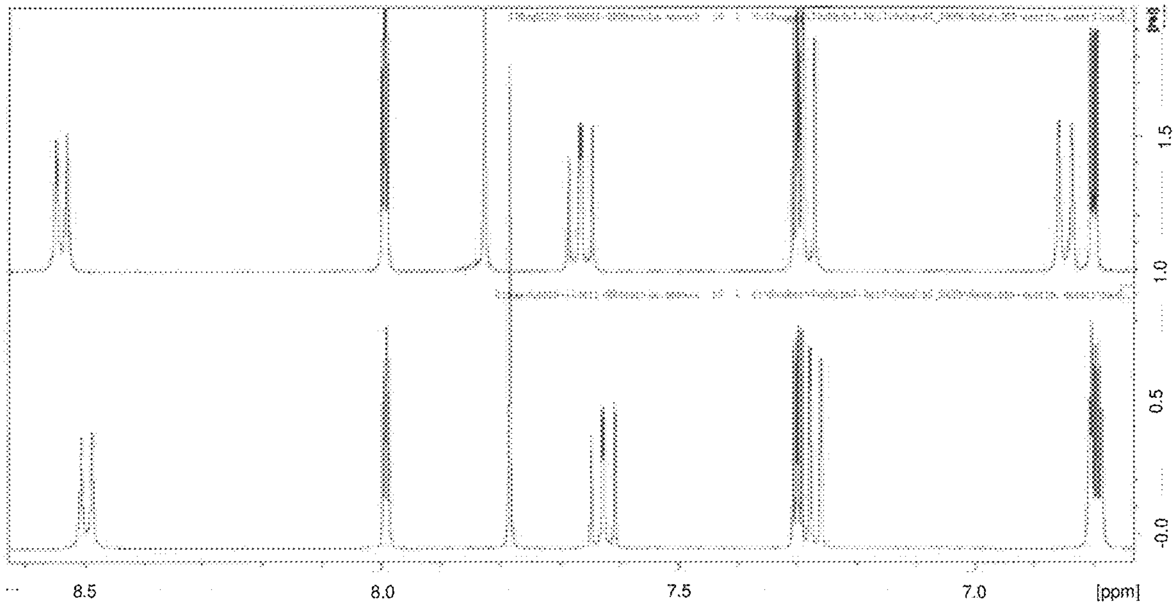
FIG. 34 is an overlay of $^1$H NMR spectra of the compound of formula (I) (blue trace) with the hydrochloride salt of the compound of formula (I) (magenta trace).
Figure 35:
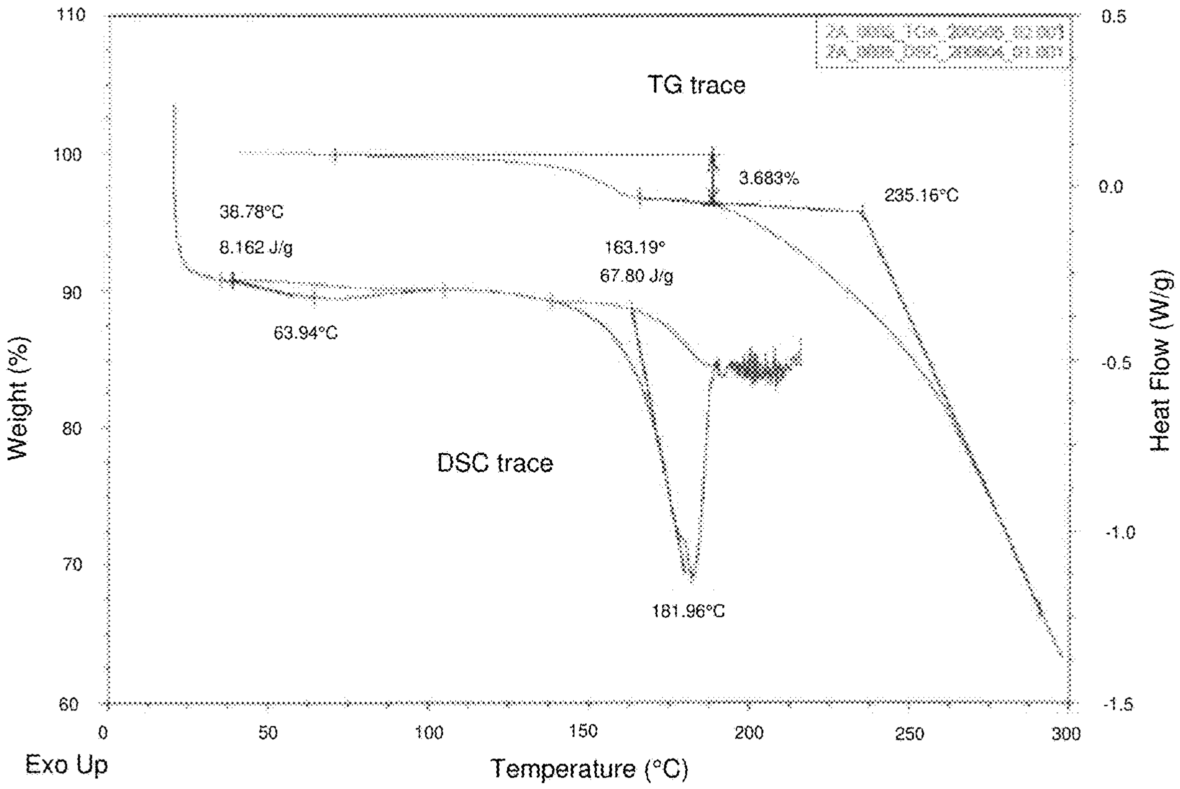
FIG. 35 is a plot of the TGA and DSC of the hydrochloride salt of the compound of formula (I) formed in ethyl acetate. The sample formed in ethyl acetate exhibited weight loss of 3.7% (w/w) at approximately 150° C., and molecular degradation from 195° C. with onset at 235° C. A melting endotherm was observed at 182° C. with an onset at 163.2° C., followed by degradation.
Figure 36A:
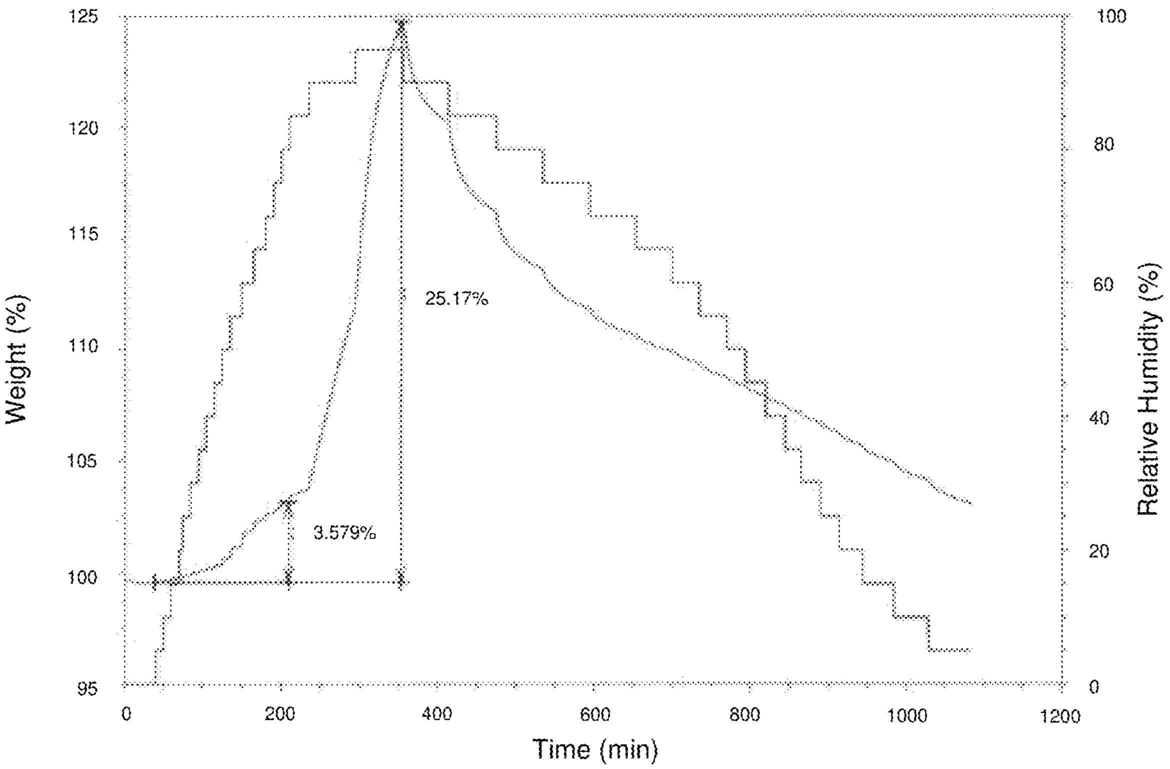
FIG. 36A is a plot showing the DVS cycles for the hydrochloride salt of the compound of formula (I). DVS analysis showed a weight increase of 3.6% (w/w) during exposure to 80% RH, hence the material is classified as hygroscopic, with a total weight increase of 25.2% (w/w) during exposure to 95% RH.
Figure 36B:
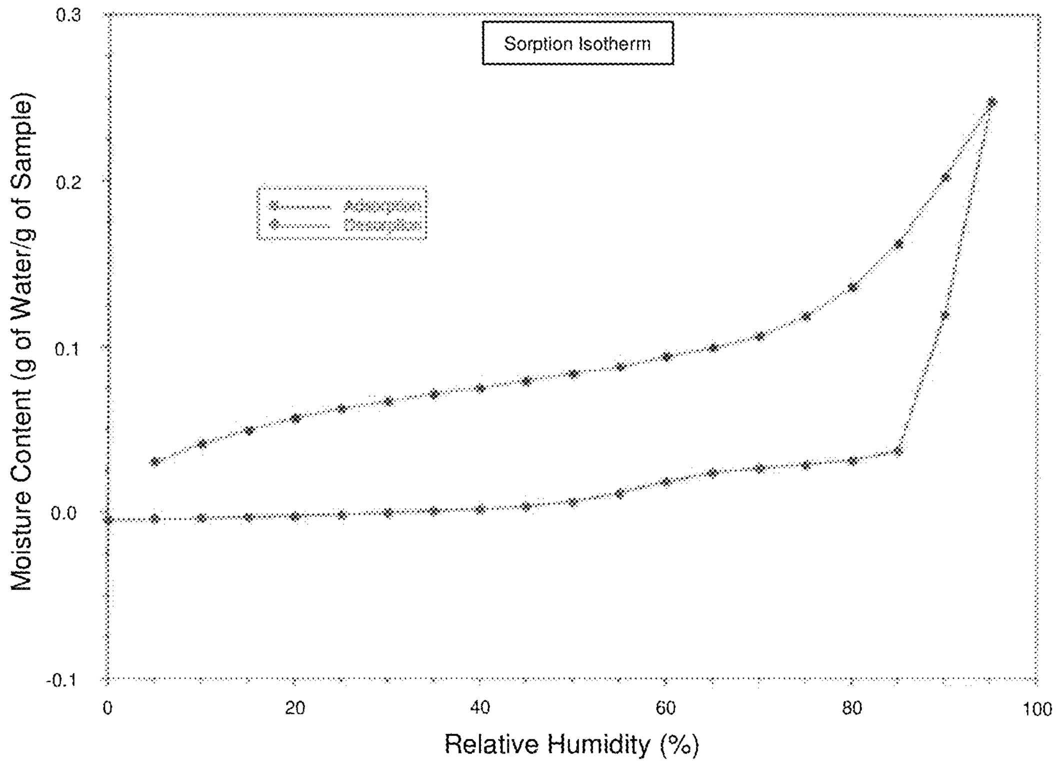
FIG. 36B is a DVS kinetic plot for the hydrochloride salt of the compound of formula (I).

A reactive screen using anhydrous concentrated HCl was performed in ethyl acetate, isopropyl acetate and isopropanol. The second crystalline form of the compound of formula (I) was suspended in ethyl acetate and HCl was added in 1:1 equivalents, which rapidly initiated nucleation. XRPD analysis showed the hydrochloride salt was successfully formed in all three solvents, with greatest crystallinity in ethyl acetate (FIG. 33). $^1$H NMR analysis confirmed the formation of a salt without degradation (FIG. 34). TGA and DSC data of the sample formed in ethyl acetate exhibited DSC data of the sample formed in ethyl acetate exhibited weight loss of 3.7% (w/w) at approximately 150° C., and molecular degradation from 195° C. with onset at 235° C. (FIG. 35). A melting endotherm was observed at 182° C. with an onset at 163.2° C., followed by degradation. DVS analysis showed a weight increase of 3.6% (w/w) during exposure to 80% RH, hence the material is classified as hygroscopic, with a total weight increase of 25.2% (w/w) during exposure to 95% RH (FIG. 36). After data collection, the sample was found to have deliquesced.

Reactive Screen in Isopropyl Acetate.

Figure 37:
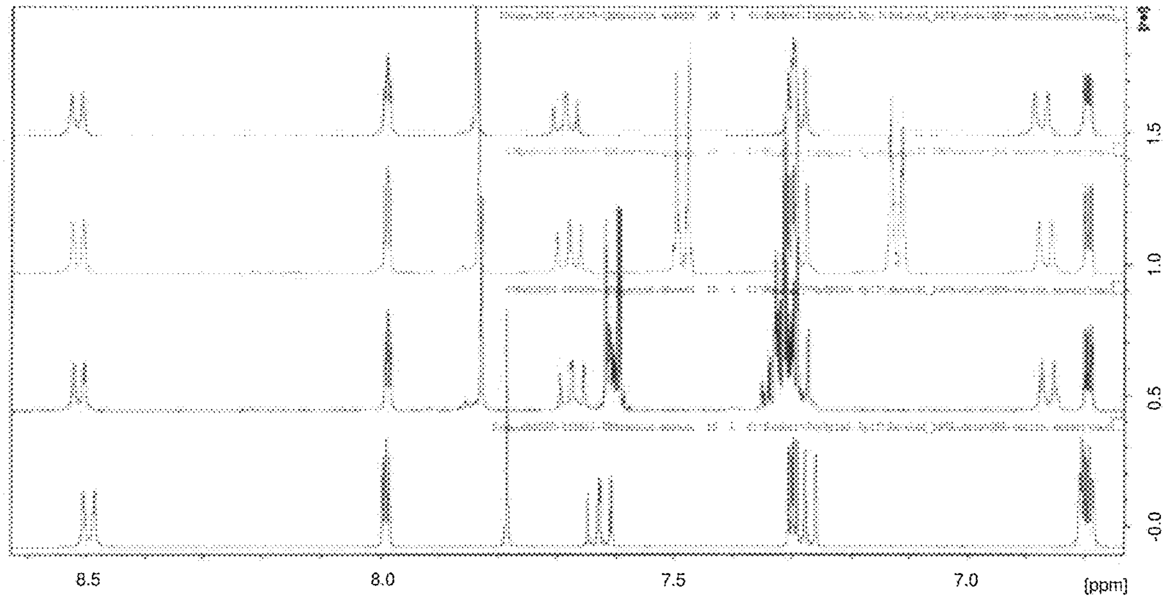
FIG. 37 is an overlay of $^1$H NMR spectra of various salts of the compound of formula (I) formed in isopropyl acetate (traces from top to bottom: ethane disulfonic acid salt, tosylate salt, besylate salt, and the compound of formula (I)).

The second crystalline form of the compound of formula (I) was combined with 5 acids in 1:1 equivalents, and isopropyl acetate was added until dissolved or up to a maximum of 60 mL. Heptane was then added until a cloud point was observed. XRPD analysis showed that all solids formed in isopropyl acetate were amorphous. However, $^1$H NMR spectroscopy on the solids showed a shift in resonance corresponding to protons on the aromatic group with no indication of degradation, suggesting that salts had been formed (FIG. 37). TGA analysis indicates the ethane disulfonic acid salt is highly unstable, whereas degradation occurs between 150° C. and 180° C. for the other salts. Modulated DSC performed with two heating cycles was performed on the salts. The besylate showed a glass transition temperature between 97.7° C. and 112.1° C., and the tosylate showed a glass transition temperature between 94.7° C. and 107.2° C. during the second cycle, indicating that under these measurement conditions the materials remained amorphous after melting. $^1$H NMR analysis was not carried out on the potential oxalate salt as it was insoluble in DMSO, hence it could not be confirmed as a salt. Table 19 summarizes the reactive salt screen of the compound of formula (I) with acidic counterions in isopropyl acetate/heptane.

TABLE 19

| Acid | Outcome |
|---|---|
| BSA | Amorphous salt |
| TSA | Amorphous salt |
| EdSA | Amorphous salt |
| Sulphuric acid | Gum |
| Oxalic acid | Amorphous solid |

Other Embodiments

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A crystalline form of the compound of formula (I):

(I)

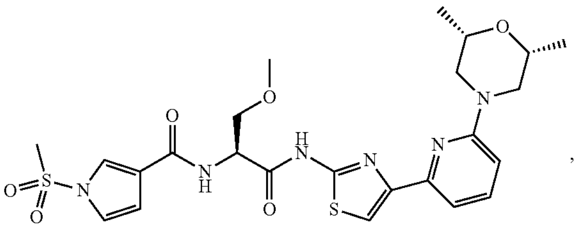

, wherein the crystalline form is characterized by a powder x-ray diffraction pattern having peaks at 14.4 °2θ±0.2 °2θ and 17.4 °2θ±0.2 °2θ.

2. The crystalline form of claim 1, wherein the crystalline form is further characterized by a powder x-ray diffraction pattern having peaks at 11.7 °2θ±0.2 °2θ and 15.2 °2θ±0.2 °2θ.

3. The crystalline form of claim 1, wherein the crystalline form is further characterized by a powder x-ray diffraction pattern having peaks at 14.9 °2θ±0.2 °2θ and 18.5 °2θ±0.2 °2θ.

4. The crystalline form of claim 1, wherein the crystalline form is further characterized by a powder x-ray diffraction pattern having peaks at 16.0 °2θ±0.2 °2θ and 19.1 °2θ±0.2 °2θ.

5. The crystalline form of claim 1, wherein the crystalline form is further characterized by a powder x-ray diffraction pattern having a peak at 16.3 °2θ±0.2 °2θ.

6. The crystalline form of claim 1, wherein the crystalline form is further characterized by a powder x-ray diffraction pattern having peaks at 20.6 °2θ±0.2 °2θ and 26.3 °2θ±0.2 °2θ.

7. The crystalline form of claim 1, wherein the crystalline form is further characterized by a powder x-ray diffraction pattern having peaks at 21.2 °2θ±0.2 °2θ and 26.6 °2θ±0.2 °2θ.

8. The crystalline form of claim 1, wherein the crystalline form is further characterized by a differential scanning calorimetry thermogram having an endothermic event onset at 173.5° C. to 180.1° C.

9. A crystalline form of the compound of formula (I):

(I)

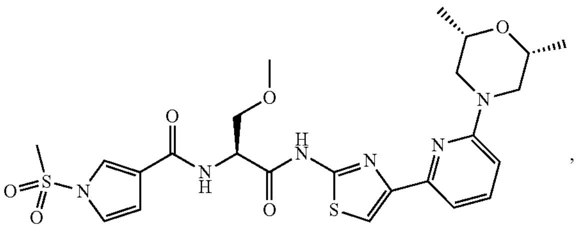

, wherein the crystalline form is characterized by a powder x-ray diffraction pattern having peaks at 7.7 °2θ±0.2 °2θ, 9.4 °2θ±0.2 °2θ and 17.0 °2θ±0.2 °2θ.

10. A pharmaceutical composition comprising the crystalline form of claim 1.

11. A unit dosage form comprising the crystalline form of claim 9.

* * * * *